United States Patent
Heer et al.

(10) Patent No.: US 10,793,578 B2
(45) Date of Patent: Oct. 6, 2020

(54) FUSED PENTACYCLIC IMIDAZOLE DERIVATIVES AS MODULATORS OF TNF ACTIVITY

(71) Applicants: UCB Biopharma SRL, Brussels (BE); Sanofi, Paris (FR)

(72) Inventors: Jag Paul Heer, Slough (GB); Jean Keyaerts, Brussels (BE)

(73) Assignees: UCB Biopharma SRL, Brussels (BE); Sanofi, Paris (FR)

( * ) Notice: Subject to any disclaimer, the term of this patent is extended or adjusted under 35 U.S.C. 154(b) by 0 days.

(21) Appl. No.: 16/086,311

(22) PCT Filed: Mar. 31, 2017

(86) PCT No.: PCT/EP2017/057769
§ 371 (c)(1),
(2) Date: Sep. 18, 2018

(87) PCT Pub. No.: WO2017/167996
PCT Pub. Date: Oct. 5, 2017

(65) Prior Publication Data
US 2019/0112314 A1    Apr. 18, 2019

(30) Foreign Application Priority Data

Apr. 1, 2016   (EP) ..................... 16163572

(51) Int. Cl.
| C07D 487/18 | (2006.01) |
| C07D 487/04 | (2006.01) |
| C07D 487/22 | (2006.01) |
| A61P 25/28 | (2006.01) |
| A61P 37/04 | (2006.01) |
| A61P 3/00 | (2006.01) |
| A61P 9/00 | (2006.01) |

(52) U.S. Cl.
CPC ......... *C07D 487/18* (2013.01); *C07D 487/04* (2013.01); *C07D 487/22* (2013.01); *A61P 3/00* (2018.01); *A61P 9/00* (2018.01); *A61P 25/28* (2018.01); *A61P 37/04* (2018.01)

(58) Field of Classification Search
None
See application file for complete search history.

(56) References Cited

U.S. PATENT DOCUMENTS

2015/0152065 A1   6/2015   Brookings et al.

FOREIGN PATENT DOCUMENTS

| WO | WO 2004/087720 | 10/2004 |
| WO | WO 2009/156091 | 12/2009 |
| WO | WO 2012/135082 | 10/2012 |
| WO | WO 2012/177707 | 12/2012 |
| WO | WO 2013/186229 | 12/2013 |
| WO | WO 2014/009295 | 1/2014 |
| WO | WO 2014/009296 | 1/2014 |
| WO | WO 2015/086525 | 6/2015 |
| WO | WO 2015/086526 | 6/2015 |
| WO | WO 2016/050975 | 4/2016 |

OTHER PUBLICATIONS

Tansey & Szymkowski, Drug Discovery Today, 2009, 14, 1082-1088.
Carneiro et al., J. Sexual medicine, 2010, 7, 3823-3824.
Wu et al., JAMA, 2013, 309, 2043-2044.
Hauwermeiren et al., J. Clin. Invest, 2013, 123, 2590-2603.
Okamura & Bohm, Organic Letters, 2004, 6(8), 1305-1307.
Hilpert et al., Journal of Medicinal Chemistry, 2013, 56(10), 3980-3995.
Armstrong et al., J. Org. Chem., 2013, 78, 10534.
Nagib & McMillan, Nature, 2011, 480, 224.
Bahrami et al., J. Org. Chem., 2009, 74, 9287-9291.
Sakai et al., J. Org. Chem., 20 2007, 72, 5920-5922.
Bentley et al., Organic Process Research & Development, 2002, 6(2), 109-112.
Nam et al., Bio-org. Med. Chem., 2004, 12, 6255.
Lacko et al., Current Medicinal Chemistry, 2012, 19, 4699.

*Primary Examiner* — Samantha L Shterengarts
(74) *Attorney, Agent, or Firm* — McDonnell Boehnen Hulbert & Berghoff LLP

(57) ABSTRACT

A series of fused pentacyclic imidazole derivatives, being potent modulators of f benefit in the treatment and/or prevention of various human ailments, including autoimmune and inflammatory disorders; neurological and neurodegenerative disorders; pain and nociceptive disorders; cardiovascular disorders; metabolic disorders; ocular disorders; and oncological disorders. In particular, the present invention is concerned with 5,7,8,15-tetrahydro-6H-8,15-methanobenzimidazo[1,2-b][2,5]benzodiazocin-6-one derivatives and analogs thereof.

7 Claims, No Drawings

FUSED PENTACYCLIC IMIDAZOLE DERIVATIVES AS MODULATORS OF TNF ACTIVITY

This application is the US national phase under 35 U.S.C. § 371 of international application PCT/EP2017/057769, filed Mar. 31, 2017, which claims priority to European application 16163572.7, filed Apr. 1, 2016.

The present invention relates to classes of fused pentacyclic imidazole derivatives, and to their use in therapy. More particularly, this invention is concerned with pharmacologically active substituted fused pentacyclic benzimidazole derivatives and analogs thereof. In particular, the present invention is concerned with 5,7,8,15-tetrahydro-6H-8,15-methanobenzimidazo[1,2-b][2,5]benzodiazocin-6-one derivatives and analogs thereof.

These compounds are modulators of the signalling of TNFα, and are accordingly of benefit as pharmaceutical agents, especially in the treatment of adverse inflammatory and autoimmune disorders, neurological and neurodegenerative disorders, pain and nociceptive disorders, cardiovascular disorders, metabolic disorders, ocular disorders, and oncological disorders.

TNFα is the prototypical member of the Tumour Necrosis Factor (TNF) superfamily of proteins that share a primary function of regulating cell survival and cell death. One structural feature common to all known members of the TNF superfamily is the formation of trimeric complexes that bind to, and activate, specific TNF superfamily receptors. By way of example, TNFα exists in soluble and transmembrane forms and signals through two receptors, known as TNFR1 and TNFR2, with distinct functional endpoints.

Various products capable of modulating TNFα activity are already commercially available. All are approved for the treatment of inflammatory and autoimmune disorders such as rheumatoid arthritis and Crohn's disease. All currently approved products are macromolecular and act by inhibiting the binding of human TNFα to its receptor. Typical macromolecular TNFα inhibitors include anti-TNFα antibodies; and soluble TNFα receptor fusion proteins. Examples of commercially available anti-TNFα antibodies include fully human antibodies such as adalimumab (Humira®) and golimumab (Simponi®), chimeric antibodies such as infliximab (Remicade®), and pegylated Fab' fragments such as certolizumab pegol (Cimzia®). An example of a commercially available soluble TNFα receptor fusion protein is etanercept (Enbrel®).

TNF superfamily members, including TNFα itself, are implicated in a variety of physiological and pathological functions that are believed to play a part in a range of conditions of significant medical importance (see, for example, M. G. Tansey & D. E. Szymkowski, *Drug Discovery Today,* 2009, 14, 1082-1088; and F. S. Carneiro et al., *J. Sexual Medicine,* 2010, 7, 3823-3834).

The compounds in accordance with the present invention, being potent modulators of human TNFα activity, are therefore beneficial in the treatment and/or prevention of various human ailments. These include autoimmune and inflammatory disorders; neurological and neurodegenerative disorders; pain and nociceptive disorders; cardiovascular disorders; metabolic disorders; ocular disorders; and oncological disorders.

In addition, the compounds in accordance with the present invention may be beneficial as pharmacological standards for use in the development of new biological tests and in the search for new pharmacological agents. Thus, in one embodiment, the compounds of this invention may be useful as radioligands in assays for detecting pharmacologically active compounds. In an alternative embodiment, certain compounds of this invention may be useful for coupling to a fluorophore to provide fluorescent conjugates that can be utilised in assays (e.g. a fluorescence polarisation assay) for detecting pharmacologically active compounds.

International patent applications WO2013/186229A1, WO2014/009295A1 and WO2014/009296A1 relate to fused imidazole derivatives which are modulators of the signalling of TNFα.

International patent applications WO2015/086525 and WO2015/086526 published Jun. 18, 2015 relate to fused tricyclic imidazole derivatives which are modulators of the signalling of TNFα.

Co-pending international patent application PCT/EP2015/072868, published on 7 Apr. 2016 as WO 2016/050975, relates to fused pentacyclic imidazole derivatives which are modulators of the signalling of TNFα.

None of the prior art available to date, however, discloses or suggests the precise structural class of fused pentacyclic imidazole derivatives as provided by the present invention.

The present invention provides a compound of formula (I) or an N-oxide thereof, or a pharmaceutically acceptable salt thereof:

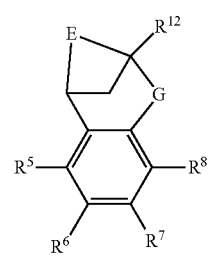

(I)

wherein

-G- represents —O—C(O)—N(R$^f$)—, —N(R$^f$)—C(O)—N(R$^f$)— or —N(R$^f$)—S(O)$_2$—N(R$^f$)—; or -G- represents —N(R$^f$)—C(O)—CH$_2$—, CH$_2$—N(R$^f$)—C(O)—, —C(O)—N(R$^f$)—CH$_2$—, —N(R$^g$)—CH$_2$—CH$_2$—, —S(O)$_2$—N(R$^f$)—CH$_2$—, —N(R$^f$)—S(O)$_2$—CH$_2$—, —O—CH$_2$—CH$_2$—, —S—CH$_2$—CH$_2$—, —S(O)—CH$_2$—CH$_2$, —S(O)$_2$—CH$_2$—CH$_2$—, —S(O)(N—R$^f$)—CH$_2$—CH$_2$—, —O—C(O)—CH$_2$—, —O—S(O)$_2$—N(R$^f$)—, —N(Rf)—C(O)—O—CH$_2$, or —N(R$^f$)—C=N(R$^f$)—CH$_2$, any of which groups may be optionally substituted by one or more substituents;

E represents a fused heteroaromatic ring system selected from the groups of formula (Ea), (Eb) and (Ec),

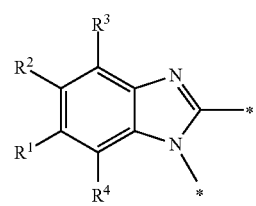

(Ea)

-continued

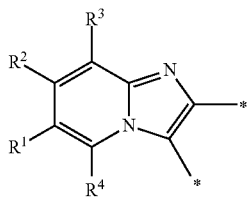

(Eb)

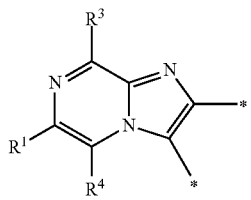

(Ec)

wherein the asterisk (*) represents the site of attachment of E to the remainder of the molecule;

$R^1$ represents hydrogen, halogen, cyano, trifluoromethyl, trifluoromethoxy, —$OR^a$, —$SR^a$, —$SOR^a$, —$SO_2R^a$, —$NR^bR^c$, —$NR^cCOR^d$, —$NR^cCO_2R^d$, —$NHCONR^bR^c$, —$NR^cSO_2R^e$, —$COR^d$, —$CO_2R^d$, —$CONR^bR^c$, —$SO_2NR^bR^c$ or —$S(O)(N—R^b)R^e$; or $R^1$ represents $C_{1-6}$ alkyl, $C_{3-7}$ cycloalkyl, $C_{4-7}$ cycloalkenyl, aryl, aryl($C_{1-6}$) alkyl, $C_{3-7}$ heterocycloalkyl, $C_{3-7}$ heterocycloalkenyl, heteroaryl, heteroaryl($C_{1-6}$)alkyl, heteroaryl-aryl, ($C_{3-7}$)heterocycloalkyl($C_{1-6}$)alkyl-aryl-, ($C_{3-7}$)heterocycloalkenyl-aryl-, ($C_{3-7}$)cycloalkyl-heteroaryl-, ($C_{3-7}$)cycloalkyl($C_{1-6}$)alkyl-heteroaryl-, ($C_{4-7}$)cycloalkenyl-heteroaryl-, ($C_{4-9}$)bicycloalkyl-heteroaryl-, ($C_{3-7}$)heterocycloalkyl-heteroaryl-, ($C_{3-7}$)heterocycloalkyl($C_{1-6}$)alkyl-heteroaryl-, ($C_{3-7}$)heterocycloalkenyl-heteroaryl-, ($C_{4-9}$)heterobicycloalkyl-heteroaryl- or ($C_{4-9}$)spiroheterocycloalkyl-heteroaryl-, any of which groups may be optionally substituted by one or more substituents;

$R^2$ represents hydrogen, halogen, cyano, nitro, hydroxy, trifluoromethyl, trifluoromethoxy or —$OR^a$; or $R^2$ represents $C_{1-6}$ alkyl optionally substituted by one or more substituents;

$R^3$ and $R^4$ independently represent hydrogen, halogen or trifluoromethyl; or $R^3$ and $R^4$ independently represent $C_{1-6}$ alkyl, optionally substituted by one or more substituents;

$R^5$ and $R^8$ independently represent hydrogen, halogen, hydroxy, cyano, trifluoromethyl, difluoromethoxy, trifluoromethoxy, —$OR^a$, or $C_{1-6}$ alkylsulphonyl; or $R^5$ and $R^8$ independently represent $C_{1-6}$ alkyl optionally substituted by one or more substituents;

$R^6$ and $R^7$ independently represent hydrogen, halogen, trifluoromethyl, $C_{1-6}$ alkyl or $C_{1-6}$ alkoxy;

$R^{12}$ represents hydrogen or $C_{1-6}$ alkyl;

$R^a$ represents $C_{1-6}$ alkyl, $C_{3-7}$ cycloalkyl, $C_{3-7}$ heterocycloalkyl, aryl, aryl($C_{1-6}$)alkyl, heteroaryl or heteroaryl($C_{1-6}$) alkyl, any of which groups may be optionally substituted by one or more substituents;

$R^b$ and $R^c$ independently represent hydrogen or trifluoromethyl; or $R^b$ and $R^c$ independently represent $C_{1-6}$ alkyl, $C_{3-7}$ cycloalkyl, $C_{3-7}$ cycloalkyl($C_{1-6}$)alkyl, aryl, aryl($C_{1-6}$) alkyl, $C_{3-7}$ heterocycloalkyl, $C_{3-7}$ heterocycloalkyl($C_{1-6}$) alkyl, heteroaryl or heteroaryl($C_{1-6}$)alkyl, any of which groups may be optionally substituted by one or more substituents; or $R^b$ and $R^c$, when taken together with the nitrogen atom to which they are both attached, represent a heterocyclic moiety selected from azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl, homopiperazin-1-yl, (imino)(oxo)thiazinan-4-yl, (oxo)thiazinan-4-yl and (dioxo)thiazinan-4-yl, any of which groups may be optionally substituted by one or more substituents;

$R^d$ represents hydrogen; or $R^d$ represents $C_{1-6}$ alkyl, $C_{3-7}$ cycloalkyl, aryl, $C_{3-7}$ heterocycloalkyl or heteroaryl, any of which groups may be optionally substituted by one or more substituents;

$R^e$ represents $C_{1-6}$ alkyl, aryl or heteroaryl, any of which groups may be optionally substituted by one or more substituents;

$R^f$ represents hydrogen; or $R^f$ represents $C_{1-6}$ alkyl, $C_{3-7}$ cycloalkyl, or $C_{3-7}$ heterocycloalkyl, $C_{1-6}$ alkylcarbonyl, $C_{1-6}$ alkylsulfonyl any of which groups may be optionally substituted by one or more substituents; and $R^g$ represents hydrogen or ($C_{2-6}$)alkoxycarbonyl; or $R^g$ represents $C_{1-6}$ alkyl, $C_{3-7}$ cycloalkyl, $C_{3-7}$ heterocycloalkyl, heteroaryl, —CO—($C_{1-6}$)alkyl, or —$SO_2$—($C_{1-6}$)alkyl, —CO—($C_{3-7}$)heterocycloalkyl, —$SO_2$—($C_{3-7}$)cycloalkyl, —$SO_2$—($C_{3-7}$)heterocycloalkyl, —$SO_2$-aryl, or —$SO_2$-heteroaryl, any of which groups may be optionally substituted by one or more substituents.

The present invention also provides a compound of formula (I) as defined above or an N-oxide thereof, or a pharmaceutically acceptable salt thereof, for use in therapy.

In another aspect, the present invention also provides a compound of formula (I) as defined above or an N-oxide thereof, or a pharmaceutically acceptable salt thereof, for use in the treatment and/or prevention of disorders for which the administration of a modulator of TNFα function is indicated.

In another aspect, the present invention provides a compound of formula (I) as defined above or an N-oxide thereof, or a pharmaceutically acceptable salt thereof for use in the treatment and/or prevention of an inflammatory or autoimmune disorder, a neurological or neurodegenerative disorder, pain or a nociceptive disorder, a cardiovascular disorder, a metabolic disorder, an ocular disorder, or an oncological disorder.

In another aspect, the present invention provides for the use of a compound of formula (I) as defined above, or an N-oxide thereof, or a pharmaceutically acceptable salt thereof, for the manufacture of a medicament useful for the treatment and/or prevention of disorders for which the administration of a modulator of TNFα function is indicated.

In another aspect, the present invention provides for the use of a compound of formula (I) as defined above, or an N-oxide thereof, or a pharmaceutically acceptable salt thereof, for the manufacture of a medicament useful for the treatment of an inflammatory or autoimmune disorder, a neurological or neurodegenerative disorder, pain or a nociceptive disorder, a cardiovascular disorder, a metabolic disorder, an ocular disorder, or an oncological disorder.

The present invention also provides a method for the treatment and/or prevention of disorders for which the administration of a modulator of TNFα function is indicated which comprises administering to a patient in need of such treatment an effective amount of a compound of formula (I) as defined above, or an N-oxide thereof, or a pharmaceutically acceptable salt thereof.

In another aspect, the present invention provides a method for the treatment and/or prevention of an inflammatory or autoimmune disorder, a neurological or neurodegenerative disorder, pain or a nociceptive disorder, a cardiovascular disorder, a metabolic disorder, an ocular disorder, or an oncological disorder, which comprises administering to a patient in need of such treatment an effective amount of a compound of formula (I) as defined above or an N-oxide thereof, or a pharmaceutically acceptable salt thereof.

Where any of the groups in the compounds of formula (I) above is stated to be optionally substituted, this group may be unsubstituted, or substituted by one or more substituents. Typically, such groups will be unsubstituted, or substituted by one or two substituents. Suitable substitutents for each particular groups of compounds formula (I) are further described here after in the present specification.

The present invention includes within its scope salts of the compounds of formula (I) above. For use in medicine, the salts of the compounds of formula (I) will be pharmaceutically acceptable salts. Other salts may, however, be useful in the preparation of the compounds of use in the invention or of their pharmaceutically acceptable salts. Standard principles underlying the selection and preparation of pharmaceutically acceptable salts are described, for example, in *Handbook of Pharmaceutical Salts: Properties, Selection and Use*, ed. P. H. Stahl & C. G. Wermuth, Wiley-VCH, 2002.

The present invention includes within its scope solvates of the compounds of formula (I) above. Such solvates may be formed with common organic solvents or water.

The present invention also includes within its scope co-crystals of the compounds of formula (I) above. The technical term "co-crystal" is used to describe the situation where neutral molecular components are present within a crystalline compound in a definite stoichiometric ratio. The preparation of pharmaceutical co-crystals enables modifications to be made to the crystalline form of an active pharmaceutical ingredient, which in turn can alter its physicochemical properties without compromising its intended biological activity (see *Pharmaceutical Salts and Co-crystals*, ed. J. Wouters & L. Quere, RSC Publishing, 2012).

The present invention includes within its scope N-oxides of compounds of formula (I) above. Particular examples of N-oxides according to the present invention include pyrimidine N-oxide and pyridine N-oxide as illustrated in the Examples.

The term "alkyl" as used herein refers to aliphatic hydrocarbon groups which may be straight or branched and may comprise 1 to 20 carbon atoms in the chain, suitably 1 to 15 carbon atoms in the chain, more suitably 1 to 10 carbon atoms in the chain. Suitable alkyl groups which may be present on the compounds of use in the invention include straight-chained and branched $C_{1-6}$ alkyl groups, for example $C_{1-4}$ alkyl groups. Illustrative alkyl goups include methyl and ethyl groups, and straight-chained or branched propyl, butyl and pentyl groups. Suitable alkyl groups include methyl, ethyl, n-propyl, and isopropyl. Derived expressions such as "$C_{1-6}$ alkoxy", "$C_{1-6}$ alkylthio", "$C_{1-6}$ alkylsulphonyl" and "$C_{1-6}$ alkylamino" are to be construed accordingly.

The term "$C_{3-7}$ cycloalkyl" as used herein refers to monovalent groups of 3 to 7 carbon atoms derived from a saturated monocyclic hydrocarbon. Suitable $C_{3-7}$ cycloalkyl groups may comprise benzo-fused analogues thereof. Illustrative $C_{3-7}$ cycloalkyl groups include cyclopropyl, cyclobutyl, benzocyclobutenyl, cyclopentyl, indanyl, cyclohexyl and cycloheptyl.

The term "$C_{4-9}$ bicycloalkyl" as used herein refers to monovalent groups of 4 to 9 carbon atoms derived from a saturated bicyclic hydrocarbon. The term "$C_{4-7}$ cycloalkenyl" as used herein refers to monovalent groups of 4 to 7 carbon atoms derived from a partially unsaturated monocyclic hydrocarbon. Illustrative $C_{4-7}$ cycloalkenyl groups include cyclobutenyl, cyclopentenyl, cyclohexenyl and cycloheptenyl.

The term "aryl" as used herein, refers to an unsaturated aromatic carbocyclic group of from 6 to 14 carbon atoms having a single ring (e.g. phenyl) or multiple condensed rings (e.g. naphthyl). Illustrative aryl groups include phenyl.

Illustrative aryl($C_{1-6}$)alkyl groups include benzyl, phenylethyl and phenylpropyl.

The term "$C_{3-7}$ heterocycloalkyl" as used herein refers to saturated monocyclic rings containing 3 to 7 carbon atoms and at least one heteroatom selected from oxygen, sulphur and nitrogen, and may comprise benzo-fused analogues thereof. Illustrative heterocycloalkyl groups include oxetanyl, azetidinyl, pyrrolidinyl, piperidinyl, tetrahydrofuranyl, morpholinyl, dihydrobenzo-furanyl, dihydrobenzothienyl, pyrrolidinyl, indolinyl, dihydroisoindolinyl, isoindolinyl, oxazolidinyl, thiazolidinyl, isothiazolidinyl, imidazolidinyl, tetrahydropyranyl, chromanyl, tetrahydro-thiopyranyl, piperidinyl, 1,2,3,4-tetrahydroquinolinyl, 1,2,3,4-tetrahydroisoquinolinyl, piperazinyl, 1,2,3,4-tetrahydroquinoxalinyl, hexahydro-[1,2,5]thiadiazolo[2,3-a]pyrazinyl, homopiperazinyl, morpholinyl, benzoxazinyl, thiomorpholinyl, azepanyl, oxazepanyl, diazepanyl, thiadiazepanyl, azocanyl, (imino)(oxo)thiazinanyl, (oxo)thiazinanyl, (dioxo)thiazinanyl, tetrahydrothiophenyl, (oxo)tetrahydrothiophenyl, (dioxo)tetrahydrothiophenyl and (oxo)thiomorpholinyl.

The term "$C_{3-7}$ heterocycloalkenyl" as used herein refers to monounsaturated or polyunsaturated monocyclic rings containing 3 to 7 carbon atoms and at least one heteroatom selected from oxygen, sulphur and nitrogen, and may comprise benzo-fused analogues thereof. Illustrative heterocycloalkenyl groups include dihydropyranyl, dihydrothiopyranyl,1,2,3,6-tetrahydropyridinyl, 1,2-dihydropyridinyl and 1,2-dihydropyrimidinyl.

The term "$C_{4-9}$ heterobicycloalkyl" as used herein refers to a $C_{4-9}$ bicycloalkyl as defined herein, wherein one or more of the carbon atoms have been replaced by one or more heteroatoms selected from oxygen, sulphur and nitrogen. Illustrative heterobicycloalkyl groups include 3-azabicyclo[3.1.0]hexanyl, 2-oxa-5-azabicyclo[2.2.1]heptanyl, 6-azabicyclo[3.2.0]heptanyl, 3-azabicyclo[3.1.1]heptanyl, 3-azabicyclo[4.1.0]heptanyl, 2-oxabicyclo[2.2.2]octanyl, quinuclidinyl, 2-oxa-5-azabicyclo-[2.2.2]octanyl, 3-azabicyclo[3.2.1]octanyl, 8-azabicyclo[3.2.1]octanyl, 3-oxa-8-azabicyclo[3.2.1]octanyl, 3,8-diazabicyclo[3.2.1]octanyl, 3,6-diazabicyclo[3.2.2]nonanyl, 3-oxa-7-azabicyclo[3.3.1]nonanyl, 3,9-diazabicyclo[4.2.1]nonanyland 3,7-dioxa-9-azabicyclo[3.3.1]non-9-yl.

The term "$C_{4-9}$ spiroheterocycloalkyl" as used herein refers to saturated bicyclic ring systems containing 4 to 9 carbon atoms and at least one heteroatom selected from oxygen, sulphur and nitrogen, in which the two rings are linked by a common atom. Illustrative spiroheterocycloalkyl groups include 5-azaspiro[2.3]hexanyl, 5-azaspiro-[2.4]heptanyl, 2-azaspiro[3.3]heptanyl, 2-oxa-6-azaspiro[3.3]heptanyl, 2-oxa-6-azaspiro-[3.4]octanyl, 2-oxa-6-azaspiro[3.5]nonanyl, 7-oxa-2-azaspiro[3.5]nonanyl, 2-oxa-7-azaspiro[3.5]nonanyl and 2,4,8-triazaspiro[4.5]decanyl.

The term "heteroaryl" as used herein represents aromatic carbocyclic groups of from 5 to 14 carbon atoms having a single ring or multiple condensed rings, wherein one or more of the said carbon atoms have been replaced by one or more heteroatoms selected from oxygen, sulphur and nitrogen. Illustrative heteroaryl groups include furyl, benzofuryl, dibenzofuryl, thienyl, benzothienyl, thieno[2,3-c]pyrazolyl, thieno[3,4-b][1,4]dioxinyl, dibenzothienyl, pyrrolyl, indolyl, 2,3-dihydro-1H-isoindolyl, pyrrolo[2,3-b]pyridinyl, pyrrolo[3,2-c]pyridinyl, pyrrolo[3,4-b]pyridinyl, pyrazolyl, pyrazolo[1,5-a]pyridinyl, pyrazolo[3,4-d]pyrimidinyl, indazolyl, 4,5,6,7-tetrahydroindazolyl, oxazolyl, benzoxazolyl, isoxazolyl, thiazolyl, benzothiazolyl, isothiazolyl, imidazolyl, benzimidazolyl, imidazo[2,1-b]thiazolyl, imidazo[1,2-a]pyridinyl, imidazo[4,5-b]pyridinyl, purinyl, imidazo[1,2-a]pyrimidinyl, imidazo[1,2-a]pyrazinyl, oxadiazolyl, thiadiazolyl, triazolyl, [1,2,4]triazolo[1,5-a]pyrimidinyl, benzotriazolyl, tetrazolyl, pyridinyl, quinolinyl, isoquinolinyl, naphthyridinyl, pyridazinyl, cinnolinyl, phthalazinyl, pyrimidinyl, quinazolinyl, pyrazinyl, quinoxalinyl, pteridinyl, triazinyl and chromenyl groups.

The term "halogen" as used herein is intended to include fluorine, chlorine, bromine and iodine atoms, typically fluorine, chlorine or bromine atoms.

Where the compounds of formula (I) have one or more asymmetric centres, they may accordingly exist as enantiomers. Where the compounds of use in the invention possess two or more asymmetric centres, they may additionally exist as diastereomers. The invention is to be understood to extend to the use of all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise. In addition, compounds of formula (I) may exist as tautomers, for example keto (CH$_2$C=O)↔enol (CH=CHOH) tautomers or amide (NHC=O)↔hydroxyimine (N=COH) tautomers. Formula (I) and the formulae depicted hereinafter are intended to represent all individual tautomers and all possible mixtures thereof, unless stated or shown otherwise.

An illustrative example of a tautomer in accordance with the present invention, is 2-oxo-(1H)-pyridinyl which is a tautomer of 2-hydroxy-pyridinyl.

Another illustrative example of a tautomer in accordance with the present invention, is 2-oxo-(1H)-pyrimidinyl which is a tautomer of 2-hydroxy-pyrimidinyl.

A particular sub-class of compounds in accordance with the present invention is the sub-class of compounds of formula (IA), or an N-oxide thereof, or a pharmaceutically acceptable salt thereof,

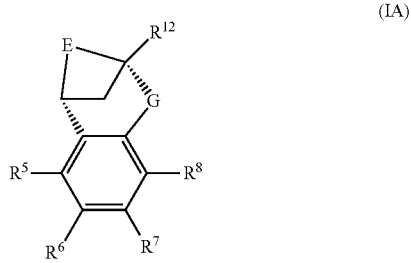

(IA)

wherein E, G, R$^5$, R$^6$, R$^7$ R$^8$ and R$^{12}$ are as defined above.

It is to be understood that each individual atom present in formula (I), or in the formulae depicted hereinafter, may in fact be present in the form of any of its naturally occurring isotopes, with the most abundant isotope(s) being preferred. Thus, by way of example, each individual hydrogen atom present in formula (I), or in the formulae depicted hereinafter, may be present as a $^1$H, $^2$H (deuterium) or $^3$H (tritium) atom, preferably $^1$H. Similarly, by way of example, each individual carbon atom present in formula (I), or in the formulae depicted hereinafter, may be present as a $^{12}$C, $^{13}$C or $^{14}$C atom, preferably $^{12}$C.

Generally, G- represents —O—C(O)—N(R$^f$)—, —N(R$^f$)—C(O)—N(R$^f$) or —N(R$^f$)—S(O)$_2$—N(R$^f$)—; or -G- represents —N(R$^f$)—C(O)—CH$_2$—, CH$_2$—N(R$^f$)—C(O)—, —C(O)—N(R$^f$)—CH$_2$—, —N(R$^g$)—CH$_2$—CH$_2$—, —S(O)$_2$—N(R$^f$)—CH$_2$—, —N(R$^f$)—S(O)$_2$—CH$_2$—, —O—CH$_2$—CH$_2$—, —S—CH$_2$—CH$_2$—, —S(O)—CH$_2$—CH$_2$—, —S(O)$_2$—CH$_2$—CH$_2$—, —S(O)(N—R$^f$)—CH$_2$—CH$_2$—, —O—C(O)—CH$_2$—, —O—S(O)$_2$—N(R$^f$)—, —N(Rf)—C(O)—O—CH$_2$, or —N(R$^f$)—C=N(R$^f$)—CH$_2$.

In a first embodiment, -G- represents —O—C(O)—N(R$^f$)—. In a second embodiment, -G- represents —N(R$^f$)—C(O)—N(R$^f$)—. In a third embodiment, -G- represents —N(R$^f$)—S(O)$_2$—N(R$^f$). In a fourth embodiment, -G- represents optionally substituted —N(R$^f$)—CO—CH$_2$—. In a fifth embodiment, -G- represents optionally substituted —CH$_2$—N(R$^f$)—C(O)—. In a sixth, embodiment, -G- represents optionally substituted —C(O)—N(R$^f$)—CH$_2$—. In a seventh embodiment, -G- represents optionally substituted —N(R$^f$)—CH$_2$—CH$_2$—. In a eighth embodiment, -G- represents optionally substituted —S(O)$_2$—N(R$^f$)—CH$_2$—. In a ninth embodiment, -G- represents optionally substituted —N(R$^f$)—S(O)$_2$—CH$_2$—. In a tenth embodiment, -G- represents optionally substituted —O—CH$_2$—CH$_2$—. In an eleventh embodiment, -G- represents optionally substituted —S—CH$_2$—CH$_2$—. In a twelfth embodiment, -G- represents optionally substituted —S(O)—CH$_2$—CH$_2$. In a thirteenth embodiment, -G- represents optionally substituted —S(O)$_2$—CH$_2$—CH$_2$—. In a fourteenth embodiment, -G- represents optionally substituted —S(O)(N—Rf)—CH$_2$—CH$_2$—. In a fifteenth embodiment, -G- represents optionally substituted —O—C(O)—CH$_2$—. In a sixteenth embodiment, -G- represents optionally substituted —O—S(O)$_2$—N(R$^f$)—. In a seventeenth embodiment, -G- represents optionally substituted —N(R$^f$)—C(O)—O—CH$_2$—. In an eighteenth embodiment, -G- represents optionally substituted —N(R$^f$)—C=N(R$^f$)—CH$_2$.

Typical substituents on -G- include halogen, (C$_{1-6}$)alkyl, hydroxy(C$_{1-6}$)alkyl, trifluoromethyl, carboxy, (C$_{2-6}$)alkylcarbonyl and (C$_{2-6}$)alkoxycarbonyl.

Particular examples of substituents on -G- include fluoro, methyl, carboxy, trifluoromethyl, methylcarbonyl, deuterated methyl, ethoxycarbonyl, hydroxyisopropyl, and hydroxymethyl.

Typically, -G- represents —O—C(O)—N(R$^f$)—, —N(R$^f$)—C(O)—N(R$^f$) or —N(R$^f$)—S(O)$_2$—N(R$^f$)—; or -G- represents —N(R$^f$)—C(O)—CH$_2$—, CH$_2$—N(R$^f$)—C(O)—, —C(O)—N(R$^f$)—CH$_2$—, —N(R$^g$)—CH$_2$—CH$_2$—, —S(O)$_2$—N(R$^f$)—CH$_2$—, —N(R$^f$)—S(O)$_2$—CH$_2$—, —O—CH$_2$—CH$_2$—, —S—CH$_2$—CH$_2$—, —S(O)—CH$_2$—CH$_2$—, —S(O)$_2$—CH$_2$—CH$_2$—, —S(O)(N—R$^f$)—CH$_2$—CH$_2$—, —O—C(O)—CH$_2$—, or —O—S(O)$_2$—N(R$^f$)—.

Suitably, -G- represents —N(R$^f$)—C(O)—CH$_2$—, CH$_2$—N(R$^f$)—C(O)—, —C(O)—N(R$^f$)—CH$_2$—, —N(R$^g$)—CH$_2$—CH$_2$—, —S(O)$_2$—N(R$^f$)—CH$_2$—, —N(R$^f$)—S(O)$_2$—CH$_2$—, —O—CH$_2$—CH$_2$—, —S—CH$_2$—CH$_2$—, —S(O)—CH$_2$—CH$_2$—, —S(O)$_2$—CH$_2$—CH$_2$ or S(O)(N—R$^f$)—CH$_2$—CH$_2$—.

Illustratively, -G- represents —N(R$^f$)—C(O)—CH$_2$— or —N(R$^f$)—CH$_2$—CH$_2$—.

Generally, E represents a fused heteroaromatic ring system of formula (Ea) or a fused heteroaromatic ring system of formula (Eb).

Illustratively, E represents a fused heteroaromatic ring system of formula (Ea).

In a first embodiment according to the present invention, E represents a fused heteroaromatic ring system of formula (Ea).

In a second embodiment according to the present invention, E represents a fused heteroaromatic ring system of formula (Eb).

In a third embodiment according to the present invention, E represents a fused heteroaromatic ring system of formula (Ec).

Particular sub-classes of compounds in accordance with the present invention include compounds of formula (IB), (IC), and (ID).

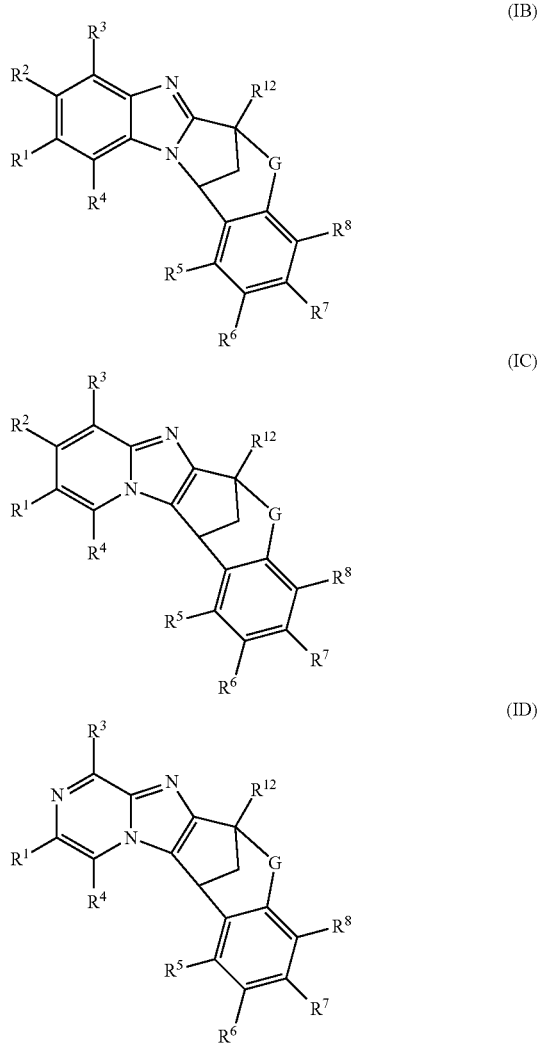

wherein -G-, $R^1$, $R^2$, $R^3$, $R^4$, $R^5$, $R^6$, $R^7$, $R^8$ and $R^{12}$ are as defined above.

Particular sub-classes of compounds in accordance with the present invention include compounds of formula (IB) and (IC), wherein -G-, $R^1$, $R^2$, $R^3$, $R^4$, $R^5$, $R^6$, $R^7$, $R^8$ and $R^{12}$ are as defined above.

A particular sub-class of compounds in accordance with the present invention is the sub-class of compounds of formula (IB), wherein -G-, $R^1$, $R^2$, $R^3$, $R^4$, $R^5$, $R^6$, $R^7$, $R^8$ and $R^{12}$ are as defined above.

Generally, $R^1$ represents hydrogen, halogen, or cyano; or $R^1$ represents $C_{3-7}$ heterocycloalkyl, $(C_{3-7})$heterocycloalkenyl, aryl, heteroaryl, heteroaryl-aryl, $(C_{3-7})$cycloalkyl-heteroaryl, $(C_{3-7})$heterocycloalkyl-heteroaryl, $(C_{4-9})$bicycloalkyl-heteroaryl, $(C_{4-9})$heterobicycloalkyl-heteroaryl- or $(C_{4-9})$spiroheterocycloalkyl-heteroaryl, any of which groups may be optionally substituted by one or more substituents.

Typically, $R^1$ represents halogen; or $R^1$ represents $C_{3-7}$ heterocycloalkyl, aryl, heteroaryl, $(C_{3-7})$cycloalkyl-heteroaryl or $(C_{3-7})$heterocycloalkyl-heteroaryl, any of which groups may be optionally substituted by one or more substituents.

More typically, $R^1$ represents $C_{3-7}$ heterocycloalkyl, heteroaryl, $(C_{3-7})$cycloalkyl-heteroaryl or $(C_{3-7})$heterocycloalkyl-heteroaryl, any of which groups may be optionally substituted by one or more substituents.

Illustratively, $R^1$ represents heteroaryl, which group may be optionally substituted by one or more substituents.

In a first embodiment, $R^1$ represents hydrogen.

In a second embodiment, $R^1$ represents halogen. In one aspect of that embodiment, $R^1$ represents bromo. In another aspect of that embodiment, $R^1$ represents chloro.

In a third embodiment, $R^1$ represents cyano.

In a fourth embodiment, $R^1$ represents optionally substituted aryl. In one aspect of that embodiment, $R^1$ represents optionally substituted phenyl.

In fifth embodiment, $R^1$ represents optionally substituted $C_{3-7}$ heterocycloalkyl. In one aspect of that embodiment, $R^1$ represents optionally substituted azetidinyl. In another aspect of this embodiment, $R^1$ represents optionally substituted piperidinyl.

In a sixth embodiment, $R^1$ represents optionally substituted heteroaryl. In one aspect of that embodiment, $R^1$ represents optionally substituted pyrimidinyl. In another aspect of that embodiment, $R^1$ represents optionally substituted pyridinyl.

In a seventh embodiment, $R^1$ represents optionally substituted $(C_{3-7})$cycloalkyl-heteroaryl-. In a first aspect of that embodiment, $R^1$ represents optionally substituted cyclohexylpyrazolyl-. In a second aspect of that embodiment, $R^1$ represents optionally substituted cyclobutylpyridinyl-. In a third aspect of that embodiment, $R^1$ represents optionally substituted cyclopentylpyridinyl-. In a fourth aspect of that embodiment, $R^1$ represents optionally substituted cyclohexylpyridinyl-. In a fifth aspect of that embodiment, $R^1$ represents optionally substituted cyclopropylpyrimidinyl-. In a sixth aspect of that embodiment, $R^1$ represents optionally substituted cyclobutylpyrimidinyl-. In a seventh aspect of that embodiment, $R^1$ represents optionally substituted cyclopentylpyrimidinyl-. In an eighth aspect of that embodiment, $R^1$ represents optionally substituted cyclohexylpyrimidinyl-. In a ninth aspect of that embodiment, $R^1$ represents optionally substituted cyclohexylpyrazinyl-. In a tenth aspect of that embodiment, $R^1$ represents optionally substituted cyclopropylpyridinyl-.

In an eighth embodiment, $R^1$ represents optionally substituted $(C_{3-7})$-heterocycloalkyl-heteroaryl-. In a first aspect of that embodiment, $R^1$ represents optionally substituted pyrrolidinylpyridinyl-. In a second aspect of that embodiment, $R^1$ represents optionally substituted tetrahydropyranylpyridinyl-. In a third aspect of that embodiment, $R^1$ represents optionally substituted piperidinylpyridinyl-. In a fourth aspect of that embodiment, $R^1$ represents optionally substituted piperazinylpyridinyl-. In a fifth aspect of that embodiment, $R^1$ represents optionally substituted morpholinylpyridinyl-. In a sixth aspect of that embodiment, $R^1$ represents optionally substituted thiomorpholinylpyridinyl-. In a seventh aspect of that embodiment, $R^1$ represents optionally substituted diazepanylpyridinyl-. In an eighth aspect of that embodiment, $R^1$ represents optionally substituted oxetanylpyrimidinyl-. In a ninth aspect of that embodiment, $R^1$ represents optionally substituted azetidinylpyrimidinyl-. In a tenth aspect of that embodiment, $R^1$ represents optionally substituted tetrahydrofuranylpyrimidinyl-. In an eleventh aspect of that embodiment, $R^1$ represents optionally substituted pyrrolidinylpyrimidinyl-. In a twelfth aspect of that embodiment, $R^1$ represents optionally substituted tetrahydropyranyl-pyrimidinyl-. In a thirteenth aspect of that embodiment, $R^1$ represents optionally substituted piperidinylpyrimidinyl-. In a fourteenth aspect of that embodiment, $R^1$ represents optionally substituted piperazinylpyrimidinyl-. In a fifteenth aspect of that embodiment, $R^1$ represents optionally substituted morpholinylpyrimidinyl-. In a sixteenth aspect of that embodiment, $R^1$ represents optionally substituted thiomorpholinylpyrimidinyl-. In a seventeenth aspect of that embodiment, $R^1$ represents optionally substituted azepanylpyrimidinyl-. In an eighteenth aspect of that embodiment, $R^1$ represents optionally substituted oxazepanylpyrimidinyl-. In a nineteenth aspect of that embodiment, $R^1$ represents optionally substituted diazepanylpyrimidinyl-. In a twentieth aspect of that embodiment, $R^1$ represents optionally substituted thiadiazepanyl-pyrimidinyl-. In a twenty-first aspect of that embodiment, $R^1$ represents optionally substituted oxetanylpyrazinyl-. In a twenty-second aspect of that embodiment, $R^1$ represents optionally substituted piperidinylpyrazinyl-. In a twenty-third aspect of that embodiment, $R^1$ represents optionally substituted tetrahydropyranylpyridinyl-. In twenty-third aspect of that embodiment, $R^1$ represents optionally substituted (imino)(oxo)thiazinanylpyrimidinyl-. In twenty-fourth aspect of that embodiment, $R^1$ represents optionally substituted (oxo)thiazinanylpyrimidinyl-. In twenty-fifth aspect of that embodiment $R^1$ represents optionally substituted (dioxo)thiazinanylpyrimidinyl-. In a twenty-sixth aspect of that embodiment, $R^1$ represents optionally substituted (dioxo)tetrahydrothiophenylpyrimidinyl-. In a twenty-seventh aspect of that embodiment, $R^1$ represents optionally substituted tetrahydrothiophenyl-pyrimidinyl-. In a twenty-eighth aspect of that embodiment, $R^1$ represents optionally substituted (dioxo)thiomorpholinyl-pyrimidinyl-. In a twenty-ninth aspect of that embodiment, $R^1$ represents optionally substituted azetidinylpyrazolyl-. In a thirtieth aspect of that embodiment, $R^1$ represents optionally substituted (oxo)tetrahydrothiophenylpyrimidinyl-. In a thirty-first aspect, $R^1$ represents optionally substituted (oxo)thiomorpholinyl-.

In a ninth embodiment, $R^1$ represents optionally substituted $(C_{4-9})$bicycloalkyl-heteroaryl-.

In a tenth embodiment, $R^1$ represents optionally substituted $(C_{4-9})$-heterobicycloalkyl-heteroaryl-. In one aspect of that embodiment, $R^1$ represents optionally substituted (3,7-dioxa-9-azabicyclo[3.3.1]non-9-yl)-pyrimidinyl-. In a second aspect of this embodiment, $R^1$ represents optionally substituted (2-oxa-5-azabicyclo[2.2.1]heptanyl)-pyrimidinyl-. In a third aspect of that embodiment, $R^1$ represents optionally substituted (3-oxa-8-azabicyclo[3.2.1]oct-8-yl)-pyrimidinyl-. In a fourth aspect of that embodiment, $R^1$ represents optionally substituted (3,6-diazabicyclo[3.2.2]nonanyl)-pyrimidinyl-.

In an eleventh embodiment, $R^1$ represents optionally substituted $(C_{4-9})$-spiroheterocycloalkyl-heteroaryl-.

In a twelfth embodiment, $R^1$ represents optionally substituted $(C_{3-7})$heterocycloalkenyl. In one aspect of that embodiment, $R^1$ represents optionally substituted 1,2-dihydropyridinyl. In a second aspect of that embodiment, $R^1$ represents optionally substituted 1,2-dihydropyrimidinyl.

In a thirteenth embodiment, $R^1$ represents optionally substituted heteroaryl-aryl. In one aspect of that embodiment, $R^1$ represents optionally substituted imidazolyl-phenyl.

Suitably, $R^1$ represents hydrogen, chloro or cyano; or $R^1$ represents azetidinyl, piperidinyl, 1,2-dihydropyridinyl,1,2-dihydropyrimidinyl, phenyl, pyridinyl, pyrimidinyl, imidazolylphenyl, cyclohexylpyrazolyl, cyclohexylpyridinyl, cyclopropylpyrimidinyl, cyclobutylpyrimidinyl, cyclopentylpyrimidinyl, cyclohexylpyrimidinyl, cyclohexyl-pyrazinyl, cyclopropylpyridinyl, pyrrolidinylpyridinyl, tetrahydropyranylpyridinyl, piperidinylpyridinyl, piperazinylpyridinyl, morpholinylpyridinyl, thiomorpholinyl-pyridinyl, diazepanylpyridinyl, oxetanylpyrimidinyl, azetidinylpyrimidinyl, tetrahydrofuranylpyrimidinyl, pyrrolidinylpyrimidinyl, tetrahydropyranylpyrimidinyl, pip eridinylpyrimidinyl, pip erazinylpyrimidinyl, morpholinylpyrimidinyl, thiomorpholinyl-pyrimidinyl, azepanylpyrimidinyl, oxazepanylpyrimidinyl, diazepanylpyrimidinyl, thiadiazepanyl-pyrimidinyl, oxetanylpyrazinyl, piperidinylpyrazinyl, tetrahydropyranylpyridinyl, (imino)(oxo)thiazinanyl-pyrimidinyl, (oxo)thiazinanyl-pyrimidinyl, (dioxo)thiazinanyl-pyrimidinyl, (dioxo)tetrahydrothiophenyl-pyrimidinyl, tetrahydrothiophenyl-pyrimidinyl, (dioxo)thiomorpholinyl-pyrimidinyl, (oxo)tetrahydrothiophenyl-pyrimidinyl, (oxo)thiomorpholinyl, (3,7-dioxa-9-azabicyclo[3.3.1]non-9-yl)-pyrimidinyl, (2-oxa-5-azabicyclo[2.2.1]heptanyl)-pyrimidinyl, (3-oxa-8-azabicyclo[3.2.1]oct-8-yl)-pyrimidinyl, or (3,6-diazabicyclo[3.2.2]nonanyl)-pyrimidinyl, any of which groups may be optionally substituted by one or more substituents.

More suitably, $R^1$ represents chloro; or $R^1$ represents azetidinyl, piperidinyl, pyridinyl, pyrimidinyl, cyclobutylpyrimidinyl, cyclopentylpyrimidinyl, cyclohexylpyrimidinyl, oxetanylpyrimidinyl, tetrahydrofuranylpyrimidinyl, pyrrolidinylpyrimidinyl, tetrahydropyranylpyrimidinyl, morpholinylpyrimidinyl, (dioxo)thiazinanyl-pyrimidinyl and (dioxo)tetrahydrothiophenyl-pyrimidinyl any of which groups may be optionally substituted by one or more substituents.

Illustratively, $R^1$ represents pyrimidinyl, which may be optionally substituted by one or more substituents.

Typical examples of optional substituents on $R^1$ include one, two or three substituents independently selected from halogen, halo$(C_{1-6})$alkyl, cyano, cyano$(C_{1-6})$alkyl, nitro $(C_{1-6})$alkyl, $C_{1-6}$ alkyl, phosphate$(C_{1-6})$alkyl, $(C_{3-7})$cycloalkyl, $(C_{3-7})$heterocycloalkyl, difluoromethyl, trifluoromethyl, trifluoroethyl, $C_{2-6}$ alkenyl, hydroxy, hydroxy$(C_{1-6})$alkyl, $C_{1-6}$ alkoxy, $(C_{1-6})$ alkoxy$(C_{1-6})$alkyl, trifluoroethoxy, carboxy$(C_{3-7})$cycloalkyloxy, $C_{1-6}$ alkylthio, $C_{1-6}$ alkylsulphonyl, $(C_{1-6})$alkylsulphonyl$(C_{1-6})$alkyl, oxo, amino, amino-$(C_{1-6})$alkyl, $C_{1-6}$ alkylamino, di$(C_{1-6})$alkylamino, di$(C_{1-6})$alkylamino $(C_{1-6})$alkyl, di$(C_{1-6})$alkenylamino $(C_{1-6})$alkyl, $(C_{1-6})$alkoxy$(C_{1-6})$alkylamino, N—[$(C_{1-6})$alkyl]-N-[hydroxy$(C_{1-6})$alkyl]amino, $(C_{2-6})$alkylcarbonylamino $(C_{1-6})$alkyl, $(C_{2-6})$ alkoxycarbonyl-amino-$C_{1-6}$ alkyl, $(C_{1-6})$ alkylsulphinylamino, $C_{1-6}$ alkylsulphonylamino, $C_{1-6}$ alkylsulphonylamino-$C_{1-6}$ alkyl, N—[$(C_{1-6})$alkyl]-N—[$(C_{1-6})$alkylsulphonyl]amino, bis[$(C_{1-6})$alkyl-sulphonyl]amino, N—[$(C_{1-6})$alkyl]-N-[carboxy$(C_{1-6})$alkyl]amino, carboxy $(C_{3-7})$cycloalkyl-amino, carboxy$(C_{3-7})$cycloalkyl$(C_{1-6})$alkylamino, formyl, $C_{2-6}$ alkylcarbonyl, $(C_{2-6})$alkyl-carbonyloxy $(C_{1-6})$alkyl, carboxy, carboxy$(C_{1-6})$alkyl, $C_{2-6}$ alkoxycarbonyl, $C_{2-6}$ alkoxycarbonyl$(C_{1-6})$alkyl, morpholinyl($C_{1-6}$)alkoxycarbonyl, $C_{2-6}$ alkoxycarbonyl-methylidenyl, aminocarbonyl, aminosulphonyl, ($C_{1-6}$)alkylsulphoximinyl and [($C_{1-6}$)alkyl][N—($C_{1-6}$)alkyl]sulphoximinyl.

Particular examples of optional substituents on $R^1$ include one, two or three substituents independently selected from hydroxy, amino, ($C_{1-6}$)alkyl, (amino)($C_{1-6}$)alkyl, and (hydroxy)($C_{1-6}$) alkyl.

Illustrative examples of particular examples of optional substituents on $R^1$ include one, two or three substituents selected from (hydroxy)($C_{1-6}$) alkyl.

Typical examples of particular substituents on $R^1$ include one, two or three substituents independently selected from fluoro, chloro, fluoromethyl, fluoroisopropyl, cyano, cyanoethyl, cyanoisopropyl, nitromethyl, methyl, ethyl, isopropyl, isopropylmethyl, cyclopropyl, cyclobutyl, difluoromethyl, trifluoromethyl, trifluoroethyl, ethenyl, hydroxy, hydroxymethyl, hydroxyisopropyl, hydroxyisobutyl, methoxy, isopropoxy, methoxyisopropyl, trifluoro-ethoxy, carboxycyclobutyloxy, methylthio, methylsulphonyl, methylsulphonylmethyl, methylsulphonylethyl, oxo, amino, aminomethyl, aminoisopropyl, methylamino, dimethylamino, dimethylaminoisopropyl, di(propenyl)aminoisopropyl, methoxyethylamino, N-(hydroxyethyl)-N-(methyl) amino, acetylaminomethyl, methylsulphonylamino, N-methyl-N-(methylsulphonyl)amino, methylsulphonylaminoisopropyl, bis(methylsulphonyl)amino, N-(carboxyethyl)-N-(methyl)amino, carboxycyclopentylamino, carboxycyclopropylmethylamino, (tert-butyl)sulphinylamino, methylsulphonylaminoisopropyl, formyl, acetyl, acetoxyisopropyl, carboxy, carboxymethyl, carboxyethyl, methoxycarbonyl, ethoxycarbonyl, n-butoxycarbonyl, tert-butoxycarbonyl, methoxycarbonylmethyl, ethoxy-carbonylmethyl, ethoxycarbonylethyl, morpholinylethoxycarbonyl, ethoxycarbonyl-methylidenyl, methylsulphonylaminocarbonyl, acetylaminosulphonyl, methoxyamino-carbonyl, tetrahydrofuranyl, tetrazolyl, tetrazolylmethyl, hydroxyoxadiazolyl, aminocarbonyl, amino-sulphonyl, methylsulphoximinyl and (methyl)(N-methyl)sulphoximinyl.

Illustrative examples of optional substituents on $R^1$ include one, two or three substituents independently selected from amino, hydroxy, methyl, hydroxyisopropyl, aminoisopropyl.

In a particular embodiment, $R^1$ is substituted by hydroxy ($C_{1-6}$)alkyl. In one aspect of that embodiment, $R^1$ is substituted by hydroxyisopropyl. In a particular aspect of that embodiment, $R^1$ is substituted by 2-hydroxyprop-2-yl.

Illustrative values of $R^1$ include chloro, cyano, methylsulphonylphenyl, methylsulphoximinylphenyl, hydroxyisopropypiperidinyl, (dihydroxy)(methyl)cyclobutylpyrimidinyl, hydroxyisopropylpyridinyl, hydroxyisopropyl-pyrimidinyl, (methyl)(hydroxyisopropyl)pyrimidinyl, methoxypyridinyl, methoxyisopropylpyrimidinyl, 2-oxo-pyridin-(1H)-yl, (tert-butoxycarbonyl)aminoisopropyl-pyrimidinyl, aminoisopropylpyrimidinyl, (3,7-dioxa-9-azabicyclo[3.3.1]non-9-yl)-pyrimidinyl, (hydroxy)(trifluoromethyl)azetidinyl-pyrimidinyl, (methylsulphonyl)(methyl)phenyl, (methyl)(hydroxyisopropyl)pyridinyl, [hydroxy)(trifluoromethyl)azetidinyl](methyl)pyrimidinyl methylsulphonylcyclopropylpyridinyl, (dimethyl)(hydroxyisopropyl)pyrimidinyl, (hydroxyisopropyl)(trifluoromethyl)pyrimidinyl, (tert-butoxycarbonyl)(hydroxy)pyrrolidine-pyridinyl, (hydroxy)pyrrolidine-pyridinyl, (methoxycarbonyl)aminoisopropyl-pyrimidinyl, piperazinylpyridinyl, (methylsulphonyl)piperazinyl-pyridinyl, (dimethylamino)isopropylpyrimidinyl, (oxo)piperazinylpyrimidinyl, (N-methyl)pyrazolyl, (methylthio)(methyl)phenyl, morpholinylpyrimidinyl, (methyl)morpholinylpyrimidinyl, ((tert-butyl)sulphinylamino)cyclobutylpyridinyl, (amino)cyclobutylpyridinyl, aminocyclobutylpyrimidinyl, ((tert-butyl)sulphinylamino)oxetanylpyridinyl, (amino)oxetanylpyridinyl, ((tert-butyl)sulphonylamino)oxetanylpyridinyl, pyrrolidinylpyridinyl, (dimethyl)imidazolylphenyl, (methylsulphonyl)aminoisopropylpyrimidinyl, methylcarbonylaminoisopropylpyrimidinyl, pyrrolidinyl-phenyl, (oxo)diazepanylpyrimidinyl, (hydroxy)(methyl)azetidinyl-pyrimidinyl, thiomorpholinylpyrimidinyl, (oxo)thiomorpholinylpyrimidinyl, (dioxo)thiomorpholinylpyrimidinyl, (difluoro)(hydroxy)cyclohexylpyrimidinyl, (difluoro)(amino)cyclohexylpyrimidinyl, (hydroxy)(oxo)tetrahydrothiophenyl-pyrimidinyl, (hydroxy)(dioxo)tetrahydrothiophenyl-pyrimidinyl, (amino)(dioxo)tetrahydrothiophenyl-pyrimidinyl, (hydroxy)tetrahydrothiophenyl-pyrimidinyl, (hydroxy)oxetanylpyrimidinyl, (amino)oxetanylpyrimidinyl, (methylsulphonyl)azetidinyl-2,5-pyrazolyl, (oxo)(methyl)-1,2-dihydropyridinyl, (oxo)-1,2-dihydropyrimidinyl, (dihydroxy)(methyl)cyclohexylpyrimidinyl, cyanoisopropylpyrimidinyl, (cyano)(methyl)azetidinylpyrimidinyl, (2-oxa-5-azabicyclo[2.2.1]heptanyl)-pyrimidinyl-, (3-oxa-8-azabicyclo[3.2.1]oct-8-yl)-pyrimidinyl-, (oxo)(3,6-diazabicyclo[3.2.2]nonanyl)-pyrimidinyl-, (hydroxyisopropyl)azetidinyl, (difluoro)azetidinylpyrimidinyl, tetrahydropyranylpyrimidinyl, (amino)tetrahydropyranylpyrimidinyl, (amino)tetrahydrofuranylpyrimidinyl, (methyl)tetrahydropyranylpyrimidinyl, methylsulphoxyminylpyridinyl, (difluoromethyl)(hydroxyisopropyl)pyrimidinyl, (tetrahydrofuranyl)(hydroxyisopropyl)pyrimidinyl, di(propenyl)aminoisopropylpyrimidinyl, sulphate-isopropylpyrimidinyl, carboxyethyl-carbonyloxy-isopropyl-pyrimidinyl, (hydroxy)isobutylpyrimidinyl (cyano)(amino)cyclobutylpyrimidinyl, (difluoromethyl)(amino)cyclobutylpyrimidinyl, (amino)cyclobutylpyrimidinyl, (amino)cylopentylpyrimidinyl, (dioxo)thiazinanylpyrimidinyl, (methyl)(dioxo)thiazinanylpyrimidinyl, (methyl)pyrrolidinylpyrimidinyl and pyrrolidinylpyrimidinyl.

Specific values of $R^1$ include chloro, methylsulphonylphenyl, methylsulphoximinyl-phenyl, (dihydroxy)(methyl)cyclobutylpyrimidinyl, (amino)oxetanylpyrimidinyl, (difluoro)(amino)cyclohexylpyrimidinyl, (methyl)morpholinylpyrimidinyl, (amino)(dioxo)tetrahydrothiophenyl-pyrimidinyl, (amino)tetrahydropyranylpyrimidinyl, (amino)tetrahydrofuranylpyrimidinyl, hydroxyisopropylpyridinyl, hydroxyisopropylpyrimidinyl, (methyl)(hydroxyisopropyl)pyrimidinyl, phosphate-isopropylpyrimidinyl, methoxypyridinyl, methoxyisopropylpyrimidinyl, 2-oxo-pyridin-(1H)-yl, (tert-butoxycarbonyl)aminoisopropyl-pyrimidinyl, aminoisopropylpyrimidinyl, (3,7-dioxa-9-azabicyclo[3.3.1]non-9-yl)-pyrimidinyl, (hydroxy)(trifluoromethyl)azetidinyl-pyrimidinyl, (methylsulphonyl)(methyl)phenyl, (methyl)(hydroxyisopropyl)pyridinyl, (cyano)(amino)cyclobutylpyrimidinyl, (difluoromethyl)(amino)cyclobutylpyrimidinyl, (amino)cyclobutylpyrimidinyl, (amino)cylopentylpyrimidinyl, (dioxo)thiazinanylpyrimidinyl, (methyl)(dioxo)thiazinanylpyrimidinyl, (methyl)pyrrolidinylpyrimidinyl and pyrrolidinylpyrimidinyl.

Particular values of $R^1$ include hydroxyisopropylpiperidinyl, (dihydroxy)(methyl)cyclobutylpyrimidinyl, hydroxyisopropylpyrimidinyl, aminoisopropylpyrimidinyl, amino cyclobutylpyrimidinyl, (methyl)morpholinylpyrimidinyl, (methyl)tetrahydropyranylpyrimidinyl, (amino)tetrahydrofuranylpyrimidinyl, (amino)tetrahydropyranylpyrimidinyl, and (amino)oxetanylpyrimidinyl, (amino)oxetanylpyrimidinyl, (difluoro)(amino)cyclohexylpyrimidinyl, (methyl)morpholinylpyrimidinyl, (amino)(dioxo)tetrahydrothiophenylpyrimidinyl, (amino)tetrahydropyranylpyrimidinyl, (amino) tetrahydrofuranylpyrimidinyl, (cyano)(amino)cyclobutylpyrimidinyl, (difluoromethyl)(amino)cyclobutylpyrimidinyl, (amino)cyclobutylpyrimidinyl, (amino)cylopentylpyrimidinyl, (dioxo)thiazinanylpyrimidinyl, (methyl)(dioxo)thiazinanylpyrimidinyl, (methyl)pyrrolidinylpyrimidinyl and pyrrolidinylpyrimidinyl.

Illustrative values of $R^1$ include hydroxyisopropylpyrimidinyl, particularly 2-(2-hydroxy-propan-2-yl)-pyrimidin-5-yl.

Typically, $R^2$ represents hydrogen, halogen, trifluoromethyl, trifluoromethoxy or —$OR^a$; or $C_{1-6}$ alkyl optionally substituted by one or more substituents.

Suitably, $R^2$ represents hydrogen or halogen.

Illustrative values of $R^2$ include hydrogen.

In a first embodiment, $R^2$ represents hydrogen. In a second embodiment, $R^2$ represents halogen. In one aspect of that embodiment, $R^2$ represents fluoro. In another aspect of that embodiment, $R^2$ represents chloro. In a third embodiment, $R^2$ represents cyano. In a fourth embodiment, $R^2$ represents nitro. In a fifth embodiment, $R^2$ represents hydroxy. In a sixth embodiment, $R^2$ represents trifluoromethyl. In a seventh embodiment, $R^2$ represents trifluoromethoxy. In an eighth embodiment, $R^2$ represents —$OR^a$. In a ninth embodiment, $R^2$ represents optionally substituted $C_{1-6}$ alkyl. In a first aspect of that embodiment, $R^2$ represents $C_{1-6}$ alkyl. In a particular aspect of this embodiment, $R^2$ represents methyl. In another particular aspect of this embodiment, $R^2$ represents ethyl. In a second aspect of that embodiment, $R^2$ represents monosubstituted methyl or monosubstituted ethyl.

Typical examples of optional substituents on $R^2$ include $C_{2-6}$ alkoxycarbonyl.

Typical examples of particular substituents on $R^2$ include ethoxycarbonyl.

Typical values of $R^2$ include hydrogen, fluoro, chloro, trifluoromethyl, trifluoromethoxy, —$OR^a$, methyl and ethoxycarbonylethyl.

Suitable values of $R^2$ include hydrogen, bromo and fluoro.

Particular values of $R^2$ include hydrogen and fluoro.

Generally, $R^3$ represents hydrogen, halogen, trifluoromethyl, or $C_{1-6}$ alkyl.

Typically, $R^3$ represents hydrogen, halogen or $C_{1-6}$ alkyl.

In a first embodiment, $R^3$ represents hydrogen. In a second embodiment, $R^3$ represents halogen. In one aspect of that embodiment, $R^3$ represents fluoro. In a third embodiment, $R^3$ represents optionally substituted $C_{1-6}$ alkyl. In one aspect of that embodiment, $R^3$ represents $C_{1-6}$ alkyl. In a particular aspect of this embodiment, $R^3$ represents methyl. In another particular aspect of this embodiment, $R^3$ represents ethyl. In a fourth embodiment, $R^3$ represents trifluoromethyl.

Illustratively, $R^3$ represents hydrogen or trifluoromethyl.

In a particular embodiment, $R^3$ represents hydrogen.

Generally, $R^4$ represents hydrogen, halogen, trifluoromethyl, or $C_{1-6}$ alkyl.

Typically, $R^4$ represents hydrogen, halogen or $C_{1-6}$ alkyl.

In a first embodiment, $R^4$ represents hydrogen. In a second embodiment, $R^4$ represents halogen. In one aspect of that embodiment, $R^4$ represents fluoro. In a third embodiment, $R^4$ represents optionally substituted $C_{1-6}$ alkyl. In one aspect of that embodiment, $R^4$ represents $C_{1-6}$ alkyl. In a particular aspect of this embodiment, $R^4$ represents methyl. In another particular aspect of this embodiment, $R^4$ represents ethyl. In a fourth embodiment, $R^4$ represents trifluoromethyl.

In a particular embodiment, $R^4$ represents hydrogen.

Typically, $R^5$ represents halogen, cyano, difluoromethoxy, trifluoromethoxy, —$OR^a$, or $C_{1-6}$ alkylsulphonyl; or $C_{1-6}$ alkyl optionally substituted by one or more substituents.

Suitably, $R^5$ represents halogen, —$OR^a$, difluoromethoxy or trifluoromethoxy.

In a first embodiment, $R^5$ represents hydrogen. In a second embodiment, $R^5$ represents halogen. In one aspect of that embodiment, $R^5$ represents chloro. In a second aspect of that embodiment, $R^5$ represents fluoro. In a third embodiment, $R^5$ represents cyano. In a fourth embodiment, $R^5$ represents hydroxy. In a fifth embodiment, $R^5$ represents trifluoromethyl. In a sixth embodiment, $R^5$ represents difluoromethoxy. In a seventh embodiment, $R^5$ represents trifluoromethoxy. In an eighth embodiment, $R^5$ represents —$OR^a$. In one aspect of that embodiment, $R^5$ represents methoxy. In a ninth embodiment, $R^5$ represents $C_{1-6}$ alkylsulphonyl. In one aspect of that embodiment, $R^5$ represents methylsulphonyl. In a tenth embodiment, $R^5$ represents optionally substituted $C_{1-6}$ alkyl. In one aspect of that embodiment, $R^5$ represents $C_{1-6}$ alkyl. In a particular aspect of this embodiment, $R^5$ represents methyl. In another particular aspect of this embodiment, $R^5$ represents ethyl.

More suitably, $R^5$ represents fluoro, methoxy, difluoromethoxy or trifluoromethoxy.

Illustratively, $R^5$ represents difluoromethoxy.

Generally, $R^6$ represents hydrogen, halogen or trifluoromethyl.

In a first embodiment, $R^6$ represents hydrogen. In a second embodiment, $R^6$ represents halogen. In one aspect of that embodiment, $R^6$ represents chloro. In a second aspect of that embodiment, $R^6$ represents fluoro. In a third aspect of that embodiment, $R^6$ represents bromo. In a third embodiment, $R^6$ represents trifluoromethyl. In a fourth embodiment, $R^6$ represents $C_{1-6}$ alkyl. In a first aspect of that embodiment, $R^6$ represents $C_{1-4}$ alkyl. In a second aspect of that embodiment $R^6$ represents $C_{1-3}$ alkyl. In a third aspect of that embodiment, $R^6$ represents $C_{1-2}$ alkyl. In a particular aspect of this embodiment, $R^6$ represents methyl. In another particular aspect of this embodiment, $R^6$ represents ethyl. In a fifth embodiment, $R^6$ represents $C_{1-6}$ alkoxy. In a particular aspect of that embodiment, $R^6$ represents methoxy.

Typically, $R^6$ represents hydrogen, bromo or trifluoromethyl.

Suitably, $R^6$ represents hydrogen or bromo.

Illustratively, $R^6$ represents hydrogen.

In a first embodiment, $R^7$ represents hydrogen. In a second embodiment, $R^7$ represents halogen. In one aspect of that embodiment, $R^7$ represents chloro. In a second aspect of that embodiment, $R^7$ represents fluoro. In a third embodiment, $R^7$ represents trifluoromethyl. In a fourth embodiment, $R^7$ represents $C_{1-6}$ alkyl. In a first aspect of that embodiment, $R^7$ represents $C_{1-4}$ alkyl. In a second aspect of that embodiment $R^7$ represents $C_{1-3}$ alkyl. In a third aspect of that embodiment, $R^7$ represents $C_{1-2}$ alkyl. In a particular aspect of this embodiment, $R^7$ represents methyl. In another particular aspect of this embodiment, $R^7$ represents ethyl. In a fifth embodiment, $R^7$ represents $C_{1-6}$ alkoxy. In a particular aspect of that embodiment, $R^7$ represents methoxy.

Suitably, $R^7$ represents hydrogen or trifluoromethyl.

Illustratively, $R^7$ represents hydrogen.

Generally, $R^8$ represents hydrogen, halogen or trifluoromethyl.

In a first embodiment, $R^8$ represents hydrogen. In a second embodiment, $R^8$ represents halogen. In one aspect of that embodiment, $R^8$ represents chloro. In a second aspect of that embodiment, $R^8$ represents fluoro. In a third embodiment, $R^8$ represents cyano. In a fourth embodiment, $R^8$ represents hydroxy. In a fifth embodiment, $R^8$ represents trifluoromethyl. In a sixth embodiment, $R^8$ represents difluoromethoxy. In a seventh embodiment, $R^8$ represents trifluoromethoxy. In an eighth embodiment, $R^8$ represents —$OR^a$. In one aspect of that embodiment, $R^8$ represents methoxy. In a ninth embodiment, $R^8$ represents $C_{1-6}$ alkylsulphonyl. In one aspect of that embodiment, $R^8$ represents methylsulphonyl. In a tenth embodiment, $R^8$ represents optionally substituted $C_{1-6}$ alkyl. In one aspect of that embodiment, $R^8$ represents $C_{1-6}$ alkyl. In a particular aspect of this embodiment, $R^8$ represents methyl. In another particular aspect of this embodiment, $R^8$ represents unsubstituted ethyl. In an eleventh embodiment, $R^8$ represents trifluoromethyl.

Typically, $R^8$ represents hydrogen, chloro or trifluoromethyl

Suitably, $R^8$ represents hydrogen or chloro.

Illustratively, $R^8$ represents hydrogen.

Generally, $R^{12}$ represents hydrogen or $C_{1-6}$ alkyl.

Suitably, $R^{12}$ represents hydrogen or methyl.

Illustratively, $R^{12}$ represents hydrogen.

Generally, $R^a$ represents $C_{1-6}$ alkyl, $C_{3-7}$ cycloalkyl, $C_{3-7}$ heterocycloalkyl, aryl, aryl($C_{1-6}$)alkyl, heteroaryl or heteroaryl($C_{1-6}$)alkyl, any of which groups may be optionally substituted by one or more substituents.

Generally, $R^b$ and $R^c$ independently represent hydrogen or trifluoromethyl; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents; or $R^b$ and $R^c$, when taken together with the nitrogen atom to which they are both attached, represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl, homopiperazin-1-yl, (imino)(oxo)thiazinan-4-yl, (oxo)thiazinan-4-yl or (dioxo)thiazinan-4-yl any of which groups may be optionally substituted by one or more substituents.

Generally, $R^d$ represents hydrogen; or $C_{1-6}$ alkyl, $C_{3-7}$ cycloalkyl, aryl, $C_{3-7}$ heterocycloalkyl or heteroaryl, any of which groups may be optionally substituted by one or more substituents.

Generally, $R^e$ represents $C_{1-6}$ alkyl, aryl or heteroaryl, any of which groups may be optionally substituted by one or more substituents.

Typical examples of suitable substituents which may be present on $R^a$, $R^b$, $R^c$, $R^d$ or $R^e$, or on the heterocyclic moiety —$NR^bR^c$, include halogen, $C_{1-6}$ alkyl, $C_{1-6}$ alkoxy, difluoromethoxy, trifluoromethoxy, $C_{1-6}$ alkoxy($C_{1-6}$)alkyl, $C_{1-6}$ alkylthio, $C_{1-6}$ alkylsulphinyl, $C_{1-6}$ alkylsulphonyl, hydroxy, hydroxy($C_{1-6}$)alkyl, amino($C_{1-6}$)alkyl, cyano, trifluoromethyl, oxo, $C_{2-6}$ alkylcarbonyl, carboxy, $C_{2-6}$ alkoxycarbonyl, $C_{2-6}$ alkylcarbonyloxy, amino, $C_{1-6}$ alkylamino, di($C_{1-6}$)alkylamino, phenylamino, pyridinylamino, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkylsulphonylamino, aminocarbonyl, $C_{1-6}$ alkylaminocarbonyl and di($C_{1-6}$)alkylaminocarbonyl.

Typical examples of specific substituents which may be present on $R^a$, $R^b$, $R^c$, $R^d$, or $R^e$, or on the heterocyclic moiety —$NR^bR^c$, include fluoro, chloro, bromo, methyl, ethyl, isopropyl, methoxy, isopropoxy, difluoromethoxy, trifluoromethoxy, methoxymethyl, methylthio, ethylthio, methylsulphinyl, methylsulphonyl, hydroxy, hydroxymethyl, hydroxyethyl, aminomethyl, cyano, trifluoromethyl, oxo, acetyl, carboxy, methoxycarbonyl, ethoxycarbonyl, tert-butoxycarbonyl, acetoxy, amino, methylamino, ethylamino, dimethylamino, phenylamino, pyridinylamino, acetylamino, tert-butoxycarbonylamino, acetylaminomethyl, methylsulphonylamino, aminocarbonyl, methylaminocarbonyl and dimethylaminocarbonyl.

Suitably, $R^a$ represents $C_{1-6}$ alkyl, aryl($C_{1-6}$)alkyl or heteroaryl($C_{1-6}$)alkyl, any of which groups may be optionally substituted by one or more substituents.

In a first embodiment, $R^a$ represents optionally substituted $C_{1-6}$ alkyl. In a first aspect of that embodiment, $R^a$ represents $C_{1-6}$ alkyl. In a particular aspect of this embodiment, $R^a$ represents methyl. In a second aspect of that embodiment, $R^a$ represents substituted $C_{1-6}$ alkyl. In a particular aspect of this embodiment, $R^a$ represents methoxyethyl. In a second embodiment, $R^a$ represents optionally substituted aryl. In a first aspect of this embodiment, $R^a$ represents aryl. In a particular aspect of this embodiment, $R^a$ represents phenyl. In a second aspect of that embodiment, $R^a$ represents mono-substituted aryl. In a particular aspect of this embodiment, $R^a$ represents methylphenyl. In a third embodiment, $R^a$ represents optionally substituted aryl($C_{1-6}$)alkyl. In one aspect of that embodiment, $R^a$ represents aryl($C_{1-6}$)alkyl. In a particular aspect of this embodiment, $R^a$ represents benzyl. In a fourth embodiment, $R^a$ represents optionally substituted heteroaryl. In one aspect of this embodiment, $R^a$ represents heteroaryl. In a fifth embodiment, $R^a$ represents optionally substituted heteroaryl($C_{1-6}$)alkyl. In a particular aspect of this embodiment, $R^a$ represents dioxoisoindolylpropyl. In a sixth embodiment, $R^a$ represents $C_{3-7}$ cycloalkyl. In a seventh embodiment, $R^a$ represents $C_{3-7}$ heterocycloalkyl.

Appositely, $R^a$ represents $C_{1-6}$ alkyl. Illustratively, $R^a$ represents methyl.

Typically, $R^b$ represents hydrogen; or $C_{1-6}$ alkyl, aryl ($C_{1-6}$)alkyl, $C_{3-7}$ heterocycloalkyl or $C_{3-7}$ heterocycloalkyl ($C_{1-6}$)alkyl, any of which groups may be optionally substituted by one or more substituents.

Suitably, $R^b$ represents hydrogen or $C_{1-6}$ alkyl.

In a first embodiment, $R^b$ represents hydrogen. In a second embodiment, $R^b$ represents $C_{1-6}$ alkyl. In a particular aspect of that embodiment, $R^b$ represents methyl.

Typically $R^c$ represents hydrogen; or $C_{1-6}$ alkyl, $C_{3-7}$ cycloalkyl or $C_{3-7}$ heterocycloalkyl, any of which groups may be optionally substituted by one or more substituents.

Suitably, $R^c$ represents hydrogen or $C_{1-6}$ alkyl.

In a first embodiment, $R^c$ is hydrogen. In a second embodiment, $R^c$ represents $C_{1-6}$ alkyl. In a one aspect of that embodiment, $R^c$ represents methyl. In a another aspect of that embodiment, $R^c$ represents ethyl.

Appositely, $R^c$ represents hydrogen or ethyl.

Alternatively, the moiety —$NR^bR^c$ may suitably represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl or homopiperazin-1-yl, (imino)(oxo)thiazinan-4-yl, (oxo)thiazinan-4-yl or (dioxo)thiazinan-4-yl, any of which groups may be optionally substituted by one or more substituents.

Specific values of the heterocyclic moiety —$NR^bR^c$ include azetidin-1-yl, hydroxyazetidin-1-yl, hydroxymethylazetidin-1-yl, (hydroxy)(hydroxymethyl)azetidin-1-yl, aminomethyl-azetidin-1-yl, cyanoazetidin-1-yl, carboxyazetidin-1-yl, aminoazetidin-1-yl, aminocarbonylazetidin-1-yl, pyrrolidin-1-yl, aminomethylpyrrolidin-1-yl, oxopyrrolidin-1-yl, acetylaminomethylpyrrolidin-1-yl, tert-butoxycarbonylaminopyrrolidin-1-yl, oxo-oxazolidin-3-yl, hydroxyisoxazolidin-2-yl, thiazolidin-3-yl, oxothiazolidin-3-yl, dioxoisothiazolidin-2-yl, piperidin-1-yl, hydroxypiperidin-1-yl, hydroxymethylpiperidin-1-yl, aminopiperidin-1-yl, acetylaminopiperidin-1-yl, tert-butoxycarbonylaminopiperidin-1-yl, methylsulphonylaminopiperidin-1-yl, morpholin-4-yl, piperazin-1-yl, methylpiperazin-1-yl, methylsulphonylpiperazin-1-yl, oxopiperazin-1-yl, acetylpiperazin-1-yl, ethoxycarbonylpiperazin-1-yl, oxohomopiperazin-1-yl, (imino)(oxo)thiazinan-4-yl, (oxo)thiazinan-4-yl, and (dioxo)thiazinan-4-yl.

Typically, $R^d$ represents hydrogen; or $C_{1-6}$ alkyl, aryl or heteroaryl, any of which groups may be optionally substituted by one or more substituents.

Selected examples of suitable substituents on $R^d$ include halogen, $C_{1-6}$ alkyl, $C_{1-6}$ alkoxy, oxo, $C_{2-6}$ alkylcarbonyloxy and di($C_{1-6}$)alkylamino.

Selected examples of particular substituents on $R^d$ include fluoro, methyl, methoxy, oxo, acetoxy and dimethylamino.

Suitably, $R^d$ represents hydrogen or $C_{1-6}$ alkyl.

In a first embodiment, $R^d$ represents hydrogen. In a second embodiment, $R^d$ represents optionally substituted $C_{1-6}$ alkyl. In one aspect of that embodiment, $R^d$ represents $C_{1-6}$ alkyl. In a third embodiment, $R^d$ represents optionally substituted aryl. In one aspect of that embodiment, $R^d$ represents phenyl. In a fourth embodiment, $R^d$ represents optionally substituted heteroaryl.

Appositely, $R^d$ represents hydrogen or methyl.

Typically, $R^e$ represents $C_{1-6}$ alkyl or aryl, either of which groups may be optionally substituted by one or more substituents.

Selected examples of suitable substituents on $R^e$ include $C_{1-6}$ alkyl, especially methyl.

In a first embodiment, $R^e$ represents optionally substituted $C_{1-6}$ alkyl. In a particular aspect of that embodiment, $R^e$ represents $C_{1-6}$ alkyl. In a particular aspect of this embodiment especially methyl. In a second embodiment, $R^e$ represents optionally substituted aryl. In one aspect of that embodiment, $R^e$ represents phenyl. In another aspect of that embodiment, $R^e$ represents monosubstituted aryl.

Suitably, $R^e$ represents methyl, propyl or methylphenyl.

Generally, $R^f$ represents hydrogen; or $C_{1-6}$ alkyl, $C_{3-6}$ cycloalkyl, or $C_{4-6}$ heterocycloalkyl, any of which groups may be optionally substituted by one or more substituents.

Suitably, $R^f$ represents hydrogen; or $C_{1-6}$ alkyl, which group may be optionally substituted by one or more substituents.

Suitable examples of substituents on $R^f$ include halogen and $C_{1-6}$ alkyl.

Particular examples of substituent on $R^f$ include trifluoromethyl, carboxy and hydroxy.

In a first embodiment, $R^f$ represents hydrogen. In a second embodiment, $R^f$ represents optionally substituted $C_{1-6}$ alkyl. In one aspect of that embodiment, $R^f$ represents $C_{1-6}$ alkyl. In a particular aspect of this embodiment, $R^f$ represents methyl. In another particular aspect of this embodiment, $R^f$ represents ethyl. In a further particular aspect of this embodiment, $R^f$ represents isopropyl. In another aspect of that embodiment, $R^f$ represents deuterated methyl. In a further aspect of that embodiment, $R^f$ represents substituted $C_{1-6}$ alkyl. In a third embodiment, $R^f$ represents optionally substituted $C_{3-6}$ cycloalkyl. In one aspect of that embodiment, $R^f$ represents $C_{3-6}$ cycloalkyl.

Particular values of $R^f$ include hydrogen, methyl, ethyl, isopropyl, (carboxy)methyl, (trifluoromethyl)methyl, (hydroxyisopropyl)methyl and deuterated methyl.

Illustrative values of $R^f$ include hydrogen and methyl.

Generally, $R^g$ represents hydrogen; or $C_{1-6}$ alkyl, —CO—($C_{1-6}$)alkyl, —SO$_2$—($C_{1-6}$)alkyl, —CO—($C_{3-7}$)heterocycloalkyl, —SO$_2$—($C_{3-7}$)cycloalkyl, —SO$_2$—($C_{3-7}$)heterocycloalkyl, —SO$_2$-aryl, —SO$_2$-heteroaryl, heteroaryl or ($C_{2-6}$)alkoxycarbonyl, any of which groups may be optionally substituted by one or more substituents.

Typically, $R^g$ represents hydrogen; or $C_{1-6}$ alkyl, —CO—($C_{1-6}$)alkyl, —SO$_2$—($C_{1-6}$)alkyl. —CO—($C_{3-7}$)heterocycloalkyl, —SO$_2$—($C_{3-7}$)cycloalkyl, —SO$_2$-aryl, —SO$_2$-heteroaryl, heteroaryl or ($C_{2-6}$)alkoxycarbonyl, any of which groups may be optionally substituted by one or more substituents.

Suitably, $R^g$ represents hydrogen, optionally substituted $C_{1-6}$ alkyl, —CO—($C_{1-6}$)alkyl or —SO$_2$—($C_{1-6}$)alkyl.

Typically, substituents on $R^g$ include independently halogen, hydroxy, $C_{1-6}$ alkyl, trifluoromethyl, carboxy, ($C_{1-6}$) alkoxy, $C_{1-6}$ alkoxycarbonyl, $C_{4-9}$ heterobicycloalkyl, ($C_{1-6}$ alkyl)sulphonyl and tri($C_{1-6}$ alkyl)silyloxy.

Suitable examples of substituents on $R^g$ include halogen and $C_{1-6}$ alkyl.

Particular examples of substituents on $R^g$ include independently methyl, trifluoromethyl, ethoxycarbonyl, 3,7-dioxa-9-azabicyclo[3.3.1]non-9-yl, methylsulphonyl, (tert-butyl)(di-methyl)silyloxyethyl, hydroxy and methoxy.

In a first embodiment, $R^g$ represents hydrogen. In a second embodiment, $R^g$ represents optionally substituted $C_{1-6}$ alkyl. In one aspect of that embodiment, $R^g$ represents $C_{1-6}$ alkyl. In a particular aspect of this embodiment, $R^g$ represents methyl. In another particular aspect of this embodiment, $R^g$ represents ethyl. In a further particular aspect of this embodiment, $R^g$ represents isopropyl. In a third embodiment, $R^g$ represents optionally substituted $C_{3-6}$ cycloalkyl. In one aspect of that embodiment, $R^g$ represents $C_{3-6}$ cycloalkyl. In a fourth embodiment, $R^g$ represents optionally substituted —CO—($C_{1-6}$)alkyl. In one aspect of that embodiment, $R^g$ represents —CO—($C_{1-6}$)alkyl. In a particular aspect of this embodiment, $R^g$ represents —CO—CH$_3$. In a fifth embodiment, $R^g$ represents optionally substituted —SO$_2$—($C_{1-6}$)alkyl. In one aspect of that embodiment, $R^g$ represents —SO$_2$—($C_{1-6}$)alkyl. In a particular aspect of this embodiment, $R^g$ represents —SO$_2$—CH$_3$. In a sixth embodiment, $R^g$ represents optionally substituted —CO—($C_{3-7}$)heterocycloalkyl. In a particular aspect of that embodiment, $R^g$ represents —CO-azetidinyl. In a seventh embodiment, $R^g$ represents optionally substituted —SO$_2$—($C_{3-7}$)cycloalkyl. In a particular aspect of that embodiment, $R^g$ represents —SO$_2$-cyclopropyl. In an eighth embodiment, $R^g$ represents optionally substituted —SO$_2$—($C_{3-7}$)heterocycloalkyl. In a ninth embodiment, $R^g$ represents optionally substituted —SO$_2$-aryl. In a particular aspect of that embodiment, $R^g$ represents optionally substituted —SO$_2$-phenyl. In a tenth embodiment, $R^g$ represents optionally substituted —SO$_2$-heteroaryl. In a particular aspect of that embodiment, $R^g$ represents optionally substituted —SO$_2$-pyridinyl. In an eleventh embodiment, $R^g$ represents optionally substituted heteroaryl. In a particular aspect of that embodiment, $R^g$ represents optionally substituted pyrimidinyl. In a twelfth embodiment, $R^g$ represents optionally substituted ($C_{2-6}$)alkoxycarbonyl. In a particular aspect of that embodiment, $R^g$ represents ethoxycarbonyl.

Illustrative values of $R^g$ include hydrogen, methyl, carboxymethyl, ethoxycarbonylmethyl, methylcarbonyl, methylsulphonyl, (3,7-dioxa-9-azabicyclo[3.3.1]non-9-yl)methylcarbonyl, azetidinylcarbonyl, (methylsulphonyl)azetidinylcarbonyl, pyridinylsulphonyl, cyclopropylsulphonyl, (tert-butyl)(dimethyl)silyloxyethyl, hydroxyethyl, phenylsulphonyl, (methoxy)pyridinylsulphonyl, (pyridine-2(1H)-one)sulphonyl, pyrimidinyl and ethoxycarbonyl.

Selected values of R$^g$ include hydrogen, methyl, carboxymethyl, ethoxycarbonylmethyl, methylcarbonyl and methylsulphonyl.

Illustrative values of R$^g$ include methylcarbonyl.

A particular sub-group of the compounds of formula (IB) above is represented by the compounds of formula (IIB) and N-oxides thereof, and pharmaceutically acceptable salts thereof:

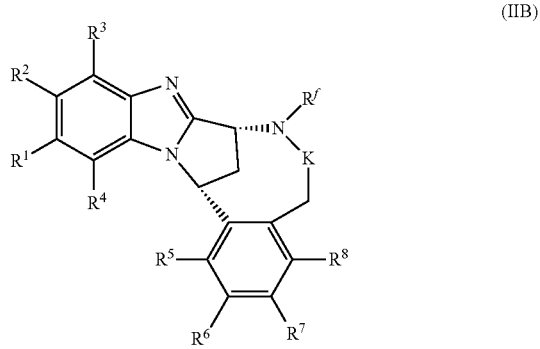

(IIB)

wherein
K represents CH$_2$ or C=O; and
R$^1$, R$^2$, R$^3$, R$^4$, R$^5$, R$^6$, R$^7$, R$^8$ and R$^f$ are as defined above.

In one embodiment, K represents CH$_2$. In another embodiment K represents C=O.

A particular sub-group of compounds of formula (IIB) above is represented by the compounds of formula (IIB-A) and N-oxides thereof, and pharmaceutically acceptable salts thereof:

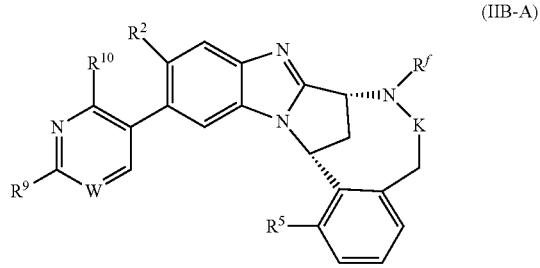

(IIB-A)

wherein,
W represents N, C—H or C—F;
R$^9$ represents hydroxy(C$_{1-6}$)alkyl, (C$_{1-6}$) alkoxy(C$_{1-6}$) alkyl or amino(C$_{1-6}$)alkyl;
R$^{10}$ represents hydrogen or C$_{1-6}$; and
K, R$^2$, R$^5$ and R$^f$ are as defined above.

Generally, W represents N or C—H.
Suitably, W represents N or C—F.
In one embodiment, W represents N. In another embodiment, W represents C—H. In a further embodiment, W represents C—F.

Suitably, R$^9$ represents hydroxy(C$_{1-6}$)alkyl or (C$_{1-6}$) alkoxy(C$_{1-6}$)alkyl.

Suitably, R$^9$ represents hydroxyisopropyl or aminoisopropyl.

Particular values of R$^9$ include 2-hydroxy-prop-2-yl and 2-amino-prop-2-yl.

In one embodiment, R$^9$ represents hydroxyisopropyl. In a particular aspect of that embodiment, R$^9$ represents 2-hydroxy-prop-2-yl.

In another embodiment, R$^9$ represents aminoisopropyl. In a particular aspect of that embodiment, R$^9$ represents 2-amino-prop-2-yl.

In one embodiment, R$^{10}$ represents hydrogen. In another embodiment, R$^{10}$ represents C$_{1-6}$ alkyl. In a particular aspect of this embodiment, R$^{10}$ represents methyl.

Illustratively, R$^{10}$ represents hydrogen or methyl.
Particularly, R$^{10}$ represents hydrogen.

Another subset of the compounds of formula (IIB) above is represented by the compounds of formula (IIB-B) and N-oxides thereof, and pharmaceutically acceptable salts thereof,

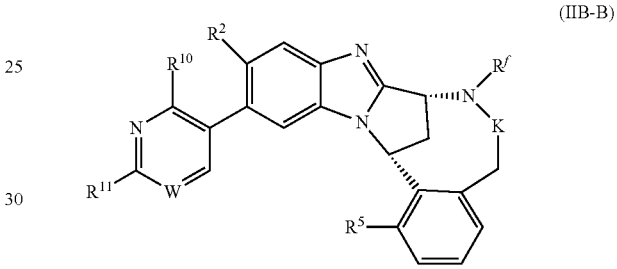

(IIB-B)

wherein
R$^{11}$ represents a group of formula (a), (b), (c), (d), (e), (f) or (g):

(a)

(b)

(c)

(d)

(e)

-continued

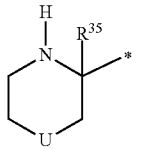
(f)

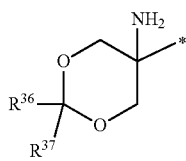
(g)

in which the asterisk (*) represents the site of attachment to the remainder of the molecule;

U represents O, S, S(O), S(O)$_2$, S(O)(NR$^b$), N(R$^{31}$) or C(R$^{32}$)(R$^{33}$);

R$^{31}$ represents hydrogen, cyano(C$_{1-6}$)alkyl, C$_{1-6}$ alkyl, trifluoromethyl, trifluoro-ethyl, C$_{1-6}$ alkylsulphonyl, (C$_{1-6}$) alkylsulphonyl(C$_{1-6}$)alkyl, formyl, C$_{2-6}$ alkylcarbonyl, carboxy, carboxy(C$_{1-6}$)alkyl, C$_{2-6}$ alkoxycarbonyl, C$_{2-6}$ alkoxycarbonyl(C$_{1-6}$)alkyl, tetrazolyl(C$_{1-6}$)alkyl, aminocarbonyl, C$_{1-6}$ alkylaminocarbonyl, di(C$_{1-6}$)alkylamino-carbonyl, aminosulphonyl, C$_{1-6}$ alkylaminosulphonyl or di(C$_{1-6}$)alkylaminosulphonyl;

R$^{32}$ represents hydrogen, halogen, cyano, hydroxy, hydroxy(C$_{1-6}$)alkyl, C$_{1-6}$ alkylsulphonyl, formyl, carboxy, carboxy(C$_{1-6}$)alkyl, C$_{2-6}$ alkoxycarbonyl, C$_{2-6}$ alkoxycarbonyl(C$_{1-6}$)alkyl, aminosulphonyl, (C$_{1-6}$)alkylsulphoximinyl, [(C$_{1-6}$)alkyl][N—(C$_{1-6}$)alkyl]sulphoximinyl, (C$_{1-6}$)alkylsulphonylaminocarbonyl, (C$_{2-6}$)alkylcarbonylamino-sulphonyl, (C$_{1-6}$)alkoxyaminocarbonyl, tetrazolyl or hydroxyoxadiazolyl;

R$^{33}$ represents hydrogen, halogen, C$_{1-6}$ alkyl, difluoromethyl, trifluoromethyl, hydroxy, hydroxy(C$_{1-6}$)alkyl, C$_{1-6}$ alkoxy, amino or carboxy;

R$^{34}$ represents hydrogen, halogen, halo(C$_{1-6}$)alkyl, hydroxy, C$_{1-6}$ alkoxy, C$_{1-6}$ alkylthio, C$_{1-6}$ alkylsulphinyl, C$_{1-6}$ alkylsulphonyl, amino, C$_{1-6}$ alkylamino, di(C$_{1-6}$)alkylamino, (C$_{2-6}$)alkylcarbonylamino, (C$_{2-6}$)alkylcarbonylamino(C$_{1-6}$)alkyl, (C$_{1-6}$)alkyl-sulphonylamino or (C$_{1-6}$)alkylsulphonylamino(C$_{1-6}$)alkyl;

R$^{35}$ represents hydrogen or C$_{1-6}$ alkyl;

R$^{36}$ and R$^{37}$ independently represent C$_{1-6}$ alkyl; or

R$^{36}$ and R$^{37}$, when taken together with the carbon atom to which they are both attached, represent C$_{3-7}$ cycloalkyl; and W, K, R$^2$, R$^5$, R$^{10}$, R$^b$ and R$^f$ are as defined above.

Generally, U represents O, S(O)$_2$, N(R$^{31}$) or C(R$^{32}$)(R$^{33}$). Typically, U represents O, N(R$^{31}$) or C(R$^{32}$)(R$^{33}$).

In a first embodiment, U represents O. In a second embodiment, U represents S. In a third embodiment, U represents S(O). In a fourth embodiment, U represents S(O)$_2$. In a fifth embodiment, U represents S(O)(NR$^b$). In a sixth embodiment, U represents N(R$^{31}$). In a seventh embodiment, U represents C(R$^{32}$)(R$^{33}$).

Typical values of R$^{31}$ include hydrogen, cyanoethyl, methyl, ethyl, isopropyl, trifluoromethyl, trifluoroethyl, methylsulphonyl, methylsulphonylethyl, formyl, acetyl, carboxy, carboxymethyl, carboxyethyl, methoxycarbonyl, ethoxycarbonyl, tert-butoxy-carbonyl, ethoxycarbonylmethyl, ethoxycarbonylethyl, tetrazolylmethyl, aminocarbonyl, methylaminocarbonyl, dimethylaminocarbonyl, aminosulphonyl, methylaminosulphonyl and dimethylaminosulphonyl.

Suitably, R$^{31}$ represents hydrogen or C$_{1-6}$ alkyl.

Suitable values of R$^{31}$ include hydrogen and methyl.

In a first embodiment, R$^{31}$ represents hydrogen. In a second embodiment, R$^{31}$ represents C$_{1-6}$ alkyl, especially methyl.

Typical values of R$^{32}$ include hydrogen, fluoro, cyano, hydroxy, hydroxymethyl, methylsulphonyl, formyl, carboxy, carboxymethyl, carboxyethyl, methoxycarbonyl, ethoxycarbonyl, tert-butoxycarbonyl, methoxycarbonylmethyl, methoxycarbonylethyl, ethoxycarbonylmethyl, ethoxycarbonylethyl, aminosulphonyl, methylsulphoximinyl, (methyl)(N-methyl)sulphoximinyl, methylsulphonylaminocarbonyl, acetylaminosulphonyl, methoxyaminocarbonyl, tetrazolyl and hydroxyoxadiazolyl.

Suitably, R$^{32}$ represents hydrogen, halogen or cyano.

Suitable values of R$^{32}$ include hydrogen, fluoro and cyano.

In a first embodiment, R$^{32}$ represents hydrogen. In a second embodiment, R$^{32}$ represents halogen, especially fluoro. In a third embodiment, R$^{32}$ represents cyano.

Generally, R$^{33}$ represents hydrogen, halogen, C$_{1-6}$ alkyl, difluoromethyl or trifluoromethyl.

Typical values of R$^{33}$ include hydrogen, fluoro, methyl, ethyl, isopropyl, difluoromethyl, trifluoromethyl, hydroxy, hydroxymethyl, methoxy, amino and carboxy.

Suitably, R$^{33}$ represents hydrogen, halogen or difluoromethyl.

Suitable values of R$^{33}$ include hydrogen, fluoro and difluoromethyl.

In a first embodiment, R$^{33}$ represents hydrogen. In a second embodiment, R$^{33}$ represents halogen. In one aspect of that embodiment, R$^{33}$ represents fluoro. In a third embodiment, R$^{33}$ represents C$_{1-6}$ alkyl. In a first aspect of that embodiment, R$^{33}$ represents methyl. In a second aspect of that embodiment, R$^{33}$ represents ethyl. In a third aspect of that embodiment, R$^{33}$ represents isopropyl. In a fourth embodiment, R$^{33}$ represents difluoromethyl. In a fifth embodiment, R$^{33}$ represents trifluoromethyl. In a sixth embodiment, R$^{33}$ represents hydroxy. In a seventh embodiment, R$^{33}$ represents hydroxy(C$_{1-6}$)alkyl. In one aspect of that embodiment, R$^{33}$ represents hydroxymethyl. In an eighth embodiment, R$^{33}$ represents C$_{1-6}$ alkoxy. In one aspect of that embodiment, R$^{33}$ represents methoxy. In a ninth embodiment, R$^{33}$ represents amino. In a tenth embodiment, R$^{33}$ represents carboxy.

In a first embodiment, R$^{34}$ represents hydrogen. In a second embodiment, R$^{34}$ represents halogen. In one aspect of that embodiment, R$^{34}$ represents fluoro. In a third embodiment, R$^{34}$ represents halo(C$_{1-6}$)alkyl. In one aspect of that embodiment, R$^{34}$ represents fluoromethyl. In a fourth embodiment, R$^{34}$ represents hydroxy. In a fifth embodiment, R$^{34}$ represents C$_{1-6}$ alkoxy, especially methoxy. In a sixth embodiment, R$^{34}$ represents C$_{1-6}$ alkylthio, especially methylthio. In a seventh embodiment, R$^{34}$ represents C$_{1-6}$ alkylsulphinyl, especially methylsulphinyl. In an eighth embodiment, R$^{34}$ represents C$_{1-6}$ alkylsulphonyl, especially methylsulphonyl. In a ninth embodiment, R$^{34}$ represents amino. In a tenth embodiment, R$^{34}$ represents C$_{1-6}$ alkylamino, especially methylamino. In an eleventh embodiment, R$^{34}$ represents di(C$_{1-6}$)alkylamino, especially dimethylamino. In a twelfth embodiment, R$^{34}$ represents (C$_{2-6}$)alkylcarbonylamino, especially acetylamino. In a thirteenth embodiment, R$^{34}$ represents (C$_{2-6}$)alkylcarbonylamino (C$_{1-6}$)alkyl, especially acetylaminomethyl. In a fourteenth embodiment, R$^{34}$ represents (C$_{1-6}$)alkylsulphonyl-amino, especially methylsulphonylamino. In a fifteenth embodiment, $R^{34}$ represents $(C_{1-6})$alkylsulphonylamino$(C_{1-6})$alkyl, especially methylsulphonylaminomethyl.

Suitably, $R^{34}$ represents hydrogen or amino.

Suitable values of $R^{35}$ include hydrogen and methyl.

In a first embodiment, $R^{35}$ represents hydrogen. In a second embodiment, $R^{35}$ represents $C_{1-6}$ alkyl, especially methyl.

Suitably, $R^{36}$ represents methyl or ethyl, especially methyl.

Suitably, $R^{37}$ represents methyl or ethyl, especially methyl.

Alternatively, $R^{36}$ and $R^{37}$, when taken together with the carbon atom to which they are both attached, may suitably represent cyclopropyl, cyclobutyl, cyclopentyl, cyclohexyl or cycloheptyl.

Specific novel compounds in accordance with the present invention include each of the compounds whose preparation is described in the accompanying Examples, and pharmaceutically acceptable salts and solvates thereof, and co-crystals thereof.

The compounds in accordance with the present invention are beneficial in the treatment and/or prevention of various human ailments. These include autoimmune and inflammatory disorders; neurological and neurodegenerative disorders; pain and nociceptive disorders; cardiovascular disorders; metabolic disorders; ocular disorders; and oncological disorders.

Inflammatory and autoimmune disorders include systemic autoimmune disorders, autoimmune endocrine disorders and organ-specific autoimmune disorders. Systemic autoimmune disorders include systemic lupus erythematosus (SLE), psoriasis, psoriatic arthropathy, vasculitis, inflammatory myopathy (including polymyositis, dermatomyositis, inclusion body myositis), scleroderma, multiple sclerosis, systemic sclerosis, ankylosing spondylitis, rheumatoid arthritis, non-specific inflammatory arthritis, juvenile inflammatory arthritis, juvenile idiopathic arthritis (including oligoarticular and polyarticular forms thereof), anaemia of chronic disease (ACD), Still's disease (juvenile and/or adult onset), Behcet's disease and Sjögren's syndrome. Autoimmune endocrine disorders include thyroiditis. Organ-specific autoimmune disorders include Addison's disease, haemolytic or pernicious anaemia, acute kidney injury (AKI; including cisplatin-induced AKI), diabetic nephropathy (DN), obstructive uropathy (including cisplatin-induced obstructive uropathy), glomerulonephritis (including Goodpasture's syndrome, immune complex-mediated glomerulonephritis and antineutrophil cytoplasmic antibodies (ANCA)-associated glomerulonephritis), lupus nephritis (LN), minimal change disease, Graves' disease, idiopathic thrombocytopenic purpura, inflammatory bowel disease (including Crohn's disease, ulcerative colitis, indeterminate colitis and pouchitis), pemphigus, atopic dermatitis, autoimmune hepatitis, primary biliary cirrhosis, autoimmune pneumonitis, autoimmune carditis, myasthenia gravis, spontaneous infertility, osteoporosis, osteopenia, erosive bone disease, chondritis, cartilage degeneration and/or destruction, fibrosing disorders (including various forms of hepatic and pulmonary fibrosis), asthma, rhinitis, chronic obstructive pulmonary disease (COPD), respiratory distress syndrome, sepsis, fever, muscular dystrophy (including Duchenne muscular dystrophy) and organ transplant rejection (including kidney allograft rejection).

Additional inflammatory and autoimmune disorders include scleritis, Takayasu arteritis, giant cell arteritis scleritis, hidradenitis suppurativa, pyoderma gangrenosum, sarcoidosis, polymyalgia rheumatica, axial spondyloarthritis.

Neurological and neurodegenerative disorders include Alzheimer's disease, Parkinson's disease, Huntington's disease, ischaemia, stroke, amyotrophic lateral sclerosis, spinal cord injury, head trauma, seizures and epilepsy.

Cardiovascular disorders include thrombosis, cardiac hypertrophy, hypertension, irregular contractility of the heart (e.g. during heart failure), and sexual disorders (including erectile dysfunction and female sexual dysfunction). Modulators of TNFα function may also be of use in the treatment and/or prevention of myocardial infarction (see J. J. Wu et al., *JAMA*, 2013, 309, 2043-2044).

Metabolic disorders include diabetes (including insulin-dependent diabetes mellitus and juvenile diabetes), dyslipidemia and metabolic syndrome.

Ocular disorders include retinopathy (including diabetic retinopathy, proliferative retinopathy, non-proliferative retinopathy and retinopathy of prematurity), macular oedema (including diabetic macular oedema), age-related macular degeneration (ARMD), vascularisation (including corneal vascularisation and neovascularisation), retinal vein occlusion, and various forms of uveitis (including iritis) and keratitis.

Oncological disorders, which may be acute or chronic, include proliferative disorders, especially cancer, and cancer-associated complications (including skeletal complications, cachexia and anaemia). Particular categories of cancer include haematological malignancy (including leukaemia and lymphoma) and non-haematological malignancy (including solid tumour cancer, sarcoma, meningioma, glioblastoma multiforme, neuroblastoma, melanoma, gastric carcinoma and renal cell carcinoma). Chronic leukaemia may be myeloid or lymphoid. Varieties of leukaemia include lymphoblastic T cell leukaemia, chronic myelogenous leukaemia (CML), chronic lymphocytic/lymphoid leukaemia (CLL), hairy-cell leukaemia, acute lymphoblastic leukaemia (ALL), acute myelogenous leukaemia (AML), myelodysplastic syndrome, chronic neutrophilic leukaemia, acute lymphoblastic T cell leukaemia, plasmacytoma, immunoblastic large cell leukaemia, mantle cell leukaemia, multiple myeloma, acute megakaryoblastic leukaemia, acute megakaryocytic leukaemia, promyelocytic leukaemia and erythroleukaemia. Varieties of lymphoma include malignant lymphoma, Hodgkin's lymphoma, non-Hodgkin's lymphoma, lymphoblastic T cell lymphoma, Burkitt's lymphoma, follicular lymphoma, MALT1 lymphoma and marginal zone lymphoma. Varieties of non-haematological malignancy include cancer of the prostate, lung, breast, rectum, colon, lymph node, bladder, kidney, pancreas, liver, ovary, uterus, cervix, brain, skin, bone, stomach and muscle. Modulators of TNFα function may also be used to increase the safety of the potent anticancer effect of TNF (see F. V. Hauwermeiren et al., *J. Clin. Invest.*, 2013, 123, 2590-2603).

Compounds according to the present invention can be particularly beneficial for the treatment of rheumatoid arthritis, psoriasis, psoriatic arthropathy, axial spondyloarthritis, juvenile idiopathic arthritis, Crohn's disease, ulcerative colitis, uveitis, Behcet's disease and Takayasu arteritis.

The present invention also provides a pharmaceutical composition which comprises a compound in accordance with the invention as described above, or a pharmaceutically acceptable salt or solvate thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (I) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (I) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g.

dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds of use in the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds of use in the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds of use in the present invention may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds of use in the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of use in the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

If desired, a compound in accordance with the present invention may be co-administered with another pharmaceutically active agent, e.g. an anti-inflammatory molecule.

It will be apparent to the person skilled in the art that there are various synthetic pathways that can lead to the compounds according to the invention. The following processes are aimed at illustrating some of these synthetic pathways but should not be construed in any way as a limitation on how the compounds according to the invention should be made.

It will also be apparent to the person skilled in the art that there may be variations in the synthetic pathways depending on the sub-classes of compounds of formula (I).

Compounds of formula (I) above, may be prepared by a process which comprises intramolecular cyclisation or includes reaction of an intermediate of formula (III),

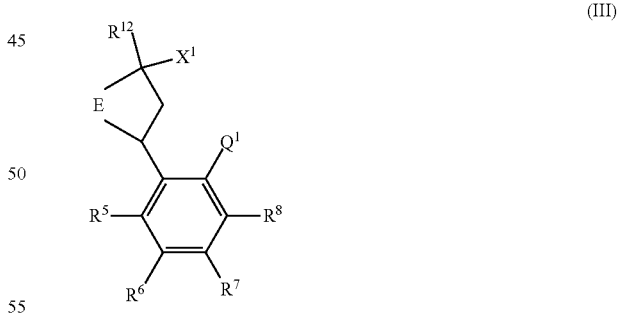

(III)

wherein E, $R^5$, $R^6$, $R^7$, $R^8$ and $R^{12}$ are as defined above;
$X^1$ represents Y, —$SO_2$—Cl, —SH, —OH, —$(CH_2)_n$—$COOR^j$ or —$(CH_2)_n$—$NHR^f$;
$Q^1$ represents —$(CH_2)_m$—$SO_2$—Cl, —$(CH_2)_m$—Y, —$(CH_2)_m$—OH, —$(CH_2)_m$—CN, —$(CH_2)_n$—$COOR^j$ or —$(CH_2)_n$—$NHR^f$;
$R^f$ is as defined above;
represents hydrogen or methyl;
n represents 0 or 1;
m represents 1 or 2;
Y represents a suitable leaving group.

Suitably, Y represents halogen or $(C_{1-6})$alkylsulphonate.

Appositely, Y represents bromo or methylsulphonate.

Suitably, $R^f$ represents hydrogen.

Compounds of formula (I) wherein $R^{12}$ represents hydrogen, -G- represents —N($R^f$)—C(O)—CH$_2$—, wherein $R^f$ is hydrogen, may be prepared by a process which comprises intramolecular cyclization of an intermediate of formula (III) wherein, $X^1$ represents —(CH$_2$)$_n$—NHR$^f$, wherein $R^f$ represents hydrogen and n represents 0, and $Q^1$ represents —(CH$_2$)$_n$—COOR$^j$, represents hydrogen and n represents 1, in the presence of 4-methylmorpholine and (1-cyano-2-ethoxy-2-oxoethylidenaminooxy) dimethylamino-morpholinocarbenium hexafluorophosphate (COMU). The reaction is conveniently effected in acetonitrile.

Compounds of formula (I) wherein $R^{12}$ represents hydrogen, -G- represents —CH$_2$—N($R^f$)—C(O)— may be prepared in a similar fashion by a process which comprises intramolecular cyclization of an intermediate of formula (III) wherein $X^1$ represents —(CH$_2$)$_n$—NHR$^f$, $R^f$ represents hydrogen, n represents 1 and $Q^1$ represents —(CH$_2$)$_n$—COOR$^j$, wherein n represents 0 and $R^j$ represents hydrogen or methyl.

Compounds of formula (I) wherein $R^{12}$ represents hydrogen, -G- represents —C(O)—N($R^f$)—CH$_2$— may be prepared in a similar fashion by a process which comprises intramolecular cyclization of an intermediate of formula (III) wherein $X^1$ represents —(CH$_2$)$_n$—COOR$^j$, wherein n represents 0 and $R^j$ represents hydrogen and $Q^1$ represents —(CH$_2$)$_n$—NHR$^f$, wherein $R^f$ represents hydrogen and n represents 1.

Alternatively, compounds of formula (I) wherein $R^{12}$ represents hydrogen, -G-represents —N($R^f$)—C(O)—CH$_2$— may be prepared by a process which comprises intramolecular cyclization of an intermediate of formula (III) wherein, $X^1$ represents —(CH$_2$)$_n$—NHR$^f$, $R^f$ represents hydrogen and n represents 0, and $Q^1$ represents —(CH$_2$)$_n$—COOR$^j$, $R^j$ represents methyl and n represents 1. The reaction is conveniently effected in the presence of trimethylaluminium in dichloromethane at elevated temperature.

Compounds of formula (I) wherein $R^{12}$ represents hydrogen, -G- represents —N($R^g$)—CH$_2$—CH$_2$— wherein $R^g$ represents hydrogen may be prepared by a process involving reduction of —N($R^f$)—C(O)—CH$_2$—, wherein $R^f$ represents hydrogen. Such process is conveniently effected in the presence of lithium aluminium hydride in a suitable solvent, e.g. THF.

Compounds of formula (I) wherein $R^{12}$ represents hydrogen, -G- represents —S(O)$_2$—N($R^f$)—CH$_2$—, wherein $R^f$ represents hydrogen may be prepared by a process involving intramolecular cyclization of intermediates of formula (III) wherein $X^1$ represents sulfonyl chloride and $Q^1$ represents —(CH$_2$)$_n$—NHR$^f$ wherein n represents 1 and $R^f$ represents hydrogen. The reaction is conveniently effected in the presence suitable base, e.g. disiopropylethylaamine or triethylamine, in a suitable solvent, e.g. dimethyl formamide.

In a similar fashion, compounds of formula (I) wherein $R^{12}$ represents hydrogen, -G- represents —N($R^f$)—SO$_2$—CH$_2$, wherein $R^f$ represents hydrogen, may be prepared by a process involving intramolecular cyclization of intermediates of formula (III) wherein $X^1$ represents —(CH$_2$)—NHR$^f$, $R^f$ represents hydrogen and n represents 0 and $Q^1$ represents —(CH$_2$)$_m$—SO$_2$Cl, wherein m represents 1.

Compounds of formula (I) wherein $R^{12}$ represents hydrogen, -G- represents —O—CH$_2$—CH$_2$—, may be prepared by a process involving intramolecular cyclization of intermediates of formula (III) wherein $X^1$ represents hydroxy and $Q^1$ represents —(CH$_2$)$_m$—Y wherein m represents 2 and Y represents $(C_{1-6})$alkylsulphonate. The reaction is conveniently effected in the presence of a suitable base, e.g. sodium hydride, according to methods known to the person skilled in the art.

Compounds of formula (I) wherein $R^{12}$ represents hydrogen, -G- represents —S—CH$_2$—CH$_2$—, may be prepared via an analogous method involving intramolecular cyclization of intermediates of formula (III) wherein $X^1$ represents —SH and $Q^1$ represents —(CH$_2$)$_m$—Y, wherein m represents 2 and Y represents $(C_{1-6})$alkylsulphonate, in the presence of a suitable base such as potassium carbonate.

Alternatively, compounds of formula (I) wherein $R^{12}$ represents hydrogen, -G-represents —S—CH$_2$—CH$_2$—, may be prepared by a process involving intramolecular cyclization of intermediates of formula (III) wherein $X^1$ represents Y, Y representing a halogen, and $Q^1$ represents —(CH$_2$)$_m$—Y, wherein m represents 2 and Y represents $(C_{1-6})$alkylsulphonate. The reaction is conveniently effected with sodium hydrosulfide in the presence of a base.

Compounds of formula (I) wherein $R^{12}$ represents hydrogen, -G- represents —S(O)—CH$_2$—CH$_2$—, may be prepared by oxidation of the corresponding compounds of formula (I) wherein -G- represents —S—CH$_2$—CH$_2$—, for example by treatment with an oxidizing agent such as m-chloroperbenzoic acid.

Compounds of formula (I) wherein $R^{12}$ represents hydrogen, -G- represents —S(O)$_2$—CH$_2$—CH$_2$—, may be prepared by oxidation of the corresponding compounds of formula (I) wherein -G- represents —S(O)—CH$_2$—CH$_2$—, for example by treatment with an oxidizing agent such as m-chloroperbenzoic acid.

Compounds of formula (I) wherein $R^{12}$ represents hydrogen, -G- represents —S(O)(N—$R^f$)—CH$_2$—CH$_2$—, may be prepared from the corresponding compounds of formula (I) wherein -G- represents —S(O)—CH$_2$—CH$_2$—, by treatment with an oxidizing agent, in the presence of a transition metal catalyst and trifluoroacetamide, in a suitable solvent, e.g. dichlormethane, according to conditions analogous to the ones described by C. Bolm and al. in *Organic Letters,* 2004, 6(8), 1305-1307.

Compounds of formula (I) wherein $R^{12}$ represents hydrogen, -G- represents —O—C(O)—N($R^f$)—, wherein $R^f$ represents hydrogen may be prepared by a process involving intramolecular cyclization of intermediates of formula (III) wherein $X^1$ represents hydroxy and $Q^1$ represents —(CH$_2$)—NHR$^f$, wherein n represents 0 and $R^f$ represents hydrogen. The reaction is conveniently effected in the presence of carbonyl di-imidazole or phosgene according to methods known to the person skilled in the art.

Compounds of formula (I) wherein $R^{12}$ represents hydrogen, -G- represents —O—C(O)—CH$_2$—, may be prepared by a process involving intramolecular cyclization of intermediates of formula (III) wherein $X^1$ represents hydroxy and $Q^1$ represents —(CH$_2$)—COOR$^j$ wherein represents hydrogen or $C_{1-4}$ alkyl and n represents 1.

When $R^j$ represents $C_{1-4}$ alkyl, the reaction is conveniently effected by heating at elevated temperature, according to methods known to the skilled person in the art.

When $R^j$ represents hydrogen, the reaction is conveniently effected in the presence of a suitable coupling agent e.g., 1-ethyl-3-(3-dimethylaminopropyl)carbodiimide (EDC), according to methods known to the person skilled in the art.

Compounds of formula (I) wherein $R^{12}$ represents hydrogen, -G- represents —N($R^f$)—C(O)—N($R^f$)—, may be prepared by a process involving intramolecular cyclization of intermediates of formula (III) wherein $X^1$ represents —(CH$_2$)—NHR$^f$— wherein n represents 0 and $R^f$ represents hydrogen, and $Q^1$ represents —$(CH_2)_n$—$NHR^f$, wherein n represents 0 and $R^f$ represents hydrogen. The reaction is conveniently effected in the presence of carbonyl di-imidazole or phosgene according to methods known to the person skilled in the art.

Compounds of formula (I) wherein $R^{12}$ represents hydrogen, -G- represents —O—$S(O)_2$—$N(R^f)$—, may be prepared by a process involving intramolecular cyclization of intermediates of formula (III) wherein $X^1$ represents hydroxy and $Q^1$ represents —$(CH_2)_n$—$NHR^f$, wherein n represents 0 and $R^f$ represents hydrogen. The reaction is conveniently effected in the presence of sulfuryl chloride according to methods known to the person skilled in the art.

Compounds of formula (I) wherein $R^{12}$ represents hydrogen, -G- represents —$N(R^f)$—$S(O)_2$—$N(R^f)$—, may be prepared by a process involving intramolecular cyclization of intermediates of formula (III) wherein $X^1$ represents —$(CH_2)_n$—$NHR^f$— wherein n represents 0 and $R^f$ represents hydrogen, and $Q^1$ represents —$(CH_2)_n$—$NHR^f$, wherein n represents 0 and $R^f$ represents hydrogen. The reaction is conveniently effected in the presence of sulfuryl chloride according to methods known to the person skilled in the art.

Compounds of formula (I) wherein $R^{12}$ represents hydrogen, -G- represents —$N(R^f)$—C(O)—O—$CH_2$— may be prepared by a process involving intramolecular cyclization of intermediates of formula (III) wherein $X^1$ represents —$(CH_2)_n$—$COOR^j$ wherein n represents 0 and $R^j$ represents hydrogen, and $Q^1$ represents —$(CH_2)_m$—OH, wherein m represents 1. The reaction is conveniently effected in the presence of in the presence of diphenylphosphoryl azide, according to methods know to the skilled person in the art.

Compounds of formula (I) wherein $R^{12}$ represents hydrogen, -G- represents —$N(R^f)$—C=$N(R^f)$—$CH_2$ may be prepared by reaction of compounds of formula (I) wherein $R^{12}$ represents hydrogen, -G- represents —$N(R^f)$—C(O)—$CH_2$. The reaction is conveniently effected in two steps by (i) treatment with of Lawesson's reagent to form corresponding compound wherein -G- represents —$N(R^f)$—C(S)—CH2, followed by (ii) treatment with $NH_2R^f$, according to methods known to the skilled person in the art.

Alternatively, compounds of formula (I) wherein $R^{12}$ represents hydrogen, -G-represents —$N(R^f)$—C=$N(R^f)$—$CH_2$ and $R^f$ represents hydrogen, may be prepared by may be prepared by a process involving intramolecular cyclization of intermediates of formula (III) wherein $X^1$ represents —$(CH_2)_n$—$NHR^f$— wherein n represents 0 and $R^f$ represents hydrogen and $Q^1$ represents —$(CH_2)_m$—CN, wherein m represents 1. The reaction is conveniently effected at elevated temperature in the presence of an acid, according to methods known to the skilled in the art.

Intermediates of formula (III) wherein $Q^1$ represents —$(CH_2)_n$—$COOR^j$ wherein n represents 0 or 1 and $R^j$ represents hydrogen, may be prepared by a process comprising reacting an intermediate of formula (IIIa),

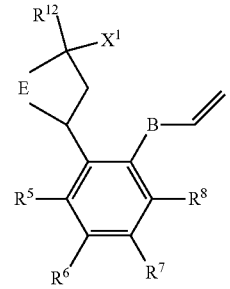

(IIIa)

wherein

B represents —$(CH_2)_n$—; and

E, $R^5$, $R^6$, $R^7$, $R^8$, $R^{12}$, n and $X^1$ are as defined above.

Such process is conveniently effected in the presence of an oxidizing agent, such as sodium periodate, in the presence of a transition metal catalyst, e.g. ruthenium chloride (II), in a suitable solvent.

Intermediate of formula (III) wherein $Q^1$ represents —$(CH_2)_n$—$COOR^j$, n represents 1 and $R^j$ represents $C_{1-4}$ alkyl may be prepared from intermediates of formula (III) wherein $Q^1$ represents —$(CH_2)_n$—$COOR^j$, wherein n represents 1 and $R^j$ represents hydrogen, according to esterification methods known the person skilled in the art.

Intermediates of formula (III) wherein $Q^1$ represents —$(CH_2)_n$—$NHR^f$, $R^f$ is hydrogen, n represents 0 or 1, may be prepared from intermediates of formula (III) wherein $Q^1$ represents —$(CH_2)_n$—$COOR^j$, wherein n represents 0 or 1 and $R^j$ represents $C_{1-4}$ alkyl or hydrogen according to a process involving a Curtius rearrangement. When $R^j$ represents $C_{1-4}$ alkyl the process first involves reacting intermediates (III) with a suitable base. The Curtius rearrangement is conveniently effected in the presence of diphenylphosphoryl azide in tert-butanol. Deprotection of the amine is subsequently effected by further treatment with a base.

Intermediate of formula (IIIa) wherein $Q^1$ represents —$(CH_2)_m$—Y and Y represents $(C_{1-6})$alkylsulphonate and m represents respectively 1 or 2, may be prepared from intermediates of formula (IIIa) wherein $Q^1$ represents —$(CH_2)_n$—$COOR^j$, n represents respectively 0 or 1 and $R^j$ represents hydrogen, by a process which involves a reduction of the carboxylic moiety with a reducing agent followed by reaction with $(C_{1-6})$ alkylsulphonylchloride, according to methods known the person skilled in the art.

Intermediate of formula (III) wherein $Q^1$ represents —$(CH_2)_m$—OH wherein m represents 1 or 2, may be prepared from intermediates of formula (IIIa) wherein $Q^1$ represents —$(CH_2)_n$—$COOR^j$, wherein n represents respectively 0 or 1 and $R^j$ represents hydrogen, by a process which involves a reduction of the carboxylic moiety with a reducing agent, according to methods known the person skilled in the art.

Intermediates of formula (IIIa) wherein $Q^1$ represents —$(CH_2)_m$—CN may be prepared from corresponding intermediates of formula (IIIa) wherein $Q^1$ represents $(CH_2)_m$—OH or —$(CH_2)_m$—Y, wherein Y represents $(C_{1-6})$alkylsulphonate, according to methods known to the skilled in the art.

Intermediates of formula (IIIa) may be prepared by a process involving reaction of an intermediate represented by formula (IIIb),

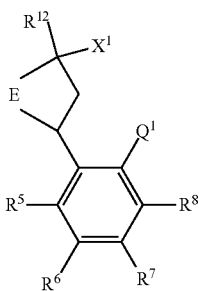

(IIIb)

wherein $R^5$, $R^6$, $R^7$, $R^8$, $R^{12}$ and $X^1$ are as defined above, and $Z^1$ represents halogen, for example bromo.

When B represents —$(CH_2)_n$— and n represents 0, the reaction is conveniently effected by reacting intermediate of formula (IIIb) with potassium vinyl trifluoroborate, in the presence of a transition metal catalyst complex, e.g. 1,1′-bis(diphenylphosphino)ferrocene-palladium(II)dichloride dichloromethane complex, and a base, e.g. an inorganic base such as cesium carbonate in a suitable solvent, e.g. 1,4-dioxane or a mixture of 1,4-dioxane and water.

When B represents —$(CH_2)_n$— and n represents 1, the reaction is conveniently effected by reacting intermediate of formula (IIIb) with allyltributyltin in the presence of a transition metal catalyst, e.g. bis(triphenylphosphine)palladium(II) dichloride and an alkali metal salt, e.g. LiCl, in a suitable solvent.

Intermediates of formula (IIIb) wherein E represents (Ea) as defined above, and $X^1$ represents hydroxy, may be prepared by a process which comprises the intramolecular cyclisation and desilylation of an intermediate of formula (IV),

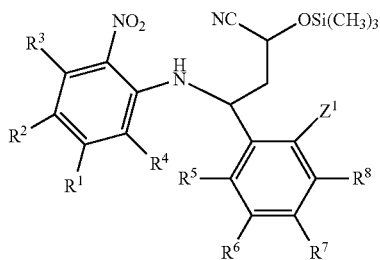

(IV)

wherein $Z^1$, $R^1$, $R^2$, $R^3$, $R^4$, $R^5$, $R^6$, $R^7$, $R^8$ are as defined above.

The reaction is suitably performed in the presence of tin(II) chloride at elevated temperature in a polar solvent, e.g. ethanol.

Intermediate (IV) as defined above may be prepared by a process comprising reacting intermediate (V),

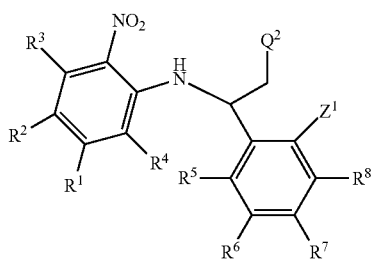

(V)

wherein $Q^2$ represents —C(O)—H, and $Z^1$, $R^2$, $R^3$, $R^4$, $R^5$, $R^6$, and $Q^1$ are as defined above; with zinc iodide and triethylsilyl cyanide in the presence of a base, e.g. triethylamine.

Typically, the intermediate of formula (V) wherein $Q^2$ represents —C(O)—H may be prepared from the corresponding intermediate wherein $Q^2$ represents —$CO_2R^h$ and $R^h$ represents $C_{1-6}$ alkyl, by reduction with a conventional reducing agent, e.g. a metal hydride, such as diisobutylaluminium hydride (DIBAL-H).

The intermediate of formula (V) wherein $Q^2$ represents —$CO_2R^h$ may be obtained by a process which comprises reacting an intermediate of formula (VI) with an intermediate of formula (VII),

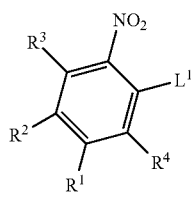

(VI)

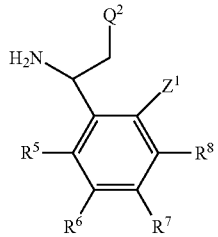

(VII)

wherein $R^1$, $R^2$, $R^3$, $R^4$, $R^5$, $R^6$, $R^7$, $R^8$, $Z^1$ and $Q^2$ are as defined above; and $L^{1'}$ is a suitable leaving group, e.g. a halogen atom, for example bromine.

The reaction is conveniently performed in the presence of a base, e.g. an inorganic base, such as potassium carbonate, in a suitable solvent, e.g. an apolar solvent such as acetonitrile, at elevated temperature.

Intermediates of formula (VII) may be prepared by a multi-step process starting from an intermediate of formula (VIII),

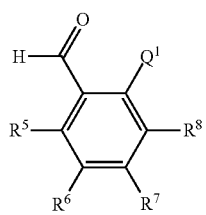

(VIII)

wherein $R^5$, $R^6$, $R^7$, $R^8$ and $Q^1$ are as defined above; which process comprises the following steps:

(i) Reaction of intermediate (VIII) with (S)-t-butylsulfinamide in the presence of $K_3PO_4$/$KHPO_4$ in a suitable solvent, e.g. THF;

(ii) Reacting the compound obtained from step (i) with a compound of formula $L^2$-Z-$Q^2$, wherein Z and $Q^2$ are as defined above and $L^2$ is a suitable leaving group, e.g. halogen, such as bromine, and activated zinc metal dust prepared according to conditions described in Hilpert, H. et al, *Journal of Medicinal Chemistry*, 2013, 56(10), 3980-3995, in the presence of transition metal salt, e.g. copper chloride at elevated temperature;

(iii) Subsequent reaction with a strong mineral acid, e.g. hydrogen chloride.

Intermediates of formula (VIII) wherein $R^5$ represents halogen, e.g. chloro, may be transformed into the corresponding intermediate of formula (VIII) wherein $R^5$ represents difluoromethoxy by a process which comprises (i) reaction with potassium hydroxide, in water at low temperature and (ii) reaction with diethyl(bromodifluoromethyl) phosphonate, at low temperature.

Intermediates of formula (III) wherein E represents (Ea) as defined above, and —$X^1$ represents —NH($R^f$) and $R^f$ represents hydrogen, may be prepared by a process which comprises the reduction, intramolecular cyclization and desulfination of an intermediate of formula (IVa),

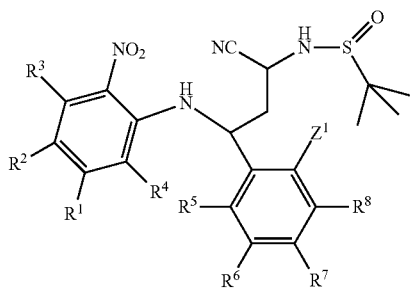

(IVa)

wherein $Z^1$, $R^1$, $R^2$, $R^3$, $R^4$, $R^5$, $R^6$, $R^7$, and $R^8$ are as defined above.

The reaction is suitably performed in the presence of tin(II) chloride, followed by addition of a strong acid, e.g. hydrogen chloride, at elevated temperature in a polar solvent, e.g. ethanol.

Alternatively, the reduction and cyclization may be performed by a process involving (i) reduction using hydrogen under pressure, in the presence of zinc bromide and of platinum on charcoal and (ii) addition of a strong acid, e.g. hydrogen chloride, at elevated temperature in a polar solvent, e.g. ethanol.

Intermediates of formula (IVa), may be prepared by a multi-step process starting from corresponding intermediates (IVb),

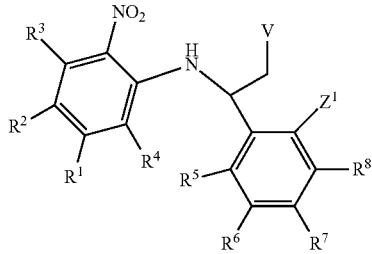

(IVb)

wherein $R^1$, $R^2$, $R^3$, $R^4$, $R^5$, $R^6$, $R^7$, $R^8$ and $Z^1$ are as defined above, and V represents CH=$CH_2$, which process comprises:

(i) Reacting intermediate (IVb) with sodium periodate, in the presence of potassium dioxide(dioxo)osmium hydrate and 2,6-dimethyl pyridine, followed by addition of sodium thiosulfate, to afford corresponding intermediates of formula (IVb) wherein V represents CH=O;

(ii) Reacting intermediates of formula (IVb) wherein V represents CH=O with (R)-2-methylpropane-2-sulfinamide, in the presence of a transition metal catalyst, eg. titanium (IV) isopropoxide, in a suitable solvent, e.g. dichloromethane, to afford corresponding intermediate of formula (IVb) wherein V represents CH=N—(SO)-tert-butyl;

(iii) Further reaction with sodium cyanide, in the presence of scandium triflate, in a suitable solvent, e.g. tetrahydrofuran, to afford intermediates of formula (IVa).

Intermediates of formula (IVb) wherein $R^1$, $R^2$, $R^3$, $R^4$, $R^5$, $R^6$, $R^7$, $R^8$ and $Z^1$ are as defined above, and V represents CH=$CH_2$, may be prepared by a process comprising reacting intermediates of formula (VIIa),

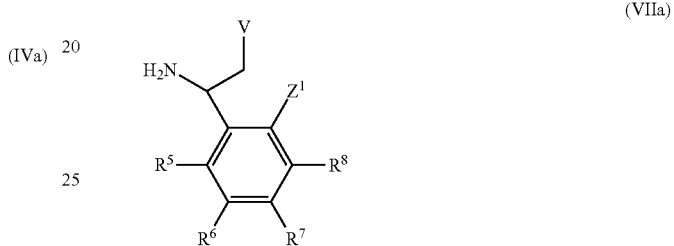

(VIIa)

wherein V, $R^5$, $R^6$, $R^7$, $R^8$ and $Z^1$ are as defined above for intermediates of formula (IVb), with an intermediate of formula (VI) as defined above, wherein $L^1$ is a halogen, e.g. fluorine, under conditions analogous to those described for the preparation of intermediates of formula (V).

Intermediates of formula (VIIa) may be prepared by a process analogous to the one described for intermediates of formula (VII), but wherein $Q^2$ is replaced by V.

Intermediates of formula (IIIb), wherein E represents (Eb) or (Ec), as defined above, and wherein $X^1$ represents hydroxy may be prepared from intermediates of formula (IIId),

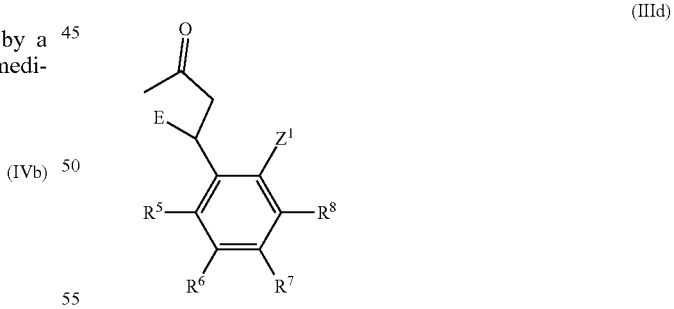

(IIId)

wherein $R^5$, $R^6$, $R^7$, $R^8$ and $Z^1$ are as defined above; by reduction of the carbonyl moiety according to methods known to the person skilled in the art.

Intermediates of formula (III) wherein $X^1$ represents —NH($R^f$), $R^f$ represents hydrogen and $R^{12}$ represents methyl may be prepared from intermediate of formula (IIId) using the following sequence of steps:

(i) Reacting intermediate of formula (IIId) with 2-methyl-2-propanesulfinamide in the presence of Titanium (IV) isopropoxide, in a solvent, e.g. tetrahydrofuran, at a suitable temperature, e.g. 50° C.;

(ii) Adding a solution of methylmagnesium bromide, at low temperature, in a suitable solvent, e.g. dichloromethane;

(iii) Removing the tert-butyl sulphinyl moiety in the presence of a strong acid, e;g. HCl, in a suitable solvent, e.g. 1,4-dioxane.

Intermediates of formula (IIId) may be prepared by a process which comprises intramolecular cyclization of an intermediate of formula (IX),

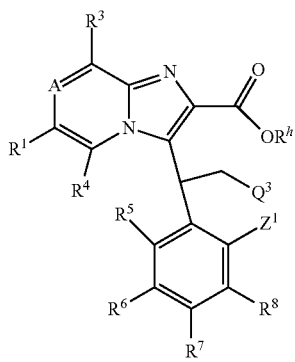

(IX)

wherein A is N or C—$R^2$, $Q^3$ is an electron withdrawing group, preferably an ester moiety, and $R^1$, $R^3$, $R^4$, $R^5$, $R^6$, $R^7$, $R^8$, $R^h$, $Z^1$ are as defined above; in the presence of a base, in a suitable solvent at elevated temperature.

Intermediates of formula (IX) may be prepared by a process which includes reacting an intermediate of formula (X) with an intermediate of formula (XI),

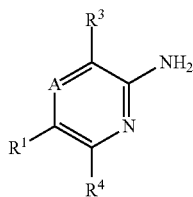

(X)

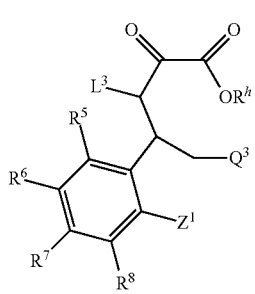

(XI)

wherein A, $R^1$, $R^3$, $R^4$, $R^5$, $R^6$, $R^7$, $R^8$, $R^h$, $Z^1$, $Q^1$ and $Q^3$ are as defined above; and $L^3$ is a suitable leaving group, typically a halogen atom, e.g. bromo.

The reaction is conveniently effected at an elevated temperature in a suitable solvent, e.g. a ($C_{1-4}$)alkanol such as ethanol, or an ether such as 1,4-dioxane or dimethoxyethane, and in the presence of magnesium sulphate.

Alternatively, intermediates of formula (IX), wherein $Q^3$ is —$CO_2H$, may be prepared according to a process which comprises reacting an intermediate of formula (XII),

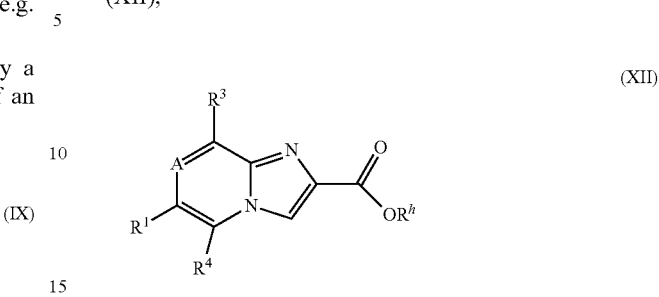

(XII)

wherein A, $R^1$, $R^3$, $R^4$, and $R^h$ are as defined above; with an intermediate of formula (VIII) as defined above, in the presence of Meldrum's acid, according to a method analogous to the one described in international patent application WO 2009/156091 or by M. Kerr et al. in J. Org. Chem 2013, 78, 10534.

The reaction is conveniently effected in a suitable solvent e.g. acetonitrile, in the the presence of proline and magnesium sulphate, at elevated temperature, e.g. 80° C.

Where they are not commercially available, the starting materials of formula (VI), (VIII), (X), (XI) and (XII) may be prepared by methods analogous to those described in the accompanying Examples, or by standard methods well known from the art.

Intermediates of formula (III), (IIIa) or (IIIb) wherein $X^1$ represents amino, may be prepared from intermediates of formula (III), (IIIa) or (IIIb) wherein $X^1$ is hydroxy, by a process which comprises (i) treatment with diphenylphosphorylazide and 1,8-diazabicyclo[5.4.0]undec-7-ene, in a suitable solvent, e.g. tetrahydrofuran, at low temperature, e.g. 0° C., and (ii) subsequent aza-wittig reaction using triphenylphosphine, in a suitable solvent, e.g. a mixture of water and toluene.

Intermediates of formula (III), (IIIa) or (IIIb) wherein E represents (Eb) or (Ec), as defined above, and wherein $X^1$ represents amino may be prepared from intermediates of formula (IIId),
wherein $R^5$, $R^6$, $R^7$, $R^8$, and $Z^1$ are as defined above; by a process which comprises reacting intermediates of formula (IIIA) with a $C_{1-6}$ alkylsulfinamide, e.g. (R)-2-methylpropane-2-sulfinamide, in the presence of a transition metal catalyst, e.g. titanium tetrakis ethanolate, in a suitable solvent, e.g. dichloromethane, followed by reduction with a suitable reducing agent, e.g. sodium borohydride, in a suitable solvent, e.g. tetrahydrofuran.

Intermediates of formula (III), (IIIa) or (IIIb) wherein $X^1$ represents a leaving group Y, e.g. halogen or ($C_{1-6}$)alkylsulphonate, may be prepared from intermediates of formula (III), (IIIa) or (IIIb) wherein $X^1$ is hydroxy, according to standard methods known to the person skilled in the art.

Intermediates of formula (III), (IIIa) or (IIIb) wherein $X^{n1}$ represents —SH, may be prepared from intermediates of formula (III) wherein $X^1$ is hydroxy or a leaving group Y, according to standard methods known to the person skilled in the art.

For example, an intermediate of of formula (III), (IIIa) or (IIIb) wherein $X^1$ is a halogen, may be transformed into, an intermediate of of formula (III), (IIIa) or (IIIb) wherein $X^1$ is —SH, by reaction with sodium hydrosulfide.

Intermediates of formula (III), (IIIa) or (IIIb) wherein $X^1$ represents —$SO_2Cl$ may be prepared from intermediates of formula (III), (IIIa) or (IIIb) wherein $X^1$ is —SH, according to standard methods known to the person skilled in the art.

Compounds of formula (I) or intermediates of formula (III), (IIIa) or (IIIb) wherein $R^f$ or $R^g$ represent hydrogen, may further be transformed into the corresponding compounds of formula (I) or intermediates of formula (III), (IIIa) or (IIIb) wherein $R^f$ or $R^g$ represent optionally substituted $C_{1-6}$ alkyl, or its deuterated equivalent, by reaction with the corresponding optionally substituted $C_{1-6}$ alkyl halide or deuterated equivalent, e.g. $C_{1-6}$ alkyl iodide or its deuterated equivalent, in the presence of a base, e.g. cesium carbonate or potassium bis(trimethylsilyl)amide (KHMDS), in a suitable solvent, e;g., dimethylformamide or THF.

Compounds of formula (I) or intermediates of formula (III), (IIIa) or (IIIb) wherein $R^f$ or $R^g$ represent hydrogen, may further be transformed into the corresponding compounds of formula (I) or intermediates of formula (III) wherein $R^f$ or $R^g$ represent acetyl by reaction with acetic anhydride, in the presence of base, e.g. pyridine, in a suitable solvent, e.g. dichloromethane.

Compounds of formula (I) or intermediates of formula (III), (IIIa) or (IIIb) wherein $R^f$ or $R^g$ represent hydrogen, may further be transformed into the corresponding compounds of formula (I) or intermediates of formula (III), (IIIa) or (IIIb) wherein $R^f$ or $R^g$ represent methyl, by reaction with formaldehyde, in a suitable solvent, e.g. 2,2,2-trifluoroethanol, followed by reaction with a suitable reducing agent, e.g. sodium borohydride.

Compounds of formula (I) or intermediates of formula (III), (IIIa) or (IIIb) wherein $R^f$ or $R^g$ represent hydrogen, may further be transformed into the corresponding compounds of formula (I) or intermediates of formula (III), (IIIa) or (IIIb) wherein $R^f$ or $R^g$ represent $(C_{1-6})$alkyl-sulphonyl by treatment with the appropriate $(C_{1-6})$ alkylsulphonyl halide, e.g. methane sulphonyl chloride, in the presence of a suitable base, e.g. N,N-diisopropylethylamine or triethylamine, in a suitable solvent e.g. dichloromethane.

A compound of formula (I) or an intermediate of formula (III), (IIIa) or (IIIb) which contains a hydroxy group may be alkylated by treatment with the appropriate alkyl halide in the presence of a base, e.g. sodium hydride, or silver oxide.

A compound of formula (I) or an intermediate of formula (III), (IIIa) or (IIIb) which contains hydroxy may be converted into the corresponding fluoro-substituted compound by treatment with diethylaminosulfur trifluoride (DAST) or bis(2-methoxyethyl)aminosulfur trifluoride (BAST). A compound of formula (I) which contains hydroxy may be converted into the corresponding difluoro-substituted compound via a two-step procedure which comprises: (i) treatment with an oxidising agent, e.g. manganese dioxide; and (ii) treatment of the carbonyl-containing compound thereby obtained with DAST.

A compound of formula (I) or an intermediate of formula (III), (IIIa) or (IIIb) which contains an N—H moiety may be alkylated by treatment with the appropriate alkyl halide, typically at an elevated temperature in an organic solvent such as acetonitrile; or at ambient temperature in the presence of a base, e.g. potassium hydroxide, in a suitable solvent, e.g. THF, in the presence of tetra-butylammonium bromide; or at elevated temperature in the presence of a base, e.g. sodium hydride, with or without tetra-butylammonium iodate, in a suitable solvent, e.g. THF; or at elevated temperature in the presence of a an alkali metal carbonate such as potassium carbonate or cesium carbonate, in a suitable solvent, e.g. a dipolar aprotic solvent such as N,N-dimethylformamide. A compound of formula (I) which contains an N—H moiety may be methylated by treatment with formaldehyde in the presence of a reducing agent, e.g. sodium triacetoxyborohydride.

A compound of formula (I) or an intermediate of formula (III), (IIIa) or (IIIb) which contains an N—H moiety may be acylated by treatment with the appropriate acid chloride, e.g. acetyl chloride, or with the appropriate carboxylic acid anhydride, e.g. acetic anhydride, typically at ambient temperature in the presence of a base, e.g. an organic base such as triethylamine.

A compound of formula (I) or an intermediate of formula (III), (IIIa) or (IIIb) which contains an N—H moiety may be converted into the corresponding compound wherein the nitrogen atom is substituted by $C_{1-6}$ alkyl-sulphonyl, e.g. methylsulphonyl, by treatment with the appropriate $C_{1-6}$ alkylsulphonyl chloride, e.g. methanesulphonyl chloride, or with the appropriate $C_{1-6}$ alkylsulphonic acid anhydride, e.g. methanesulphonic anhydride, typically at ambient temperature in the presence of a base, e.g. an organic base such as triethylamine or N,N-diisopropylethyl-amine.

A compound of formula (I) or an intermediate of formula (III), (IIIa) or (IIIb) which contains an N—H moiety may be converted into the corresponding compound wherein the nitrogen atom is substituted by $C_{1-6}$ alkoxy-carbonyl, e.g. methoxycarbonyl, by treatment with the corresponding $C_{1-6}$ alkoxy-carbonyl halide, in the presence of a base, e.g. potassium carbonate, in a suitable solvent, e.g., N, N'-dimethylformamide.

A compound of formula (I) or an intermediate of formula (III), (IIIa) or (IIIb) substituted by amino (—NH$_2$) may be converted into the corresponding compound substituted by $C_{1-6}$ alkylsulphonylamino, e.g. methylsulphonyl-amino, or bis[($C_{1-6}$)alkylsulphonyl]amino, e.g. bis(methylsulphonyl) amino, by treatment with the appropriate $C_{1-6}$ alkylsulphonyl halide, e.g. a $C_{1-6}$ alkylsulphonyl chloride such as methanesulphonyl chloride, in the presence of a suitable base, e.g. N,N-diisopropylethylamine, in a suitable solvent e.g. dichloromethane Similarly a compound of formula (I) or an intermediate of formula (III), (IIIa) or (IIIb) substituted by amino may be transformed into the corresponding compound of formula (I) or intermediate of formula (III), (IIIa) or (IIIb) substituted by NH—SO$_2$—(C$_{3-7}$)cycloalkyl, NH—SO$_2$—(C$_{3-7}$)heterocycloalkyl, NH—SO$_2$-aryl or NH—SO$_2$-heteroaryl respectively from the corresponding (C$_{3-7}$)cycloalkyl-sulphonyl-halide, (C$_{3-7}$)heterocycloalkyl-sulphonyl halide, arylsulphonyl-halide or heteroaryl-sulphonyl-halide.

Similarly, a compound of formula (I) substituted by hydroxy (—OH) may be converted into the corresponding compound substituted by $C_{1-6}$ alkyl-sulphonyloxy, e.g. methylsulphonyloxy, by treatment with the appropriate $C_{1-6}$ alkyl-sulphonyl halide, e.g. a $C_{1-6}$ alkylsulphonyl chloride such as methanesulphonyl chloride.

A compound of formula (I) or an intermediate of formula (III), (IIIa) or (IIIb) substituted by amino (—NH$_2$) may be converted into the corresponding compound substituted by (tert-butyl)(dimethyl)silyloxyethyl-NH— by treatment with (bromoethoxy)-tert-butyldimethylsilane, in the presence of a suitable base, e.g. potassium carbonate, in a suitable solvent, e.g. dimethyl formamide, at elevated temperature.

A compound of formula (I) or an intermediate of formula (III), (IIIa) or (IIIb) containing the moiety —S— may be converted into the corresponding compound containing the moiety —S(O)— by treatment with 3-chloroperoxy-benzoic acid. Likewise, a compound of formula (I) containing the moiety —S(O)— may be converted into the corresponding compound containing the moiety —S(O)$_2$— by treatment with 3-chloroperoxybenzoic acid. Alternatively, a compound of formula (I) containing the moiety —S— may be converted into the corresponding compound containing the moiety —S(O)$_2$— by treatment with Oxone® (potassium peroxymonosulfate).

A compound of formula (I) or an intermediate of formula (III), (IIIa) or (IIIb) containing an aromatic nitrogen atom may be converted into the corresponding N-oxide derivative by treatment with 3-chloroperoxy-benzoic acid.

A compound of formula (I) or an intermediate of formula (III), (IIIa) or (IIIb) which contains a carbonyl may be converted into the corresponding alcohol by treatment with a suitable borohydride, e.g. lithium-tri-sec-butyl-borohydride or sodium borohydride, in a suitable solvent e.g. THF.

A compound of formula (I) or an intermediate of formula (III), (IIIa) or (IIIb) wherein R$^1$ represents halogen, e.g. bromo, may be converted into the corresponding compound wherein R$^1$ represents an optionally substituted aryl or heteroaryl moiety by treatment with the appropriately substituted aryl or heteroaryl boronic acid or a cyclic ester thereof formed with an organic diol, e.g. pinacol, 1,3-propanediol or neopentyl glycol. The reaction is typically effected at elevated temperature in the presence of a transition metal catalyst, e.g. [1,1'-bis(diphenylphosphino)ferrocene]dichloropalladium(II), tetrakis(triphenylphosphine)palladium(0), or bis[3-(diphenylphosphanyl)cyclopenta-2,4-dien-1-yl]iron-dichloropalladium-dichloromethane complex, and a base, e.g. an inorganic base such as sodium carbonate, potassium carbonate or cesium carbonate, or potassium phosphate, in a suitable solvent, e.g. 1,4-dioxane or a mixture of 1,4-dioxane and water.

Alternatively, a compound of formula (I) or an intermediate of formula (III), (IIIa) or (IIIb) wherein R$^1$ represents halogen, e.g. bromo, may be converted into the corresponding compound wherein R$^1$ represents an optionally substituted aryl or heteroaryl moiety by treatment with the appropriately substituted aryl or heteroaryl boronic acid, in the presence of a transition metal catalyst, e.g. tris(dibenzylideneacetone)dipalladium(0), and tricyclohexylphosphoniumtetrafluoroborate, in the presence of a base, e.g. potassium phosphate, in a suitable solvent, e.g. cyclic ether, such as 1,4-dioxane. The reaction is conveniently effected at elevated temperature and microwave technology may be used. A compound of formula (I) wherein R$^1$ represents 2-oxo-(1H)-pyridinyl may be obtained by treatment of the corresponding compound of formula (I) wherein R$^1$ represents 2-methoxy-pyridinyl, with pyridine hydrochloride at elevated temperature, e.g. 160° C.

A compound of formula (I) or an intermediate of formula (III), (IIIa) or (IIIb) wherein R$^1$ represents an ester moiety may be obtained by reacting the corresponding compound of formula (I) or the intermediate of formula (III) wherein R$^1$ is halogen, e.g. chloride, with a base, e.g. sodium carbonate, and the corresponding alcohol moiety in the presence of a transition metal catalyst, typically bis(dicyclohexylphosphino)propane] palladium(II).

A compound of formula (I) or an intermediate of formula (III), (IIIa) or (IIIb) wherein R$^1$ represents cyano may be obtained by reacting the corresponding compound of formula (I) or the intermediate of formula (III) wherein R$^1$ is halogen, e.g. chloride, with zinc cyanide, in the presence of a transition metal catalyst, e.g. tetrakis(triphenylphosphine)palladium, in a suitable solvent, e.g., N,N-dimethylformamide. The reaction is conveniently effected at elevated temperature, e.g. 180° C., using microwave technology.

In general, a compound of formula (I) containing a —C═C— functionality may be converted into the corresponding compound containing a —CH—C— functionality by catalytic hydrogenation, typically by treatment with a hydrogenation catalyst, e.g. palladium on charcoal, under an atmosphere of hydrogen gas, optionally in the presence of a base, e.g. an alkali metal hydroxide such as sodium hydroxide.

A compound of formula (I) or an intermediate of formula (III), (IIIa) or (IIIb) containing an ester moiety, e.g. a C$_{2-6}$ alkoxycarbonyl group such as methoxycarbonyl or ethoxycarbonyl, may be converted into the corresponding compound containing a carboxy (—CO$_2$H) moiety by treatment with an acid, e.g. a mineral acid such as hydrochloric acid.

A compound of formula (I) or an intermediate of formula (III), (IIIa) or (IIIb) containing an ester moiety, e.g. a C$_{2-6}$ alkoxycarbonyl group such as methoxycarbonyl or ethoxycarbonyl, may alternatively be converted into the corresponding compound containing a carboxy (—CO$_2$H) moiety by treatment with a base, e.g. an alkali metal hydroxide selected from lithium hydroxide, sodium hydroxide and potassium hydroxide; or an organic base such as sodium methoxide or sodium ethoxide.

A compound of formula (I) or an intermediate of formula (III), (IIIa) or (IIIb) containing a carboxy (—CO$_2$H) moiety may be converted into the corresponding compound containing an amide moiety by treatment with the appropriate amine in the presence of a condensing agent such as 1-ethyl-3-(3-dimethyl-aminopropyl)carbodiimide.

A compound of formula (I) or an intermediate of formula (III), (IIIa) or (IIIb) containing a carbonyl (C═O) moiety may be converted into the corresponding compound containing a —C(CH$_3$)(OH)— moiety by treatment with methylmagnesium bromide. Similarly, a compound of formula (I) or an intermediate of formula (III), (IIIa) or (IIIb) containing a carbonyl (C═O) moiety may be converted into the corresponding compound containing a —C(CF$_3$)(OH)— moiety by treatment with (trifluoromethyl)trimethylsilane and cesium fluoride. A compound of formula (I) containing a carbonyl (C═O) moiety may be converted into the corresponding compound containing a —C(CH$_2$NO$_2$)(OH)— moiety by treatment with nitromethane.

A compound of formula (I) or an intermediate of formula (III), (IIIa) or (IIIb) containing a hydroxymethyl moiety may be converted into the corresponding compound containing a formyl (—CHO) moiety by treatment with an oxidising agent such as Dess-Martin periodinane. A compound of formula (I) containing a hydroxymethyl moiety may be converted into the corresponding compound containing a carboxy moiety by treatment with an oxidising agent such as tetrapropylammonium perruthenate.

A compound of formula (I) or an intermediate of formula (III), (IIIa) or (IIIb) containing an aryl or an heteroaryl moiety may be transformed into the corresponding compound containing an aryl or heteroaryl moiety where a hydrogen atom has been substituted by a chloro or bromo substituent by reaction respectively with N-chlorosucciniide or N-bromosuccinimide, in a suitable solvent, e.g. dimethylformamide, according to methods known to the person skilled in the art.

A compound of formula (I) or an intermediate of formula (III), (IIIa) or (IIIb) containing an aryl moiety bearing a difluoromethoxy group may be transformed into the corresponding compound containing an aryl moiety where the difluoromethoxy group has been substituted by a hydroxy group, by reaction with sodiumbis(trimethylsilyl)amide, in a suitable solvent, e.g. THF, at low temperature.

A compound of formula (I) or an intermediate of formula (III), (IIIa) or (IIIb) containing an aryl or an heteroaryl moiety may be transformed into the corresponding compound containing an aryl or heteroaryl moiety where a hydrogen atom has been substituted by a trifluoromethyl substituent by reaction respectively with (i) trifluoroacetic acid in a suitable solvent, e.g. acetonitrile, (ii) addition of trifluoromethanesulphonyl chloride, followed by [4,4'-Bis(tert-butyl)-2,2'-bipyridine]bis[3,5-difluoro-2-[5-(trifluoromethyl)-2-pyridinyl]phenyl]iridium(III) hexafluorophosphate, according to conditions analogous to those described by McMillan ate al. in Nature, 2011, 480, 224.

It will be understood that any compound of formula (I) or an intermediate of formula (III), (IIIa) or (IIIb) initially obtained from any of the above processes may, where appropriate, subsequently be elaborated into a further compound of formula (I) or an intermediate of formula (III), (IIIa) or (IIIb) by techniques known from the art.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention. Alternatively the non desired enantiomer may be racemized into the desired enantiomer, in the presence of an acid or a base, according to methods known to the person skilled in the art, or according to methods described in the accompanying Examples.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3$^{rd}$ edition, 1999. The protecting groups may be removed at any convenient subsequent stage utilising methods known from the art.

Compounds in accordance with the present invention potently neutralise the activity of TNFα in a commercially available HEK-293 derived reporter cell line known as HEK-Blue™ CD40L. This is a stable HEK-293 transfected cell line expressing SEAP (secreted embryonic alkaline phosphatase) under the control of the IFNβ minimal promoter fused to five NF-κB binding sites. Secretion of SEAP by these cells is stimulated in a concentration-dependent manner by TNFα. When tested in the HEK-293 bioassay, also referred to herein as the reporter gene assay, compounds of the present invention exhibit an $IC_{50}$ value of 50 μM or less, generally of 20 μM or less, usually of 5 μM or less, typically of 1 μM or less, suitably of 500 nM or less, ideally of 100 nM or less, and preferably of 25 nM or less (the skilled person will appreciate that a lower $IC_{50}$ figure denotes a more active compound).

Certain compounds in accordance with the present invention potently inhibit the binding of a fluorescence conjugate to TNFα when tested in the fluorescence polarisation assay described herein. Indeed, when tested in that assay, compounds of the present invention exhibit an $IC_{50}$ value of 50 μM or less, generally of 20 μM or less, usually of 5 μM or less, typically of 1 μM or less, suitably of 500 nM or less, ideally of 100 nM or less, and preferably of 25 nM or less (as before, the skilled person will appreciate that a lower $IC_{50}$ figure denotes a more active compound).

The compounds of the Examples have been tested in one or both of the assays described below.

Fluorescence Polarisation Assay

Preparation of Compound (A)

1-(2,5-Dimethylbenzyl)-6-[4-(piperazin-1-ylmethyl)phenyl]-2-(pyridin-4-yl-methyl)-1H-benzimidazole—hereinafter referred to as "Compound (A)"—can be prepared by the procedure described in Example 499 of WO 2013/186229; or by a procedure analogous thereto.

Preparation of Fluorescence Conjugate

Compound (A) (27.02 mg, 0.0538 mmol) was dissolved in DMSO (2 mL). 5 (-6) Carboxy-fluorescein succinimyl ester (24.16 mg, 0.0510 mmol) (Invitrogen catalogue number: C1311) was dissolved in DMSO (1 mL) to give a bright yellow solution. The two solutions were mixed at room temperature, the mixture turning red in colour. The mixture was stirred at room temperature. Shortly after mixing a 20 μL aliquot was removed and diluted in a 80:20 mixture of AcOH:H$_2$O for LC-MS analysis on the 1200RR-6140 LC-MS system. The chromatogram showed two closely eluting peaks at retention times of 1.42 and 1.50 minutes, both with mass $(M+H)^+$=860.8 amu, corresponding to the two products formed with the 5- and 6-substituted carboxyfluorescein group. A further peak at retention time 2.21 minutes had a mass of $(M+H)^+$=502.8 amu, corresponding to Compound (A). No peak was observed for unreacted 5(-6) carboxyfluorescein succinimyl ester. The peak areas were 22.0%, 39.6% and 31.4% for the three signals, indicating a 61.6% conversion to the two isomers of the desired fluorescence conjugate at that time-point. Further 20 μL aliquots were extracted after several hours and then after overnight stirring, diluted as before and subjected to LC-MS analysis. The percentage conversion was determined as 79.8% and 88.6% respectively at these time-points. The mixture was purified on a UV-directed preparative HPLC system. The pooled purified fractions were freeze-dried to remove excess solvent. After freeze-drying, an orange solid (23.3 mg) was recovered, equivalent to 0.027 mmol of fluorescence conjugate, corresponding to an overall yield of 53% for the reaction and preparative HPLC purification.

Inhibition of Binding of Fluorescence Conjugate to TNFα

Compounds were tested at 10 concentrations starting from 25 μM in a final assay concentration of 5% DMSO, by pre-incubation with TNFα for 60 minutes at ambient temperature in 20 mM Tris, 150 mM NaCl, 0.05% Tween 20, before addition of the fluorescence conjugate and a further incubation for 20 hours at ambient temperature. The final concentrations of TNFα and the fluorescence conjugate were 10 nM and 10 nM respectively in a total assay volume of 25 μL. Plates were read on a plate reader capable of detecting fluorescence polarisation (e.g. an Analyst HT plate reader; or an Envision plate reader). An $IC_{50}$ value was calculated using XLfit™ (4 parameter logistic model) in ActivityBase.

When tested in the fluorescence polarisation assay, compounds of the accompanying Examples were found to exhibit $IC_{50}$ values of 50 μM or better.

When tested in the fluorescence polarisation assay, compounds of the accompanying Examples exhibit $IC_{50}$ values generally in the range of about 0.01 nM to about 50 μM, usually in the range of about 0.01 nM to about 20 μM, typically in the range of about 0.01 nM to about 5 μM, suitably in the range of about 0.01 nM to about 1 μM, ideally in the range of about 0.01 nM to about 500 nM, appositely in the range of about 0.01 nM to about 100 nM, and preferably in the range of about 0.01 nM to about 25 nM.

Reporter Gene Assay

Inhibition of TNFα-Induced NF-κB Activation

Stimulation of HEK-293 cells by TNFα leads to activation of the NF-κB pathway. The reporter cell line used to determine TNFα activity was purchased from InvivoGen. HEK-Blue™ CD40L is a stable HEK-293 transfected cell line expressing SEAP (secreted embryonic alkaline phosphatase) under the control of the IFNβ minimal promoter fused to five NF-κB binding sites. Secretion of SEAP by these cells is stimulated in a dose-dependent manner by TNFα, with an EC50 of 0.5 ng/mL for human TNFα. Compounds were diluted from 10 mM DMSO stocks (final assay concentration 0.3% DMSO) to generate a 10-point 3-fold serial dilution curve (30,000 nM to 2 nM final concentration, for example). Diluted compound was preincubated with TNFα for 60 minutes prior to addition to a 384-well microtitre plate and incubated for 18 h. The final TNFα concentration in the assay plate was 0.5 ng/mL. SEAP activity was determined in the supernatant using the colorimetric substrates QUANTI-Blue™ or HEK-Blue™ Detection media (InvivoGen). Percentage inhibitions for compound dilutions were calculated between a DMSO control and maximum inhibition (by excess control compound) and an $IC_{50}$ value calculated using XLfit™ (4 parameter logistic model) in ActivityBase.

When tested in the reporter gene assay, the compounds of the accompanying Examples were all found to exhibit $IC_{50}$ values of 50 μM or better.

When tested in the reporter gene assay, compounds of the accompanying Examples exhibit IC50 values generally in the range of about 0.01 nM to about 50 μM, usually in the range of about 0.01 nM to about 20 μM, typically in the range of about 0.01 nM to about 5 μM, usually in the range of about 0.01 nM to about 1 μM, suitably in the range of about 0.01 nM to about 500 nM, ideally in the range of about 0.01 nM to about 100 nM, and appositely in the range of about 0.01 nM to about 25 nM.

The following Examples illustrate the preparation of compounds according to the invention.

EXAMPLES

Abbreviations

| | | | |
|---|---|---|---|
| DCM: | Dichloromethane | EtOAc: | Ethyl acetate |
| DMF: | N,N-Dimethylformamide | MeOH: | Methanol |
| DMSO: | Dimethylsulfoxide | SiO2: | Silica |
| Et2O: | Diethyl ether | h: | Hour |
| THF: | Tetrahydrofuran | AcOH: | Acetic acid |
| r.t.: | Room temperature | b s.: | Broad singlet |
| M: | Mass | | |
| Brine: | Saturated aqueous sodium chloride solution | | |
| HPLC: | High Performance Liquid Chromatography | | |
| LCMS: | Liquid Chromatography Mass Spectrometry | | |
| ES+: | Electrospray Positive Ionisation | | |
| TEA: | Triethylamine | | |
| DIPEA: | N,N-di-iso-propylethylamine | | |
| DIAD: | Diisopropyl (E)-1,2-diazenedicarboxylate | | |
| RT: | retention time | | |
| TBAF: | tetrabutyl ammonium fluoride | | |
| TLC: | Thin Layer Chromatography | | |
| MeCN: | Acetonitrile | | |
| DIBAL-H: | Diisobutylaluminium hydride | | |
| TMSCN: | Trimethylsilyl cyanide | | |
| DEA: | Diethanolamine | | |
| pTSA | para-toluene sulphonic acid monohydrate | | |
| TFA: | trifluoroacetic acid | | |
| DMA: | dimethyl acetamide | | |
| HATU: | N-[(Dimethylamino)-1H-1,2,3-triazolo-[4,5-b]pyridin-1-ylmethylene]-N-ethylmethanaminium hexafluorophosphate N-oxide | | |
| KHMDS: | Potassium bis(trimethylsilyl)amide | | |
| COMU: | 1-Cyano-2-ethoxy-2-oxoethylidenaminooxy)dimethylamino-morpholino-carbenium hexafluorophosphate | | |

Analytical Conditions

All NMRs were obtained either at 300 MHz or 400 MHz.

All reactions involving air- or moisture-sensitive reagents were performed under a nitrogen atmosphere using dried solvents and glassware.

All compound LCMS data was determined by using the method below:

Method 1 for All Analytical LCMS Done in Basic Conditions: LCMS Basic:

A QDA Waters simple quadrupole mass spectrometer is used for LC-MS analysis.

This spectrometer is equipped with an ESI source and an UPLC Acquity Classic with diode array detector (210 to 400 nm.)

Data are acquired in a full MS scan from m/z 50 to 1000 in positive mode with an acidic elution The reverse phase separation is carried out at 45° C. on a Waters Acquity UPLC BEH C18 1.7 μm (2.1×50 mm) column for basic elution Gradient elution is performed with:

H2O/ACN/Ammonium_formate (95/5/63 mg/l)+50 μl NH4OH (solvent A)

ACN/H2O/Ammonium_formate (95/5/63 mg/l)+50 μl NH4OH (solvent B).

Gradient program:

HPLC flow rate: 0.6 ml/min to 0.7 ml/min, injection volume: 1 μl

Full flow in MS.

| Time (min) | A (%) | B (%) | Flow (ml/min) |
|---|---|---|---|
| 0 | 99 | 1 | 0.4 |
| 0.3 | 99 | 1 | 0.4 |
| 3.2 | 0 | 100 | 0.4 |
| 3.25 | 0 | 100 | 0.5 |
| 4 | 0 | 100 | 0.5 |

-continued

| Time (min) | A (%) | B (%) | Flow (ml/min) |
|---|---|---|---|
| 4.1 | 9 | 1 | 0.4 |
| 4.8 | 90 | 1 | 0.4 |

Method 2 for All Analytical LCMS in Acid Conditions:
LCMS Acid:

A QDA Waters simple quadrupole mass spectrometer is used for LC-MS analysis.

This spectrometer is equipped with an ESI source and an UPLC Acquity Hclass with diode array detector (210 to 400 nm).

Data are acquired in a full MS scan from m/z 50 to 1000 in positive mode with an acidic elution. The reverse phase separation is carried out at 45° C. on a Waters Acquity UPLC HSS T3 1.8 μm (2.1×50 mm) column for acidic elution
Gradient elution is performed with:
Water (solvent A)
Acetonitrile (solvent B)
Water/Acetonitrile/Formic Acid 0.5% (solvent C)
Gradient program:
HPLC flow rate: 0.6 ml/min to 0.7 ml/min, injection volume: 1 μl
Full flow in MS.

| Time (min) | A (%) | B (%) | C (%) | Flow (ml/min) |
|---|---|---|---|---|
| 0 | 90 | 0 | 10 | 0.6 |
| 0.3 | 90 | 0 | 10 | 0.6 |
| 3.2 | 0 | 90 | 10 | 0.6 |
| 3.25 | 0 | 90 | 10 | 0.7 |
| 4 | 0 | 90 | 10 | 0.7 |
| 4.1 | 90 | 0 | 10 | 0.6 |
| 5.4 | 90 | 0 | 10 | 0.6 |

Method 3
Instrument: Shimadzu 20AB
Column: Luna-C18(2) 2.0*50 mm, 5 μm
Column temperature: 40° C.
Mobile Phase A (MPA): $H_2O$+0.037% (v/v) TFA
Mobile Phase B (MPB): MeCN+0.018% (v/v) TFA
Flow rate: 0.8 mL/min (0.01-4.90 min), 1.2 mL/min (4.93-5.50 min)
Gradient ratios:

| Time (min) | MPA % | MPB % |
|---|---|---|
| 0.01 | 90 | 10 |
| 4.00 | 20 | 80 |
| 4.90 | 20 | 80 |
| 4.92 | 90 | 10 |
| 5.50 | 90 | 10 |

Detection (UV): 220 nm
Method 4
Instrument: Shimadzu LC-20AB analytical HPLC System
Column: Chiralcel OD-H, 250*4.6 mm i.d. 5 u
Mobile phase: A: n-hexane, and B: EtOH(0.05% IPA)
Gradient: A with 5% B
Flow rate: 1 mL/min
Column temperature: 35° C.

It will be apparent to the person skilled in the art that different retention times (RT) may be obtained for LCMS if different analytical conditions are used.

Preparative HPLC-MS Methods:
Method 1 Acidic Preparative LCMS
Waters Fraction-Lynx system, with 2545 pump, 2998 PDA, 2767 fraction collector and a
Waters 3100 MS
pH3_35_50 focused gradient, reverse phase
Waters XBridge Prep C18 OBD column, 19×100 mm, 5 μM
Solvent A: 10 mM ammonium bicarbonate+0.1% formic acid
Solvent B: MeCN+0.1% formic acid

| Time (mins) | % A | % B |
|---|---|---|
| 0 | 90 | 10 |
| 2.3 | 65 | 35 |
| 11 | 50 | 50 |
| 11.5 | 5 | 95 |
| 13 | 5 | 95 |
| 13.2 | 90 | 10 |

Flow Rate: 19 mL/min (+1 mL/min MeCN ACD)
Column temperature: Ambient
Method 2 Basic Preparative LCMS
Waters Fraction-Lynx system, with 2545 pump, 2998 PDA, 2767 fraction collector and a
Waters 3100 MS
pH10_35_30 focused gradient, reverse phase
Waters XBridge Prep C18 OBD column, 19×100 mm, 5 μM
Solvent A: 10 mM ammonium bicarbonate+0.1% NH4OH
Solvent B: MeCN+0.1% NH4OH

| Time (mins) | % A | % B |
|---|---|---|
| 0 | 90 | 10 |
| 2.3 | 65 | 35 |
| 11 | 50 | 50 |
| 11.5 | 5 | 95 |
| 13 | 5 | 95 |
| 13.2 | 90 | 10 |

Flow rate: 19 mL/min (+1 mL/min MeCN ACD)
Column temperature: Ambient.

Intermediate 1

(N,E)-N-[[2-bromo-6-(difluoromethoxy)phenyl]methylene]-2-methyl-propane-2-sulfinamide To a stirred solution of 2-bromo-6-(difluoromethoxy)benzaldehyde (30 Kg, 119.5 mol) in THF (133.5 kg) in a 300 L reactor at 10-20° C. was added (S)-(+)-2-methyl-2-propanesulfinamide (15.9 Kg, 131.5 mol), followed by the slow addition of $Ti(OEt)_4$ (40.9 Kg, 179.3 mol) at 10-35° C. (Note: Addition was exothermic, temperature kept below 40° C.). The reaction mixture was stirred at 30-40° C. for 18 hours (until reaction complete by HPLC). Water (42.9 kg) and EtOAc (270.6 kg) was then added into the reactor (copious solid formed), followed by celatom (9.0 kg), the mixture was filtered and the filtered cake and filtrate obtained. The filtered cake was washed with EtOAc (2×405.9 kg) and the combined filtrate washed with water (128.7 kg) and saturated aqueous brine solution (128.7 kg), the combined organic layers were concentrated in vacuo to provide the title compound (40.5 kg, yield, 95.7%) as a brown oil, which was used in the next step without further purification. HPLC: Method 3 RT 3.48 minutes.

Intermediate 2

Ethyl 3-[2-bromo-6-(difluoromethoxy)phenyl]-3-[[(S)-tert-butylsulfinyl]amino]propanoate To a 1000 L reactor was added anhydrous THF (324.4 kg) followed by Zn (52.3 kg, 800.4 mol) and CuCl (17 kg, 171.5 mol) at 15-20° C. under $N_2$. The reaction mixture was warmed to 60-70° C. under $N_2$ and stirred for 1-2 hours. The reaction mixture was then cooled to 20-30° C. and ethyl 2-bromoacetate (47.7 kg, 285.9 mol) added under $N_2$. (Note: Ethyl 2-bromoacetate should be slowly added within 2-4 h. The addition is exothermic, temperature to be kept below 40° C.). The reaction mixture is then stirred at 50-60° C. for 1-2 h under $N_2$, before being cooled to 0-10° C. and Intermediate 1 (40.5 kg, 114.3 mol) in anhydrous THF (36.05 kg) was added to the mixture. (Note: Addition was exothermic, temperature kept below 10° C.). The reaction mixture was then warmed to 20-30° C. and stirred for 1-2 h under $N_2$ (until reaction complete, monitored by HPLC). Tert-butyl methyl ether (179.8 kg) and a solution of citric acid (40.5 kg) in water (243 kg) was then added into the reactor at 20-30° C. The layers were separated and the aqueous phase extracted with tert-butyl methyl ether (179.8 kg). The combined organics were washed with water (101.3 kg), saturated aqueous $NaHCO_3$ solution (243 kg) and saturated aqueous brine solution (101.3 kg) and concentrated in vacuo to the title compound (47.0 kg, 92.9%) as brown oil, which was used for the next step without further purification. HPLC: Method 3 RT 3.33 minutes.

Intermediate 3

Ethyl 3-amino-3-[2-bromo-6-(difluoromethoxy)phenyl]propanoate

To a stirred solution of Intermediate 2 (47.0 Kg, 106.3 mol) and EtOAc (42.4 kg) in a 500 L reactor at 15-25° C. was added HCl/EtOAc (4 M, 100 kg). (Note: Addition was exothermic, temperature kept below 40° C., 4M HCl/EtOAc solution made by adding HCl (15.5 kg, 425 mol) into EtOAc (84.8 kg) at −70 to −50° C.) Reaction monitored by TLC until the materials were consumed. The mixture was stirred at 20° C. for 1 h with nitrogen advocating. The reaction mixture was extracted with water (4×117.5 kg) and the combined aqueous layers adjusted to pH 8-9 with $Na_2CO_3$ (47.0 kg) and extracted with EtOAc (2×254.4 kg). The combined organic layers were washed with a saturated aqueous solution of brine (117.5 kg) and concentrated under vacuum to provide the title compound (34 kg, 94.7%) as brown oil. HPLC: Method 3 RT 1.69 minutes.

Intermediate 4

Ethyl (3R)-3-amino-3-[2-bromo-6-(difluoromethoxy)phenyl]propanoate

To a stirred solution of Intermediate 3 (34 kg, 100.6 mol) in tert-butyl methyl ether (151 kg) in a 50 L reactor at 50-60° C. was added (S)-Mandelic acid (15.3 kg, 100.6 mol) portionwise and the reaction mixture stirred at 50-60° C. for 1 hour before being cooled to 10-20° C. The mixture was filtered and filter cake and filtrate obtained. The filtered cake and tert-butyl methyl ether (62.9 kg) were added to the reactor and the mixture was stirred at 15-20° C. for 30 minutes and then filtered. The filter cake was dissolved in water (340 kg) and the aqueous solution was adjusted to pH 8-9 with $NaHCO_3$ (34 kg) and extracted with EtOAc (2×184 kg). The combined organic phases were washed with a saturated aqueous solution of brine (68 kg) and concentrated under vacuum to provide the title compound (22 kg, 64.7%) as brown oil, which was used in the next step without further purification. HPLC: Method 3 RT 1.71 minutes. and HPLC: Method 4 3.11 minutes.

Intermediate 5

Ethyl (3R)-3-[2-bromo-6-(difluoromethoxy)phenyl]-3-(5-chloro-2-nitro-anilino)propanoate To a 20 L reactor with overhead stirring was added Intermediate 4 (6.5 kg, 19.22 mol), DIPEA (3.10 kg, 24.03 mol) and 4-chloro-2-fluoro-1-nitro-benzene (3.14 kg, 17.87 mol) at 15-25° C. The reaction mixture was heated to 75-90° C. for 4 hours (until the reaction is complete as monitored by HPLC). The reaction mixture was cooled to 20-25° C. and EtOAc (15 L) added and reaction mixture transferred to a 50 L reactor. A solution of citric acid (3.25 kg) in water (19 L) was then added and the reaction mixture was stirred for 30 minutes. The layers were separated and the aqueous phase extracted with EtOAc (15 L), the combined organics were washed with brine (2×15 L) and concentrated under vacuum to provide the title compound (8.10 Kg, 85%) as yellow solid. The crude product was used for the next step without further purification. HPLC: Method 3 RT 4.33 minutes.

Intermediate 6

(3R)-3-[2-bromo-6-(difluoromethoxy)phenyl]-3-(5-chloro-2-nitro-anilino)propanal

To a 50 L three-necked, round bottom reactor with overhead stirring was added THF (6 L) and Intermediate 5 (3.0 kg, 6.08 mol) at 10-20° C. The reaction mixture was then cooled to −65 to −75° C. (dry ice-acetone bath) and then DIBAL-H (1 M, 12.16 L) added slowly in portions at −65 to −75° C. (Note: Addition was exothermic, temperature kept below −60° C.). The reaction was then stirred below −60° C. for 1 hour (until the reaction was complete, monitored by HPLC and TLC). Saturated aqueous $NH_4Cl$ solution (12 L) was added into the reactor slowly over 1-2 hours at −65 to −70° C. (Note: Addition was exothermic and temperature was kept below −40° C.). Water (6 L) then added into the reactor slowly over 30 minutes at −50 to −40° C. (Note: Addition was exothermic, reaction temperature was kept below −15° C.). The quenched reaction mixture was transferred into 6×25 L reactors, water (3 L) and EtOAc (5 L) was added to each reactor and the mixtures stirred. (Note: Stirred mixture is exothermic and the temperature will rise, allow the temperature of the mixture to rise slowly.) When the temperature rose to 8 to 10° C. a solid was detected, celatom (500 g) was added to each reactor, and the mixtures stirred for a further 30 minutes. The mixtures were filtered, and the filter cake and filtrate obtained. The filter cake was washed with EtOAc (3×20 L) and the filtrate collected. The combined filtrate was separated, and the organic layer washed with brine (10 L) and concentrated in vacuo to give the crude product. The crude product was purified by column chro-

Intermediate 7

(3R)-3-[2-bromo-6-(difluoromethoxy)phenyl]-3-(5-chloro-2-nitro-anilino)propanal

To a 10 L three-necked, round bottom reactor was added THF (1 L) and Intermediate 6 (500 g, 1.01 mol), which slowly dissolved at 10-20° C. (overhead stirring used). The reaction mixture was then cooled to −65 to −75° C. (dry ice-acetone bath), DIBAL-H (1 M solution in THF, 2.03 L) added slowly in portions at −65 to −75° C. (Note: DIBAL-H should be slowly added within 2-3 h. Addition is exothermic, keep the reaction temperature below −60° C.). After addition, the reaction mixture was stirred below −60° C. for 1 h (until reaction was complete as monitored by HPLC and TLC). Saturated aqueous NH$_4$Cl solution (2.0 L) was added to the reactor slowly at −65 to −70° C. (Note: saturated NH$_4$Cl solution should be slowly added within 1-2 h. Addition is exothermic, keep the reaction temperature below −40° C.). Water (1.0 L) was added into the reactor slowly at −50 to −40° C. (Note: water should be slowly added within 30 mins. Addition is exothermic, keep the reaction temperature below −15° C.). The quenched reaction mixture was transferred into a 25 L reactor, water (3 L) and EtOAc (5 L) added and the mixture stirred (overhead stirring used) for 3 hours. (Note: Stirred mixture is exothermic and the temperature will rise, allow the temperature of the mixture to rise slowly.) When the temperature rises to 8 to 10° C. a solid was detected. EtOAc (2 L) and celatom (500 g) was added, and mixture stirred for a further 30 mins. Mixture was split off and a filter cake and filtrate obtained. The filter cake was washed with EtOAc (3×3 L). Combined filtrates were separated, and the organic layer washed with brine (10 L) and concentrated to give the crude product. The crude product was purified by column chromatography (SiO$_2$, hexanes/EtOAc 10:1 to 2:1) to obtain the title compound (370 g, 81.3% yield) as a yellow oil.

$^1$H NMR (400 MHz, CDCl$_3$) δ 9.82 (s, 1H), 8.85 (d, J8 Hz, 1H), 8.09 (d, J9.2 Hz, 1H), 7.46-7.48 (m, 1H), 7.11-7.20 (m, 3H), 6.68 (t, J 72 Hz, 1H), 6.63 (dd, J 9.2, 2.0 Hz, 1H), 5.93-5.95 (m, 1H), 3.50 (dd, J 17.6, 8.4 Hz, 1H), 3.08 (d, J 17.2 Hz).

Intermediate 8

(4R)-4-[2-bromo-6-(difluoromethoxy)phenyl]-4-(5-chloro-2-nitro-anilino)-2-trimethylsilyloxy-butanenitrile To a 50 L three-necked, round bottom reactor was added DCM (18 L), followed by Intermediate 7 (2 kg, 4.45 mol) keeping the temperature below 30° C. ZnI$_2$ (142 g, 0.445 mol) slowly added, followed by TEA (45 g, 0.445 mol) into the reactor at 25-30° C. TMSCN (883 g, 8.90 mol) in DCM (2 L) was then added, keeping the temperature below 30° C. The reaction mixture was then stirred for 17 hours (until the reaction was complete as monitored by HPLC and TLC). Water (10 L) was added to quench the reaction at 25-30° C. The layers were separated and the aqueous phase extracted with DCM (4 L).

Combined organic layers were washed with water (4 L) and brine (4 L). The organic layer was concentrated under vacuum to provide the title compound (2.3 kg) as a red liquid without further purification.

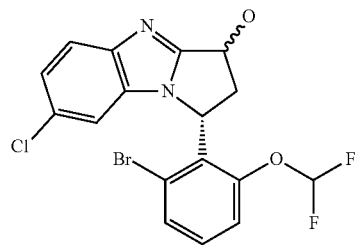 [SMILES: OC1C[C@H](c2c(Br)cccc2OC(F)F)n2c1nc1ccc(Cl)cc12]

Intermediate 9

(1R)-7-chloro-1-[2-bromo-6-(difluoromethoxy)phenyl]-2,3-dihydro-1H-pyrrolo[1,2-a]benzimidazol-3-ol To a 50 L reactor was added EtOH (26.4 L), followed by Intermediate 8 (2.2 kg, 4 mol) and SnCl$_2$ (3.8 kg, 20 mol) at 25-30° C. The temperature of the reaction mixture was warmed to 90-110° C. and stirred for 12 hours (overhead stirring used) until all the starting material was consumed (monitored hourly by HPLC). The reaction mixture was cooled to 25-30° C. Ice water (26.4 L) was added to the reactor, keeping the temperature below 30° C. The mixture was basified to pH 8-9 using 1N NaOH (30 L), again keeping the temperature below 30° C. The mixture was then diluted with DCM (26.4 L) and filtered through celite, the cake washed with DCM (2×15 L). The filtrate was then transferred into a 50 L reactor and the layers separated. The aqueous phase was extracted with DCM (15 L). Combined organics were washed with sat. aq. NaCl solution (15 L) and then concentrated under vacuum to provide the crude product as a brown solid. The crude was washed with hexanes/EtOAc (4.4 L, 4/1) and filtered to provide the title compound (959 g, 56%) as a light yellow solid.

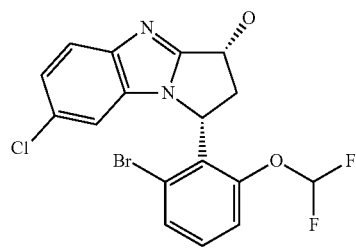

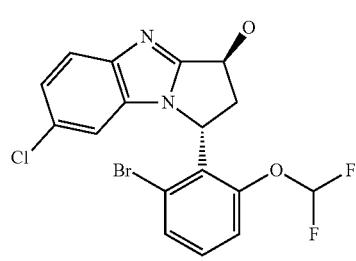

Intermediate 10 and 11

(1R,3R)-7-chloro-1-[2-bromo-6-(difluoromethoxy)phenyl]-2,3-dihydro-1H-pyrrolo[1,2-a]benzimidazol-3-ol and (1R,3S)-7-chloro-1-[2-bromo-6-(difluoromethoxy)phenyl]-2,3-dihydro-1H-pyrrolo[1,2-a]benzimidazol-3-ol Intermediate 9 (958.1 g) was separated by SFC to give Intermediate 10 (360 g) and Intermediate 11 (385 g), both obtained as light yellow solids.
Separation Conditions:
  Instrument: Thar 350 preparative SFC (SFC-6),
  Column: ChiralCel OD-10 u, 300×50 mmI·D.
  Mobile phase: A: $CO_2$ and B: Methanol
  Gradient: B 30%, Flow rate: 200 mL/min, Back pressure: 100 bar, Column temperature: 38° C.
  Wavelength: 220 nm, Cycle time: ~6.9 min
  Sample preparation: 100 g compound dissolved in 3 L Methanol/DCM and filtered
  Injection: 14 ml per injection.
  Intermediate 11—RT 5.24 min; (LCMS (ES+) RT 2.90 mins, 429/431 (M+H)$^+$)
  Intermediate 10—RT 6.19 min.

Intermediate 12

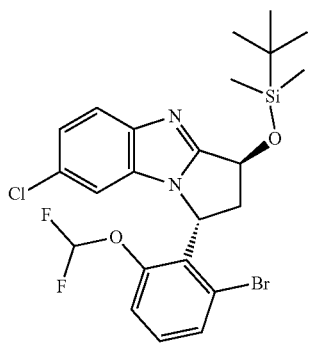 [SMILES: CC(C)(C)[Si](C)(C)O[C@H]1C[C@H](c2c(Br)cccc2OC(F)F)n2c1nc1ccc(Cl)cc12]

(1R,3S)-1-[2-bromo-6-(difluoromethoxy)phenyl]-3-{[tert-butyl(dimethyl)silyl]oxy}-7-chloro-2,3-dihydro-1H-pyrrolo[1,2-a]benzimidazole To a solution of Intermediate 11 (20 g, 46.6 mmol) in DMF (120 mL) were added successively imidazole (3.96 g, 58.2 mmol) and tert-butyldimethylchlorosilane (8.32 g, 53.5 mmol). The reaction was allowed to stir at r.t. overnight. To the reaction mixture was added cold water (200 mL) and the mixture extracted with diethyl ether (3×100 mL). The combined organic layers were washed with brine (100 mL), dried over anhydrous magnesium sulphate, filtered and concentrated in vacuo to afford the title compound (25.16 g, 99%) as a white solid. LCMS Method 1 (ES+) RT 3.47 min, 543/545/547 (M+H)$^+$.

Intermediate 13

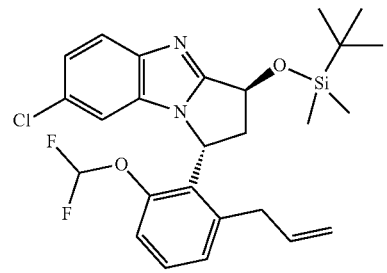 [SMILES: C=CCc1cccc(OC(F)F)c1[C@H]1C[C@H](O[Si](C)(C)C(C)(C)C)c2nc3ccc(Cl)cc3n21]

(1R,3S)-3-{[tert-butyl(dimethyl)silyl]oxy}-7-chloro-1-[2-(difluoromethoxy)-6-(prop-2-en-1-yl)phenyl]-2,3-dihydro-1H-pyrrolo[1,2-a]benzimidazole Intermediate 12 (5 g, 9.2 mmol), allyltributyltin (3.5 ml, 11.0 mmol), bis(triphenylphosphine)palladium(II) dichloride (323 mg, 0.46 mmol) and LiCl (1.17 g, 27.6 mmol) were suspended in dry toluene (100 mL). The reaction mixture was heated at reflux overnight under an argon atmosphere. The reaction mixture was diluted with EtOAc and water. The two phases were separated and the aqueous layer further extracted with EtOAc. The combined organic extracts were washed with brine, dried over magnesium sulphate, filtered and concentrated under reduced pressure. The crude was purified by chromatography ($SiO_2$, 5% EtOAc in heptane) to give the title compound (3.98 g, 86%) as a colorless oil. LCMS Method 1 (ES+) RT 5.84 min, 505 (M+H)$^+$. $^1$H NMR (400 MHz, CDCl$_3$) δ 7.68 (d, J8.6 Hz, 1H), 7.33 (t, J8.0 Hz, 1H), 7.18 (dd, J 7.7, 1.2 Hz, 1H), 7.12 (dd, J8.7, 2.1 Hz, 1H), 6.91 (dt, J8.2, 1.4 Hz, 1H), 6.59 (d, J2.1 Hz, 1H), 6.13-6.00 (m, 1H), 5.94 (dd, J 8.2, 6.3 Hz, 1H), 5.71 (dd, J 76.7, 70.2 Hz, 1H), 5.46 (dd, J7.3, 2.3 Hz, 1H), 5.22 (dq, J 10.4, 1.5 Hz, 1H), 5.05 (dq, J 17.1, 1.6 Hz, 1H), 3.80 (ddt, J16.1, 6.4, 1.7 Hz, 1H), 3.65 (ddt, J 16.3, 5.6, 1.8 Hz, 1H), 3.15 (ddd, J 13.6, 7.3, 6.3 Hz, 1H), 2.86 (ddd, J 13.8, 8.2, 2.4 Hz, 1H), 0.95 (s, 9H), 0.28 (s, 3H), 0.20 (s, 3H).

Intermediate 14

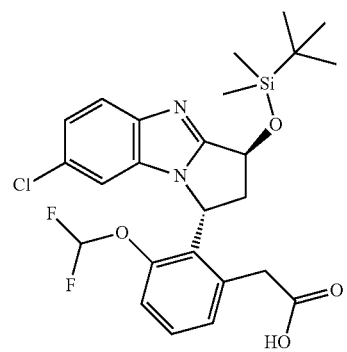 [SMILES: CC(C)(C)[Si](C)(C)O[C@H]1C[C@H](c2c(CC(=O)O)cccc2OC(F)F)n2c1nc1ccc(Cl)cc12]

{2-[(1R,3S)-3-{[tert-butyl(dimethyl)silyl]oxy}-7-chloro-2,3-dihydro-1H-pyrrolo[1,2-a]benzimidazol-1-yl]-3-(difluoromethoxy)phenyl}acetic acid Intermediate 13 (3.75 g, 7.42 mmol) was dissolved in EtOAc (18 mL), acetonitrile (18 mL) and water (27 mL).

Sodium periodate (8.02 g, 37.1 mmol) followed by ruthenium(II) chloride (154 mg, 0.74 mmol) was then added and the reaction mixture stirred overnight at room temperature. The reaction mixture was diluted with EtOAc and water. The two phases were separated and the aqueous layer further extracted with EtOAc. The combined organic extracts were washed with brine, dried over magnesium sulphate, filtered and concentrated under reduced pressure.

The crude residue was purified by chromatography (SiO$_2$, 20-50% EtOAc in hexane) to give the title compound (2.12 g, 55%). LCMS Method 1 (ES+) RT 2.19 min, 523 (M+H)$^+$.

$^1$H NMR (400 MHz, CDCl$_3$) δ 7.69 (d, J8.7 Hz, 1H), 7.34 (t, J8.0 Hz, 1H), 7.21 (dd, J 7.8, 1.2 Hz, 1H), 7.09 (dd, J8.7, 2.0 Hz, 1H), 6.96 (d, J8.2 Hz, 1H), 6.77 (d, J2.0 Hz, 1H), 5.97 (dd, J 8.3, 6.0 Hz, 1H), 5.73 (dd, J 75.9, 70.3 Hz, 1H), 5.49 (dd, J 7.5, 2.5 Hz, 1H), 3.98 (q, J 16.3 Hz, 2H), 3.16 (ddd, J 13.6, 7.5, 6.1 Hz, 1H), 2.95 (ddd, J 13.9, 8.3, 2.5 Hz, 1H), 0.90 (s, 9H), 0.22 (s, 3H), 0.16 (s, 3H).

Intermediate 15

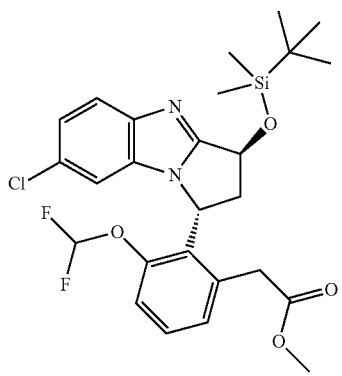 [SMILES: COC(=O)Cc1cccc(OC(F)F)c1[C@H]1C[C@H](O[Si](C)(C)C(C)(C)C)c2nc3ccc(Cl)cc3n21]

Methyl {2-[(1R,3S)-3-{[tert-butyl(dimethyl)silyl]oxy}-7-chloro-2,3-dihydro-1H-pyrrolo[1,2-a]benzimidazol-1-yl]-3-(difluoromethoxy)phenyl}acetate To a solution of Intermediate 14 (2.04 g, 3.90 mmol) in DCM (10 mL) and MeOH (2 mL) at 0° C. was added drop wise a solution of 2M (trimethylsilyl)-diazomethane in hexane (2.3 mL, 4.67 mmol). After 30 minutes a few drops of acetic acid was added to neutralize the excess diazomethane. The reaction mixture was diluted with DCM and water. The two phases were separated and the aqueous layer further extracted with DCM. The combined organic extracts were washed with brine, dried over magnesium sulphate, filtered and concentrated under reduced pressure to afford the title compound (quantitative yield). The material was used in the next step without further purification. LCMS Method 1 (ES+) RT 3.27 min, 537 (M+H)$^+$.

Intermediate 16

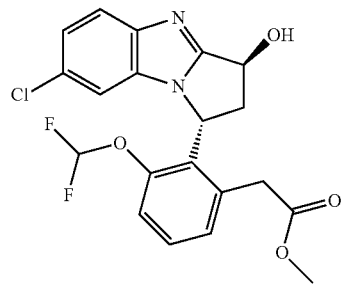 [SMILES: COC(=O)Cc1cccc(OC(F)F)c1[C@H]1C[C@H](O)c2nc3ccc(Cl)cc3n21]

Methyl {2-[(1R,3S)-7-chloro-3-hydroxy-2,3-dihydro-1H-pyrrolo[1,2-a]benzimidazol-1-yl]-3-(difluoromethoxy)phenyl}acetate To a solution of Intermediate 15 (3.9 mmol) in MeOH (40 mL) was added p-Toluenesulfonic acid monohydrate (3.7 g, 19 mmol) and the slurry was stirred overnight at r.t. The reaction mixture was diluted with EtOAc and sat. aq. NaHCO$_3$ solution. The two phases were separated and the aqueous layer extracted with EtOAc. The combined organic extracts were dried over magnesium sulphate, filtered and concentrated under reduced pressure to afford the title compound (quantitative yield) used in the next step without further purification. LCMS Method 1 (ES+) RT 2.31 min, 423 (M+H)$^+$.

Intermediate 17

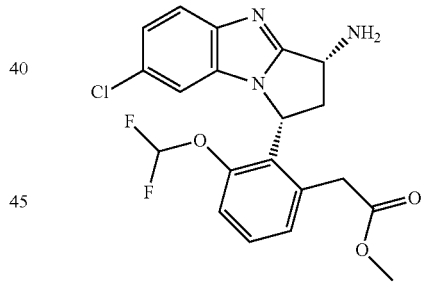

Methyl {2-[(1R,3R)-3-amino-7-chloro-2,3-dihydro-1H-pyrrolo[1,2-a]benzimidazol-1-yl]-3-(difluoromethoxy)phenyl}acetate To a suspension of Intermediate 16 (1.85 g, 4.37 mmol) in THF (18 mL) at 0° C. was added diphenylphosphoryl azide (1.27 mL, 5.69 mmol), followed by 1,8-diazabicyclo[5.4.0]undec-7-ene (915 µL, 6.12 mmol). The reaction mixture was allowed to warm to r.t. and stirred at r.t for 2 hour before being heated at 50° C. for 18 hours. The reaction was then cooled at 0° C. and water (1.8 mL) was added followed by the drop wise addition of trimethylphosphine (1M in toluene, 8.7 mL, 8.7 mmol). The reaction was allowed to warm to r.t. and stirred for 2 hours. The volatiles were concentrated in vacuo and the residue diluted with water and EtOAc. The two phases were separated and the organic layer further washed with sat. aq. NaHCO$_3$ solution, brine, dried over magnesium sulphate, filtered and concentrated under reduced pressure. The crude residue was purified by chromatography (SiO$_2$, 4% MeOH in DCM) to give the title compound (1.18 g, 64% yield) as a white solid. LCMS Method 1 (ES+) RT 2.13 min, 422 (M+H)$^+$.

Intermediate 18

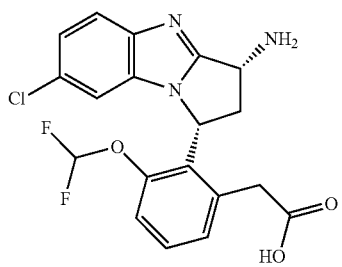 [SMILES: N[C@@H]1C[C@H](c2c(CC(=O)O)cccc2OC(F)F)n2c1nc1ccc(Cl)cc12]

{2-[(1R,3R)-3-amino-7-chloro-2,3-dihydro-1H-pyrrolo[1,2-a]benzimidazol-1-yl]-3-(difluoromethoxy)phenyl}acetic acid To a solution of Intermediate 17 (570 mg, 1.35 mmol) in THF (4 mL) and water (1 mL) at 0° C. was added lithium hydroxide monohydrate (64 mg, 1.50 mmol). After 10 minutes, the slurry was allowed to warm to r.t. and stirred for 3 hours. The reaction mixture was concentrated in vacuo and the residue taken up into a mixture of 1,4 dioxane (4 mL) and water (1 mL). The suspension was cooled to 0° C. and hydrochloric acid (405 µl, 1.62 mmol) added slowly. The reaction mixture was allowed to warm to r.t. and stirred for 10 minutes. After this time the mixture was evaporated to afford the title compound which was used in the next step without further purification. LCMS Method 1 (ES+) RT 1.52 min, 408 (M+H)$^+$.

Intermediate 19

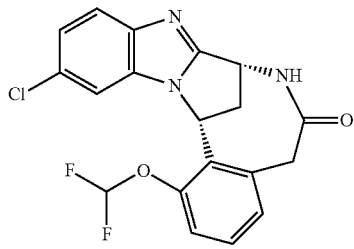 [SMILES: O=C1Cc2cccc(OC(F)F)c2[C@H]2C[C@@H](N1)c1nc3ccc(Cl)cc3n12]

(8R,15R)-12-chloro-1-(difluoromethoxy)-5,7,8,15-tetrahydro-6H-8,15-methanobenzimidazo[1,2-b][2,5]benzodiazonin-6-one The title compound was prepared following either of the two procedures described below:
Procedure 1: Cyclisation of Intermediate 18:
To a solution of Intermediate 18 (50 mg, 0.104 mmol) and COMU (56 mg, 0.126 mmol) in DMF (1 mL) at 0° C. was added N,N-diisopropylethylamine (73 µL, 0.42 mmol). The reaction mixture was allowed to warm to r.t. and stirred overnight. The reaction mixture was then diluted with EtOAc and water. The two phases were separated and the aqueous layer further extracted with EtOAc. The combined organic extracts were washed with brine, dried over magnesium sulphate, filtered and concentrated under reduced pressure. The crude compound was purified by preparative LC-MS (basic conditions) to give the title compound (5.5 mg, 14%). LCMS Method 1 (ES+) RT 3.95 min, 390 (M+H)$^+$.

Procedure 2: Cyclisation of Intermediate 17:
Intermediate 17 (20 mg, 0.047 mmol) was dissolved in dry DCM (2 mL), trimethylaluminium (80 µl, 0.191 mmol) was added at room temperature and then heated at 50° C. for 2 hours. The reaction mixture was then diluted with DCM and 0.1 N HCl. The mixture was stirred for 5 minutes and then basified with sat. aq. NaHCO$_3$ solution. The two phases were separated and the aqueous layer further extracted with DCM. The combined organic extracts dried over magnesium sulphate, filtered and concentrated under reduced pressure. The crude material was purified by preparative LC-MS basic conditions to give the title compound (13 mg, 70%). LCMS Method 1 (ES+) RT 3.95 min, 390 (M+H)$^+$.
$^1$H NMR (400 MHz, CDCl$_3$) δ 7.75 (d, J8.7 Hz, 1H), 7.33-7.26 (m, 2H), 7.20 (d, J 8.2 Hz, 1H), 7.17 (d, J 1.9 Hz, 1H), 7.12 (dd, J 7.5, 1.2 Hz, 1H), 6.71 (t, J 73.3 Hz, 1H), 6.50 (d, J7.0 Hz, 1H), 6.33 (d, J8.8 Hz, 1H), 4.93 (t, J7.5 Hz, 1H), 3.54 (dt, J14.0, 8.5 Hz, 1H), 3.06 (dd, J 13.8, 1.3 Hz, 1H), 2.48 (d, J 14.0 Hz, 1H), 1.72 (d, J 13.7 Hz, 1H).

Intermediate 20

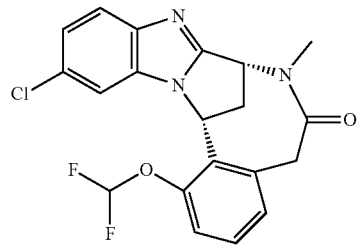 [SMILES: CN1C(=O)Cc2cccc(OC(F)F)c2[C@H]2C[C@@H]1c1nc3ccc(Cl)cc3n12]

(8R,15R)-12-chloro-1-(difluoromethoxy)-7-methyl-5,7,8,15-tetrahydro-6H-8,15-methanobenzimidazo[1,2-b][2,5]benzodiazonin-6-one To a solution of Intermediate 19 (13 mg, 0.03 mmol) in DMF (0.5 ml) at 0° C. was added sodium hydride (1.6 mg, 0.04 mmol, 60 mass %). The reaction was allowed to warm to r.t. and stirred for 15 minutes. Iodomethane (4 µl, 0.064 mmol) was then added and the reaction mixture stirred for 2 hours. The reaction mixture was then diluted with EtOAc and water, the two phases were separated and the aqueous layer further extracted with EtOAc. The combined organic extracts were washed with brine, dried over magnesium sulphate, filtered and concentrated under reduced pressure. The crude material was purified by preparative LC-MS basic conditions to give the title compound (9.7 mg, 73%). LCMS Method 1 (ES+) RT 4.19 min, 404 (M+H)$^+$. $^1$H NMR (400 MHz, CDCl$_3$) δ 7.74 (dd, J8.7, 0.6 Hz, 1H), 7.31-7.26 (m, 2H), 7.20-7.15 (m, 2H), 7.13 (dd, J7.6, 1.3 Hz, 1H), 6.70 (t, J73.3 Hz, 1H), 6.32 (d, J8.8 Hz, 1H), 4.96 (d, J8.3 Hz, 1H), 3.54 (dt, J 13.8, 8.5 Hz, 1H), 3.17 (s, 3H), 3.12 (d, J 14.0 Hz, 1H), 2.43 (d, J 14.1 Hz, 1H), 1.74 (d, J 14.0 Hz, 1H).

Intermediate 21

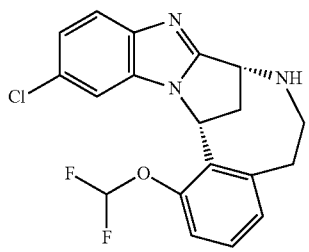 [SMILES: FC(F)Oc1cccc2c1[C@H]1C[C@@H](NCC2)c2nc3ccc(Cl)cc3n21]

(8R,15R)-12-chloro-1-(difluoromethoxy)-5,7,8,15-tetrahydro-6H-8,15-methanobenzimidazo[1,2-b][2,5]benzodiazonine To a solution of Intermediate 19 (33.6 mg, 0.086 mmol) in anhydrous THF (1.5 mL) at 0° C. was added lithium aluminium hydride (5.2 mg, 0.13 mmol), the reaction mixture was then allowed to warm to r.t. and stirred overnight. The reaction mixture was then diluted with EtOAc and water, the two phases were separated and the aqueous layer further extracted with EtOAc. The combined organic extracts were washed with brine, dried over magnesium sulphate, filtered and concentrated under reduced pressure. The crude material was purified by preparative LC-MS basic conditions to give the title compound (13 mg, 39%). LCMS Method 1 (ES+) RT 2.42 min, 376 (M+H)+.

Intermediate 22

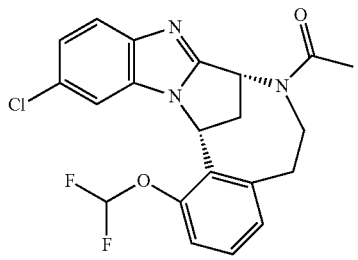 [SMILES: CC(=O)N1CCc2cccc(OC(F)F)c2[C@H]2C[C@@H]1c1nc3ccc(Cl)cc3n12]

1-[(8R,15R)-12-chloro-1-(difluoromethoxy)-5,15-dihydro-6H-8,15-methanobenzimidazo[1,2-b][2,5]benzodiazonin-7(8H)-yl]ethanone To a solution of Intermediate 21 (13 mg, 0.034 mmol) in DCM (0.5 mL) was added acetic anhydride (7.1 mg, 0.068 mmol) followed by pyridine (8.1 mg, 0.10 mmol) and the mixture stirred at r.t for 2 hours. The reaction mixture was then diluted with DCM and sat. aq. NH4Cl solution, the two phases were separated and the organic layer further washed with sat. aq. NaHCO3 solution, brine, dried over magnesium sulphate, filtered and concentrated under reduced pressure to afford the title compound which was used without further purification LCMS Method 1 (ES+) RT 2.45 min, 418 (M+H)+.

Example 1

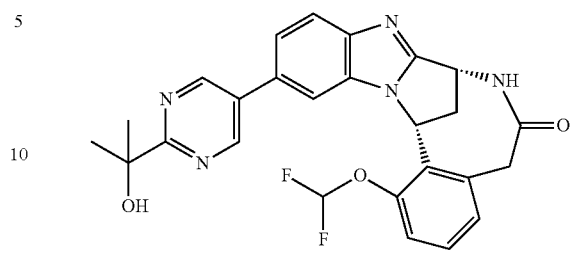

(8R,15R)-1-(difluoromethoxy)-12-[2-(2-hydroxypropan-2-yl)pyrimidin-5-yl]-5,7,8,15-tetrahydro-6H-8,15-methanobenzimidazo[1,2-b][2,5]benzodiazonin-6-one Intermediate 19 (17 mg, 0.044 mmol), 2-[5-(4,4,5,5-tetramethyl-1,3,2-dioxaborolan-2-yl)pyrimidin-2-yl]propan-2-ol (29 mg, 0.11 mmol), potassium phosphate tribasic (24 mg, 0.11 mmol), tricyclohexylphosphonium tetrafluoroborate (2 mg, 0.0054 mmol) and tris(dibenzylideneacetone)dipalladium(0) (2 mg, 0.0022 mmol), were placed in a reaction tube, which was subsequently filled with argon. Degassed 1,4 dioxane (0.5 mL) and water (0.05 ml) were added and the resulting slurry was stirred for 3 hours at 125° C. The reaction mixture was cooled to r.t. before addition of EtOAc and water. The two phases were separated and the aqueous layer extracted with EtOAc, the combined organic extracts were dried over magnesium sulphate, filtered and concentrated under reduced pressure. The crude material was purified by preparative LC-MS basic conditions, followed by SFC separation employing an 2-ethylpyridine column 5 µ eluting with 15% EtOH in CO2, to afford the title compound (5 mg, 22%) as a white solid. LCMS Method 1 (ES+) RT 3.44 min, 492 (M+H)+. LCMS Method 2 (ES+) RT 3.56 min, 492 (M+H)+.

1H NMR (400 MHz, CDCl3) δ 8.87 (s, 2H), 7.99 (d, J8.5 Hz, 1H), 7.52 (d, J 8.3 Hz, 1H), 7.36 (s, 1H), 7.28 (d, J 11.6 Hz, 1H), 7.21 (d, J 8.1 Hz, 1H), 7.13 (d, J7.6 Hz, 1H), 6.74 (t, J73.3 Hz, 1H), 6.53-6.46 (m, 1H), 6.44 (d, J8.9 Hz, 1H), 4.99 (t, J 6.9 Hz, 1H), 4.63 (s, 1H), 3.60 (dt, J 15.8, 8.4 Hz, 1H), 3.09 (d, J 13.8 Hz, 1H), 2.53 (d, J 14.1 Hz, 1H), 1.79 (d, J13.7 Hz, 1H), 1.62 (s, 6H).

Example 2

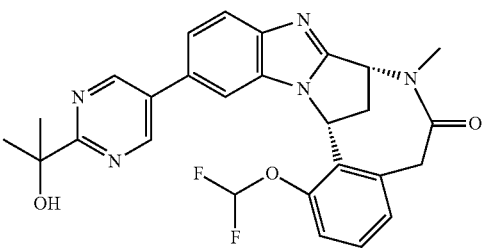 [SMILES: CN1C(=O)Cc2cccc(OC(F)F)c2[C@H]2C[C@@H]1c1nc3ccc(-c4cnc(C(C)(C)O)nc4)cc3n12]

(8R,15R)-1-(difluoromethoxy)-12-[2-(2-hydroxypropan-2-yl)pyrimidin-5-yl]-7-methyl-5,7,8,15-tetrahydro-6H-8,15-methanobenzimidazo[1,2-b][2,5]benzodiazonin-6-one The title compound was prepared from Intermediate 20 (9.7 mg, 0.024 mmol) and 2-(1-hydroxy-1-methylethyl)pyrimidine-5-boronic acid pinacol ester (17 mg, 0.060 mmol) following the procedure described for Example 1. The crude material was purified by two successive purifications on preparative basic LCMS to give the title compound (4 mg, 33%) as an off white solid. LCMS Method 1 (ES+) RT 3.65 min, 506 (M+H)$^+$. LCMS Method 2 (ES+) RT 3.69 min, 506 (M+H)$^+$. $^1$H NMR (400 MHz, Chloroform-d) δ 8.87 (s, 2H), 7.97 (d, J 8.5 Hz, 1H), 7.52 (dd, J 8.5, 1.7 Hz, 1H), 7.36 (d, J 1.7 Hz, 1H), 7.27 (d, J 5.7 Hz, 1H), 7.18 (d, J 8.8 Hz, 1H), 7.14 (dd, J 7.6, 1.3 Hz, 1H), 6.73 (dd, J 73.8, 72.9 Hz, 1H), 6.43 (d, J 8.8 Hz, 1H), 5.02 (d, J 8.2 Hz, 1H), 4.62 (s, 1H), 3.68-3.51 (m, 1H), 3.20 (s, 3H), 3.15 (d, J 14.0 Hz, 1H), 2.47 (d, J 14.3 Hz, 1H), 1.81 (d, J 14.0 Hz, 1H), 1.62 (s, 6H).

Example 3

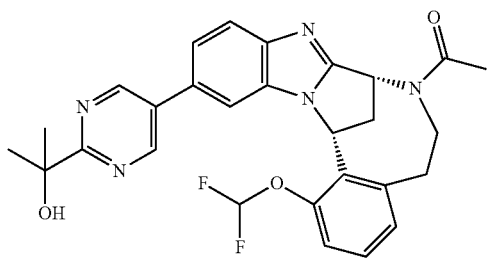 [SMILES: CC(=O)N1CCc2cccc(OC(F)F)c2[C@H]2C[C@@H]1c1nc3ccc(-c4cnc(C(C)(C)O)nc4)cc3n12]

1-[(8R,15R)-1-(difluoromethoxy)-12-[2-(2-hydroxypropan-2-yl)pyrimidin-5-yl]-5,15-dihydro-6H-8,15-methanobenzimidazo[1,2-b][2,5]benzodiazonin-7(8H)-yl]ethanone The title compound was prepared from Intermediate 22 (14 mg, 0.034 mmol) and 2-(1-hydroxy-1-methylethyl)pyrimidine-5-boronic acid pinacol ester (23 mg, 0.084 mmol) following the procedure described for Example 1. The crude material was purified by preparative LC-MS basic conditions to give the title compound (7.2 mg, 41%) as a white solid. LCMS Method 1 (ES+) RT 1.95 min, 520 (M+H)$^+$. LCMS Method 2 (ES+) RT 2.08 min, 520 (M+H)$^+$.

The invention claimed is:
1. A compound of formula (I) or an N-oxide thereof, or a pharmaceutically acceptable salt thereof:

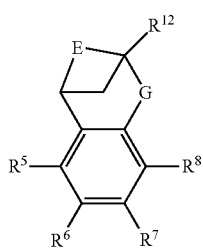

wherein
G- represents —O—C(O)—N(R$^f$)—, —N(R$^f$)—C(O)—N(R$^f$) or —N(R$^f$)—S(O)$_2$—N(R$^f$)—; or -G-represents —N(R$^f$)—C(O)—CH$_2$—, CH$_2$—N(R$^f$)—C(O)—, —C(O)—N(R$^f$)—CH$_2$—, —N(R$^g$)—CH$_2$—CH$_2$—, —S(O)$_2$—N(R$^f$)—CH$_2$—, —N(R$^f$)—S(O)$_2$—CH$_2$—, —O—CH$_2$—CH$_2$—, —S—CH$_2$—CH$_2$—, —S(O)—CH$_2$—CH$_2$—, —S(O)$_2$—CH$_2$—CH$_2$—, —S(O)(N—R$^f$)—CH$_2$—CH$_2$—, —O—C(O)—CH$_2$—, —O—S(O)$_2$—N(R$^f$)—, —N(R$^f$)—C(O)—O—CH$_2$, or —N(R$^f$)—C=N(R$^f$)—CH$_2$, any of which groups may be optionally substituted by one or more substituents;
E represents a fused heteroaromatic ring system selected from the groups of formula (Ea), (Eb) and (Ec),

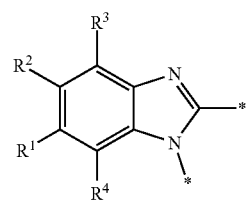

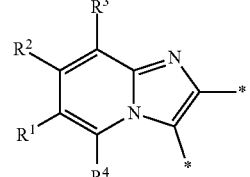

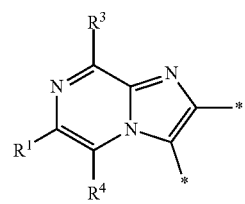

wherein the asterisk (*) represents the site of attachment of E to the remainder of the molecule;
R$^1$ represents hydrogen, halogen, cyano, trifluoromethyl, trifluoromethoxy, —OR$^a$, —SR$^a$, —SOR$^a$, —SO$_2$R$^a$, —NR$^b$R$^c$, —NR$^c$COR$^d$, —NR$^c$CO$_2$R$^d$, —NHCONR$^b$R$^c$, —NR$^c$SO$_2$R$^e$, —COR$^d$, —CO$_2$R$^d$, —CONR$^b$R$^c$, —SO$_2$NR$^b$R$^c$ or —S(O)(N—R$^b$)R$^e$; or R$^1$ represents C$_{1-6}$ alkyl, C$_{3-7}$ cycloalkyl, C$_{4-7}$ cycloalkenyl, aryl, aryl(C$_{1-6}$)alkyl, C$_{3-7}$ heterocycloalkyl, C$_{3-7}$ heterocycloalkenyl, heteroaryl, heteroaryl(C$_{1-6}$)alkyl, heteroaryl-aryl, (C$_{3-7}$)heterocycloalkyl(C$_{1-6}$)alkyl-aryl-, (C$_{3-7}$)heterocycloalkenyl-aryl-, (C$_{3-7}$)cycloalkyl-heteroaryl-, (C$_{3-7}$)cycloalkyl(C$_{1-6}$)alkyl-heteroaryl-, (C$_{4-7}$)cycloalkenyl-heteroaryl-, (C$_{4-9}$)bicycloalkyl-heteroaryl-, (C$_{3-7}$)heterocycloalkyl-heteroaryl-, (C$_{3-7}$)heterocycloalkyl(C$_{1-6}$)alkyl-heteroaryl-, (C$_{3-7}$)heterocycloalkenyl-heteroaryl-, (C$_{4-9}$)heterobicycloalkyl-heteroaryl- or (C$_{4-9}$)spiroheterocycloalkyl-heteroaryl-, any of which groups may be optionally substituted by one or more substituents;
R$^2$ represents hydrogen, halogen, cyano, nitro, hydroxy, trifluoromethyl, trifluoromethoxy or —OR$^a$; or R$^2$ represents C$_{1-6}$ alkyl optionally substituted by one or more substituents;

$R^3$ and $R^4$ independently represent hydrogen, halogen or trifluoromethyl; or $R^3$ and $R^4$ independently represent $C_{1-6}$ alkyl, optionally substituted by one or more substituents;

$R^5$ and $R^8$ independently represent hydrogen, halogen, hydroxy, cyano, trifluoromethyl, difluoromethoxy, trifluoromethoxy, —$OR^a$, or $C_{1-6}$ alkylsulphonyl; or $R^5$ and $R^8$ independently represent $C_{1-6}$ alkyl optionally substituted by one or more substituents;

$R^6$ and $R^7$ independently represent hydrogen, halogen, trifluoromethyl, $C_{1-6}$ alkyl or $C_{1-6}$ alkoxy;

$R^{12}$ represents hydrogen or $C_{1-6}$ alkyl;

$R^a$ represents $C_{1-6}$ alkyl, $C_{3-7}$ cycloalkyl, $C_{3-7}$ heterocycloalkyl, aryl, aryl($C_{1-6}$)alkyl, heteroaryl or heteroaryl($C_{1-6}$)alkyl, any of which groups may be optionally substituted by one or more substituents;

$R^b$ and $R^c$ independently represent hydrogen or trifluoromethyl; or $R^b$ and $R^c$ independently represent $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents; or $R^b$ and $R^c$, when taken together with the nitrogen atom to which they are both attached, represent a heterocyclic moiety selected from azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl, homopiperazin-1-yl, (imino)(oxo)thiazinan-4-yl, (oxo)thiazinan-4-yl and (dioxo)thiazinan-4-yl, any of which groups may be optionally substituted by one or more substituents;

$R^d$ represents hydrogen; or $R^d$ represents $C_{1-6}$ alkyl, $C_{3-7}$ cycloalkyl, aryl, $C_{3-7}$ heterocycloalkyl or heteroaryl, any of which groups may be optionally substituted by one or more substituents;

$R^e$ represents $C_{1-6}$ alkyl, aryl or heteroaryl, any of which groups may be optionally substituted by one or more substituents;

$R^f$ represents hydrogen; or $R^f$ represents $C_{1-6}$ alkyl, $C_{3-7}$ cycloalkyl, or $C_{3-7}$ heterocycloalkyl, $C_{1-6}$ alkylcarbonyl, $C_{1-6}$ alkylsulfonyl any of which groups may be optionally substituted by one or more substituents; and $R^g$ represents hydrogen or ($C_{2-6}$)alkoxycarbonyl; or $R^g$ represents $C_{1-6}$ alkyl, $C_{3-7}$ cycloalkyl, $C_{3-7}$ heterocycloalkyl, heteroaryl, —CO—($C_{1-6}$)alkyl, or —$SO_2$—($C_{1-6}$)alkyl, —CO—($C_{3-7}$)heterocycloalkyl, —$SO_2$—($C_3$-)cycloalkyl, —$SO_2$—($C_{3-7}$)heterocycloalkyl, —$SO_2$-aryl, or —$SO_2$-heteroaryl, any of which groups may be optionally substituted by one or more substituents.

2. The compound as claimed in claim 1 represented by formula (IIB), an N-oxide thereof, or a pharmaceutically acceptable salt thereof:

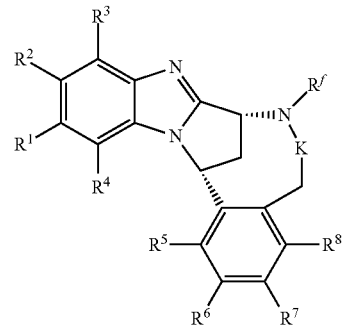

(IIB)

wherein

K represents $CH_2$ or C=O.

3. The compound as claimed in claim 1 wherein $R^1$ represents $C_{3-7}$ heterocycloalkyl, heteroaryl, ($C_{3-7}$)cycloalkyl-heteroaryl or ($C_{3-7}$)heterocycloalkyl-heteroaryl, any of which groups may be optionally substituted by one or more substituents.

4. The compound as claimed in claim 1 which is (8R,15R)-1-(difluoromethoxy)-12-[2-(2-hydroxypropan-2-yl)pyrimidin-5-yl]-5,7,8,15-tetrahydro-6H-8,15-methanobenzimidazo[1,2-b][2,5]benzodiazonin-6-one; (8R,15R)-1-(difluoromethoxy)-12-[2-(2-hydroxypropan-2-yl)pyrimidin-5-yl]-7-methyl-5,7,8,15-tetrahydro-6H-8,15-methanobenzimidazo[1,2-b][2,5]benzodiazonin-6-one; or 1-[(8R,15R)-1-(difluoromethoxy)-12-[2-(2-hydroxypropan-2-yl)pyrimidin-5-yl]-5,15-dihydro-6H-8,15-methanobenzimidazo[1,2-b][2,5]benzodiazonin-7(8H)-yl]ethanone.

5. A pharmaceutical composition comprising a compound of formula (I) as defined in claim 1 or an N-oxide thereof, or a pharmaceutically acceptable salt thereof, in association with a pharmaceutically acceptable carrier.

6. The pharmaceutical composition as claimed in claim 5 further comprising an additional pharmaceutically active ingredient.

7. A method for the treatment of rheumatoid arthritis or Crohn's disease which comprises administering to a patient in need of such treatment an effective amount of a compound of formula (I) as defined in claim 1 or an N-oxide thereof, or a pharmaceutically acceptable salt thereof.

* * * * *